United States Patent
Caballero et al.

(10) Patent No.: US 10,111,987 B2
(45) Date of Patent: Oct. 30, 2018

(54) MARKED FLUOROPOLYMER SURFACES AND METHOD OF MANUFACTURING SAME

(71) Applicant: Innovatech, LLC, Chicago, IL (US)

(72) Inventors: Adino D. Caballero, Hanover Park, IL (US); Bruce Nesbitt, Chicago, IL (US); Charles Berkelhamer, Highland Park, IL (US); George F. Osterhout, Park Ridge, IL (US)

(73) Assignee: Innovatech, LLC, Chicago, IL (US)

( * ) Notice: Subject to any disclaimer, the term of this patent is extended or adjusted under 35 U.S.C. 154(b) by 0 days.

(21) Appl. No.: 15/962,361

(22) Filed: Apr. 25, 2018

(65) Prior Publication Data

US 2018/0236144 A1    Aug. 23, 2018

Related U.S. Application Data

(63) Continuation of application No. 15/654,117, filed on Jul. 19, 2017, now Pat. No. 9,962,470, which is a
(Continued)

(51) Int. Cl.
*B05D 1/32* (2006.01)
*B05D 5/06* (2006.01)
(Continued)

(52) U.S. Cl.
CPC ............. *A61L 31/10* (2013.01); *A61L 31/048* (2013.01); *B05D 7/02* (2013.01); *A61L 2420/02* (2013.01);
(Continued)

(58) Field of Classification Search
CPC ............. B05D 1/002; B05D 1/32; B05D 5/06
See application file for complete search history.

(56) References Cited

U.S. PATENT DOCUMENTS

| 1,617,102 A | 2/1927 | Cohn |
| 1,772,846 A | 8/1930 | Spolidoro |

(Continued)

FOREIGN PATENT DOCUMENTS

| DE | 10134008 | 1/2003 | |
| DE | 10338338 A1 * | 3/2005 | ........... A61L 29/041 |

(Continued)

OTHER PUBLICATIONS

Acetal (POM) Engineering Property Data Article, published by Material Property Data, [online] [retrieved from the Internet Nov. 26, 2007] <URL:www.matweb.com/reference/acetalpolymer.aspx>.

(Continued)

*Primary Examiner* — Cachet I Sellman
(74) *Attorney, Agent, or Firm* — Neal, Gerber & Eisenberg LLP

(57) ABSTRACT

A method of manufacturing a coated low-friction medical device, such as low-friction medical tubing, including applying a coating to one or more selected portions of a surface of low-friction medical tubing to indicate at least one marking formed along the surface of the low-friction medical tubing, and simultaneously or substantially simultaneously: (a) curing the applied coating to a designated temperature (which is above the temperature at which the low-friction medical tubing begins to decompose and shrink) to adhere the applied coating to the surface of the low-friction medical tubing, (b) utilizing one or more anti-shrinking devices to counteract or otherwise inhibit the shrinking of the low-friction medical tubing, and (c) exhausting any harmful byproducts resulting from curing the low-friction medical tubing to a temperate above the temperature at which the low-friction medical tubing begins to decompose.

36 Claims, 27 Drawing Sheets

Related U.S. Application Data continuation of application No. 14/526,099, filed on Oct. 28, 2014, now Pat. No. 9,744,271, which is a continuation of application No. 13/416,743, filed on Mar. 9, 2012, now Pat. No. 8,900,652.

(60) Provisional application No. 61/452,380, filed on Mar. 14, 2011.

(51) Int. Cl.
*A61L 31/10* (2006.01)
*A61L 31/04* (2006.01)
*B05D 7/02* (2006.01)
*A61M 25/00* (2006.01)
*B05D 3/12* (2006.01)
*B05D 3/02* (2006.01)
*B05D 1/00* (2006.01)

(52) U.S. Cl.
CPC ..... *A61M 25/0009* (2013.01); *A61M 25/0045* (2013.01); *A61M 2025/0008* (2013.01); *B05D 1/002* (2013.01); *B05D 1/32* (2013.01); *B05D 3/0254* (2013.01); *B05D 3/12* (2013.01); *B05D 5/06* (2013.01); *Y10T 428/1393* (2015.01)

(56) References Cited

U.S. PATENT DOCUMENTS

| | | |
|---|---|---|
| 2,049,769 A | 8/1936 | Gray |
| 2,241,282 A | 5/1941 | Wackerle |
| 2,241,283 A | 5/1941 | Wackerle |
| 2,735,258 A | 2/1956 | Crandall |
| 2,861,417 A | 11/1958 | Crandall |
| 2,892,374 A | 6/1959 | Ralls, Jr. |
| 3,085,912 A | 4/1963 | Friese |
| 3,099,595 A | 7/1963 | Allbaugh |
| 3,120,144 A | 2/1964 | Bayer |
| 3,706,883 A | 12/1972 | McIntyre |
| 3,812,842 A | 5/1974 | Rodriguez |
| 3,857,934 A | 12/1974 | Bernstein et al. |
| 4,003,369 A | 1/1977 | Heilman et al. |
| 4,008,351 A | 2/1977 | Inoue et al. |
| 4,016,714 A | 4/1977 | Crandall, Jr. |
| 4,080,706 A | 3/1978 | Heilman et al. |
| 4,336,087 A | 6/1982 | Martuch et al. |
| 4,377,620 A | 3/1983 | Alexander |
| 4,382,358 A | 5/1983 | Tappe et al. |
| 4,539,228 A | 9/1985 | Lazarus |
| 4,540,628 A | 9/1985 | Oberdeck et al. |
| 4,570,170 A | 2/1986 | Hiraishi et al. |
| 4,577,637 A | 3/1986 | Mueller, Jr. |
| 4,645,491 A | 2/1987 | Evans |
| 4,724,846 A | 2/1988 | Evans, III |
| 4,779,628 A | 10/1988 | Machek |
| 4,796,637 A | 1/1989 | Mascuch et al. |
| 4,799,496 A | 1/1989 | Hargreaves et al. |
| 4,846,193 A | 7/1989 | Tremulis et al. |
| 4,854,330 A | 8/1989 | Evans, III et al. |
| 4,875,489 A | 10/1989 | Messner et al. |
| 4,895,168 A | 1/1990 | Machek |
| 4,922,923 A | 5/1990 | Gambale et al. |
| 4,951,686 A | 8/1990 | Herlitze |
| 4,966,163 A | 10/1990 | Kraus et al. |
| 5,034,005 A | 7/1991 | Appling |
| 5,038,458 A | 8/1991 | Wagoner et al. |
| 5,063,935 A | 11/1991 | Gambale |
| 5,084,022 A | 1/1992 | Claude |
| 5,091,284 A | 2/1992 | Bradfield |
| 5,107,852 A | 4/1992 | Davidson et al. |
| 5,114,401 A | 5/1992 | Stuart et al. |
| 5,117,838 A | 6/1992 | Palmer et al. |
| 5,117,839 A | 6/1992 | Dance |
| 5,144,959 A | 9/1992 | Gambale et al. |
| 5,149,965 A | 9/1992 | Marks |
| 5,154,705 A | 10/1992 | Fleischhacker et al. |
| 5,165,013 A | 11/1992 | Faris |
| 5,165,421 A | 11/1992 | Fleischhacker et al. |
| 5,174,302 A | 12/1992 | Palmer |
| 5,203,777 A | 4/1993 | Lee |
| 5,211,636 A | 5/1993 | Mische |
| 5,234,002 A | 8/1993 | Chan |
| 5,241,970 A | 9/1993 | Johlin, Jr. et al. |
| 5,243,996 A | 9/1993 | Hall |
| 5,260,985 A | 11/1993 | Mosby |
| 5,265,622 A | 11/1993 | Barbere |
| 5,267,955 A | 12/1993 | Hanson |
| 5,271,415 A | 12/1993 | Foerster et al. |
| 5,273,526 A | 12/1993 | Dance et al. |
| 5,279,546 A | 1/1994 | Mische et al. |
| 5,279,573 A | 1/1994 | Klosterman |
| 5,282,478 A | 2/1994 | Fleischhacker, Jr. et al. |
| 5,300,048 A | 4/1994 | Drewes, Jr. et al. |
| 5,345,945 A | 9/1994 | Hodgson et al. |
| 5,353,808 A | 10/1994 | Viera |
| 5,360,403 A | 11/1994 | Mische |
| 5,373,619 A | 12/1994 | Fleischhacker et al. |
| 5,376,083 A | 12/1994 | Mische |
| 5,379,779 A | 1/1995 | Rowland et al. |
| 5,409,004 A | 4/1995 | Sloan |
| 5,433,200 A | 7/1995 | Fleischhacker, Jr. |
| 5,443,081 A | 8/1995 | Klosterman |
| D363,544 S | 10/1995 | Rowland et al. |
| D363,776 S | 10/1995 | Rowland et al. |
| 5,479,938 A | 1/1996 | Weier |
| 5,497,783 A | 3/1996 | Urick et al. |
| 5,497,786 A | 3/1996 | Urick |
| 5,498,250 A | 3/1996 | Prather |
| 5,546,958 A | 8/1996 | Thorud et al. |
| 5,551,444 A | 9/1996 | Finlayson |
| 5,559,297 A | 9/1996 | Yoshikawa et al. |
| 5,606,981 A | 3/1997 | Tartacower et al. |
| 5,610,348 A | 3/1997 | Aladin et al. |
| 5,634,897 A | 6/1997 | Dance et al. |
| 5,640,970 A | 6/1997 | Arenas |
| 5,665,103 A | 9/1997 | Lafontaine et al. |
| 5,669,878 A | 9/1997 | Dickinson et al. |
| 5,724,989 A | 3/1998 | Dobson |
| 5,728,042 A | 3/1998 | Schwager |
| H1715 H | 4/1998 | Longeat |
| 5,740,473 A | 4/1998 | Tanaka et al. |
| 5,741,267 A | 4/1998 | Jorneus et al. |
| 5,759,174 A | 6/1998 | Fischell et al. |
| 5,782,811 A | 7/1998 | Samson et al. |
| 5,800,522 A | 9/1998 | Campbell et al. |
| 5,801,319 A | 9/1998 | Hebestreit |
| 5,804,633 A | 9/1998 | Loftin et al. |
| 5,807,279 A | 9/1998 | Viera |
| 5,830,155 A | 11/1998 | Frechette et al. |
| 5,836,892 A | 11/1998 | Lorenzo |
| 5,876,783 A | 3/1999 | Dobson |
| 5,883,319 A | 3/1999 | Hebestreit |
| 5,885,227 A | 3/1999 | Finlayson |
| 5,897,819 A | 4/1999 | Miyata et al. |
| 5,898,117 A | 4/1999 | Ishida |
| 5,907,113 A | 5/1999 | Hebestreit |
| 5,908,413 A | 6/1999 | Lange et al. |
| 5,919,126 A | 7/1999 | Armini |
| 5,919,170 A | 7/1999 | Woessner |
| 5,941,706 A | 8/1999 | Ura |
| 5,948,489 A | 9/1999 | Hopkins |
| 5,970,119 A | 10/1999 | Hofmann |
| 5,984,877 A | 11/1999 | Fleischhacker, Jr. |
| 6,036,682 A | 3/2000 | Lange et al. |
| 6,042,605 A | 3/2000 | Martin et al. |
| 6,048,620 A | 4/2000 | Zhong |
| 6,050,958 A | 4/2000 | Dickinson et al. |
| 6,083,167 A | 7/2000 | Fox et al. |
| 6,093,157 A | 7/2000 | Chandrasekaran |
| 6,093,678 A | 7/2000 | Hamada et al. |
| 6,113,576 A | 9/2000 | Dance et al. |
| 6,139,540 A | 10/2000 | Rost et al. |
| 6,140,267 A | 10/2000 | Gundjian |
| 6,143,013 A | 11/2000 | Samson et al. |

(56) References Cited

U.S. PATENT DOCUMENTS

| | | |
|---|---|---|
| 6,168,570 B1 | 1/2001 | Ferrera |
| 6,179,788 B1 | 1/2001 | Sullivan |
| 6,193,706 B1 | 2/2001 | Thorud et al. |
| 6,211,450 B1 | 4/2001 | Ishida |
| 6,238,847 B1 | 5/2001 | Axtell, III et al. |
| 6,248,942 B1 | 6/2001 | Hebestreit et al. |
| 6,273,858 B1 | 8/2001 | Fox et al. |
| 6,277,108 B1 | 8/2001 | Mcbroom et al. |
| 6,306,105 B1 | 10/2001 | Rooney et al. |
| 6,315,790 B1 | 11/2001 | Gerberding et al. |
| 6,340,368 B1 | 1/2002 | Verbeck |
| 6,348,646 B1 | 2/2002 | Parker et al. |
| 6,355,058 B1 | 3/2002 | Pacetti et al. |
| 6,361,557 B1 | 3/2002 | Gittings et al. |
| 6,370,304 B1 | 4/2002 | Mills et al. |
| 6,387,060 B1 | 5/2002 | Jalisi |
| 6,402,777 B1 | 6/2002 | Globerman et al. |
| 6,425,927 B1 | 7/2002 | Haupt-Stephan et al. |
| 6,428,512 B1 | 8/2002 | Anderson |
| 6,468,079 B1 | 10/2002 | Fischer et al. |
| 6,475,169 B2 | 11/2002 | Ferrera |
| 6,491,646 B1 | 12/2002 | Blackledge |
| 6,501,827 B1 | 12/2002 | Takasawa |
| 6,501,992 B1 | 12/2002 | Belden et al. |
| 6,503,310 B1 | 1/2003 | Sullivan |
| 6,520,923 B1 | 2/2003 | Jalisi |
| 6,520,934 B1 | 2/2003 | Lee et al. |
| 6,528,709 B2 | 3/2003 | Hebestreit et al. |
| 6,540,721 B1 | 4/2003 | Voyles et al. |
| 6,554,942 B2 | 4/2003 | Solar et al. |
| 6,605,049 B1 | 8/2003 | Wagner et al. |
| 6,612,998 B2 | 9/2003 | Gosiengfiao et al. |
| 6,613,002 B1 | 9/2003 | Clark et al. |
| 6,617,515 B1 | 9/2003 | Yeung |
| 6,619,778 B2 | 9/2003 | Igarashi |
| 6,620,114 B2 | 9/2003 | Vrba et al. |
| 6,623,504 B2 | 9/2003 | Vrba et al. |
| 6,626,869 B1 | 9/2003 | Bint |
| 6,635,082 B1 | 10/2003 | Hossainy et al. |
| 6,636,758 B2 | 10/2003 | Sanchez et al. |
| 6,638,589 B1 | 10/2003 | Jarvenkyla |
| 6,652,568 B1 | 11/2003 | Becker et al. |
| 6,652,579 B1 | 11/2003 | Cox et al. |
| 6,673,025 B1 | 1/2004 | Richardson et al. |
| 6,679,853 B1 | 1/2004 | Jalisi |
| 6,680,121 B2 | 1/2004 | Sakoske et al. |
| 6,733,503 B2 | 5/2004 | Layrolle et al. |
| 6,758,857 B2 | 7/2004 | Cicanta et al. |
| 6,765,136 B2 | 7/2004 | Van Pamel |
| D496,728 S | 9/2004 | Holsinger |
| 6,811,805 B2 | 11/2004 | Gilliard et al. |
| 6,811,958 B2 | 11/2004 | Iwami et al. |
| 6,835,454 B1 | 12/2004 | Randa et al. |
| 6,855,161 B2 | 2/2005 | Boylan et al. |
| 6,942,652 B1 | 9/2005 | Pressly, Sr. et al. |
| 6,994,883 B2 | 2/2006 | Layrolle et al. |
| 7,022,086 B2 | 4/2006 | Ehr |
| 7,033,325 B1 | 4/2006 | Sullivan |
| 7,147,634 B2 | 12/2006 | Nesbitt |
| 7,150,756 B2 | 12/2006 | Levinson et al. |
| 7,153,277 B2 | 12/2006 | Skujins et al. |
| 7,160,297 B2 | 1/2007 | Nesbitt |
| 7,163,509 B2 | 1/2007 | Abe |
| 7,182,757 B2 | 2/2007 | Miyata et al. |
| 7,217,876 B2 | 5/2007 | Allen et al. |
| 7,241,406 B2 | 7/2007 | Solar et al. |
| 7,255,685 B2 | 8/2007 | Pressly, Sr. et al. |
| 7,261,925 B2 | 8/2007 | Nesbitt |
| 7,278,973 B2 | 10/2007 | Iwami |
| 7,288,091 B2 | 10/2007 | Nesbitt |
| 7,296,333 B2 | 11/2007 | Jalisi |
| 7,309,235 B2 | 12/2007 | Wilk |
| 7,311,714 B1 | 12/2007 | Wascher |
| 7,390,326 B2 | 6/2008 | Nesbitt |
| 7,399,296 B2 | 7/2008 | Poole et al. |
| 7,408,101 B2 | 8/2008 | Shelton |
| 7,410,665 B2 | 8/2008 | Ragheb et al. |
| 7,434,437 B2 | 10/2008 | Kato et al. |
| 7,455,646 B2 | 11/2008 | Richardson et al. |
| 7,473,417 B2 | 1/2009 | Zeltinger et al. |
| 7,517,342 B2 | 4/2009 | Scott et al. |
| 7,714,217 B2 * | 5/2010 | Nesbitt ............... B05D 3/007 84/173 |
| 7,811,623 B2 | 10/2010 | Nesbitt |
| 2002/0082681 A1 | 6/2002 | Boylan et al. |
| 2002/0136893 A1 | 9/2002 | Schlesinger |
| 2003/0032896 A1 | 2/2003 | Bosley, Jr. et al. |
| 2003/0060731 A1 | 3/2003 | Fleischhacker |
| 2003/0060783 A1 | 3/2003 | Koole et al. |
| 2003/0060872 A1 | 3/2003 | Gomringer et al. |
| 2003/0109865 A1 | 6/2003 | Greep et al. |
| 2003/0120302 A1 | 6/2003 | Minck, Jr. et al. |
| 2003/0139764 A1 | 7/2003 | Levinson et al. |
| 2003/0199759 A1 | 10/2003 | Richard |
| 2003/0203991 A1 | 10/2003 | Schottman et al. |
| 2003/0216642 A1 | 11/2003 | Pepin et al. |
| 2004/0044399 A1 | 3/2004 | Ventura |
| 2004/0122509 A1 | 6/2004 | Brodeur |
| 2004/0220608 A1 | 11/2004 | D'aquanni et al. |
| 2004/0253185 A1 | 12/2004 | Herweck et al. |
| 2004/0267161 A1 * | 12/2004 | Osborne ............... A61L 31/10 600/585 |
| 2005/0003103 A1 | 1/2005 | Krupa |
| 2005/0011332 A1 | 1/2005 | Dronge |
| 2005/0038500 A1 | 2/2005 | Boylan et al. |
| 2005/0087520 A1 | 4/2005 | Wang et al. |
| 2005/0133941 A1 | 6/2005 | Schuhmacher |
| 2005/0148902 A1 | 7/2005 | Minar et al. |
| 2005/0154075 A1 | 7/2005 | Siegel |
| 2005/0165472 A1 | 7/2005 | Glocker |
| 2005/0187466 A1 | 8/2005 | Glocker et al. |
| 2005/0202158 A1 | 9/2005 | Millas et al. |
| 2005/0261670 A1 | 11/2005 | Weber et al. |
| 2005/0288773 A1 | 12/2005 | Glocker et al. |
| 2006/0036316 A1 | 2/2006 | Zeltinger et al. |
| 2006/0118612 A1 | 6/2006 | Christoffersen et al. |
| 2006/0174745 A1 | 8/2006 | D'Addario |
| 2006/0174746 A1 | 8/2006 | Everly |
| 2006/0184112 A1 | 8/2006 | Horn et al. |
| 2006/0198976 A1 | 9/2006 | Trapp |
| 2006/0201601 A1 | 9/2006 | Furst et al. |
| 2006/0211952 A1 | 9/2006 | Kennedy, II |
| 2006/0257653 A1 | 11/2006 | Tsujimoto et al. |
| 2006/0259033 A1 | 11/2006 | Nesbitt |
| 2006/0271135 A1 | 11/2006 | Minar et al. |
| 2007/0021811 A1 | 1/2007 | D'aquanni et al. |
| 2007/0043333 A1 | 2/2007 | Kampa et al. |
| 2007/0093811 A1 | 4/2007 | Nesbitt |
| 2007/0100279 A1 | 5/2007 | Bates |
| 2007/0118113 A1 | 5/2007 | Nesbitt |
| 2007/0184085 A1 | 8/2007 | Radhakrishnan et al. |
| 2007/0207182 A1 | 9/2007 | Weber et al. |
| 2007/0208373 A1 | 9/2007 | Zaver et al. |
| 2007/0212547 A1 | 9/2007 | Fredrickson et al. |
| 2007/0266542 A1 | 11/2007 | Melsheimer |
| 2008/0008654 A1 | 1/2008 | Clarke et al. |
| 2008/0027532 A1 | 1/2008 | Boylan et al. |
| 2008/0032060 A1 | 2/2008 | Nesbitt |
| 2008/0033373 A1 | 2/2008 | Koole et al. |
| 2008/0050509 A1 | 2/2008 | Nesbitt |
| 2008/0108974 A1 | 5/2008 | Yee |
| 2008/0288056 A1 | 11/2008 | Simpson et al. |
| 2009/0162530 A1 | 6/2009 | Nesbitt |
| 2009/0162531 A1 | 6/2009 | Nesbitt |
| 2009/0211909 A1 * | 8/2009 | Nesbitt ............... A61L 31/10 204/487 |
| 2010/0000621 A1 | 1/2010 | Kamata et al. |

FOREIGN PATENT DOCUMENTS

| | | |
|---|---|---|
| EP | 0 321 091 | 6/1989 |
| EP | 0 624 380 | 11/1994 |
| EP | 0 771 572 | 5/1997 |
| EP | 0 832 664 | 4/1998 |

(56) References Cited

FOREIGN PATENT DOCUMENTS

| | | |
|---|---|---|
| EP | 0 987 042 | 3/2000 |
| EP | 0 749 334 | 6/2000 |
| EP | 1 025 811 | 8/2000 |
| EP | 1 062 965 | 12/2000 |
| EP | 0 833 676 | 9/2003 |
| EP | 1 433 438 | 6/2004 |
| GB | 2 177 270 | 10/1983 |
| WO | WO 1995/014501 | 6/1995 |
| WO | WO 2001/045592 | 6/2001 |
| WO | WO 2002/047549 | 6/2002 |
| WO | WO 2004/033016 | 4/2004 |
| WO | WO 2004/049970 | 6/2004 |
| WO | WO 2004/110519 | 12/2004 |
| WO | WO 2005/094486 | 10/2005 |
| WO | WO 2005/122961 | 12/2005 |
| WO | WO 2006/002199 | 1/2006 |
| WO | WO 2006/006971 | 1/2006 |
| WO | WO 2006/019983 | 2/2006 |
| WO | WO 2007/100556 | 9/2007 |
| WO | WO 2008/097359 | 8/2008 |

OTHER PUBLICATIONS

Advancements in Laser Marking of Plastics Article, published by The Sabreen Group, Inc., prior to Jul. 2008.
Applications of ePTFE Brochure, published by Gore, printed on Feb. 14, 2011.
Bottles, PFA, FEP and PTFE Brochure, published by Jensen Inert Products, printed on Nov. 6, 2012, available prior to Mar. 14, 2011.
Breakthroughs in Laser Marking Brochure, published by The Sabreen Group, Inc., [online] [retrieved from the Internet Nov. 26, 2007] <URL:www.plasticslasermarking.com/breakthroughs.htm>.
ClearClad: "Electrophoretic Coating", pp. 1-4, 1996-2002.
Dispersed Pigments Brochure, published by Colorant-Chromatics, printed on Feb. 14, 2011.
FEP Compounds Brochure, published by Colorant-Chromatics, printed on Feb. 14, 2011.
FEP Concentrates Brochure, published by Colorant-Chromatics, printed on Feb. 14, 2011.
FEP Striping Ink Brochure, published by Colorant-Chromatics, printed on Feb. 14, 2011.
GEM 1000 Series Silicone Ink Brochure, published by GEM, printed on Feb. 14, 2011.
GEM 200 Series Ink Brochure, published by GEM, printed on Feb. 14, 2011.
GEM 2100 Series Dye Brochure, published by GEM, printed on Feb. 14, 2011.
GEM 4700 Series PTFE Colorants Brochure, published by GEM, printed on Feb. 14, 2011.
GEM 6000 Series High Temp Ink Brochure, published by GEM, printed on Feb. 14, 2011.
GEM 6300 Top Color Coat Paint Brochure, published by GEM, printed on Feb. 14, 2011.
GEM 6400 Series Bandmarking/Spiral Striping Ink Brochure, published by GEM, printed on Feb. 14, 2011.
GEM 6500 Marking Ink Brochure, published by GEM, printed on Feb. 14, 2011.
GEM 7400 Series Bandmarking Brochure, published by GEM, printed on Feb. 14, 2011.
GEM 7700 Band Marking Brochure, published by GEM, printed on Feb. 14, 2011.
GEM 7900 Series Brochure, published by GEM, printed on Feb. 14, 2011.
GEM 900 NA Hi-Speed Ink Brochure, published by GEM, printed on Feb. 14, 2011.
GEM Water-Based WB78 Brochure, published by GEM, printed on Feb. 14, 2011.
GEM WB1140 High-Temp Marking Ink Brochure, published by GEM, printed on Feb. 14, 2011.
GEM WB1150 High-Temp Striping Ink Brochure, published by GEM, printed on Feb. 14, 2011.
Hydrophilic Coatings, Product Leaflet, published by MCTec, [online] [retrieved from the Internet Nov. 2, 2008] <URL:www.mctecbv.com>.
Inks for FEP marking Brochure, published by Colorant-Chromatics, printed on Feb. 14, 2011.
Inks for PFA marking Brochure, published by Colorant Chromatics, printed on Nov. 6, 2012, available prior to Mar. 14, 2011.
Kahn et al Removal of Volatile Organic Compounds from polluted air, Journal of Loss Prevention in the Process Industries 13 (2000) 527-545.
Karlsen, Haakon O., Modification of Fluoropolymers and PEEK Article, published by Business Briefing: Medical Device Manufacturing & Technology, 2002, printed on Feb. 14, 2011.
Marking Processes for Use in Harsh Environments Article, published by The Sabreen Group, Inc., [online] [retrieved from the Internet Nov. 26, 2007] <URL:www.plasticslasermarking.com/laser_marking_harsh_environments.htm>.
Material Safety Data Sheet for FEP Striping Ink Brochure, published by Colorant-Chromatics, printed on Feb. 14, 2011.
Nagaoka et al., "Low Friction Hydrophillic Surface for medical Device", BioMaterials, Aug. 11, 1990, pp. 419-424.
PFA compounds Brochure, published by Colorant Chromatics, printed on Nov. 6, 2012, available prior to Mar. 14, 2011.
PFA concentrates Brochure, published by Colorant Chromatics, printed on Nov. 6, 2012, available prior to Mar. 14, 2011.
Plastics Laser Marking in the Aerospace Industry Article, published by The Sabreen Group, Inc., [online] [retrieved from the Internet Nov. 26, 2007] <URL:www.plasticslasermarking.com/laser_marking_aerospace.htm>.
Printing and Striping Inks Brochure, published by Colorant-Chromatics, printed on Feb. 14, 2011.
Products Brochure, published by Colorant-Chromatics, printed on Feb. 14, 2011.
PTFE & FEP Inks Brochure, published by Standard Technical Applied Resources, Inc., printed on Feb. 14, 2011.
PTFE & PFA Fluoropolymer Labware Brochure, printed from ScienceGear.com on Nov. 6, 2012, available prior to Mar. 14, 2011.
PTFE Marked Tubing Brochure, published by Shanghai Rongyuan Fluorocarbon Products Co., Ltd., printed on Nov. 6, 2012, available prior to Mar. 14, 2011.
Sabreen, Scott R., New Technologies for High-Speed Color Laser Marking of Plastics Article, published by Plastics Decorating Magazine, Oct./Nov. 2004.
Technical Capabilities Brochure, published by Gore, printed on Feb. 14, 2011.
The PTFE Story Brochure, published by Gore, printed on Feb. 14, 2011.
Total solutions for High Contrast & Color Laser Marking Article, Published by The Sabreen Group, Inc., [online] [retrieved from the Internet Nov. 26, 2007] <URL:www.plasticslasermarking.com/metals_laser_marking.htm>.
Total Solutions for High Contrast Laser Marking of Plastics and Metals Substrates Article, published by The Sabreen Group, Inc., [online] [retrieved from the Internet Nov. 26, 2007] <URL:www.plasticslasermarking.com/laser_marking.htm>.
Types of Tubing Brochure, published by ColorTrax, printed on Nov. 6, 2012, available prior to Mar. 14, 2011.
UV40 Dual Care Acrylated Urethane Coating Technical Data Sheet: Chase Specialty Coatings, pp. 1-3, Jul. 2007.

* cited by examiner

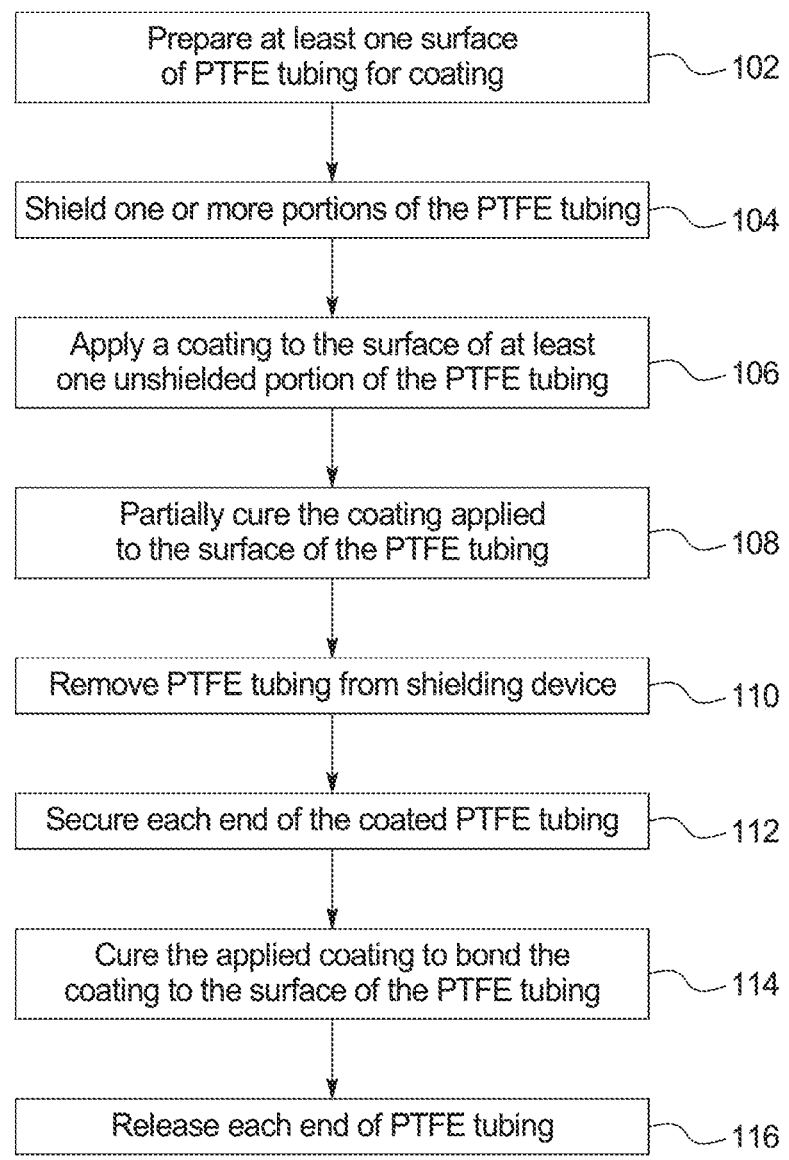

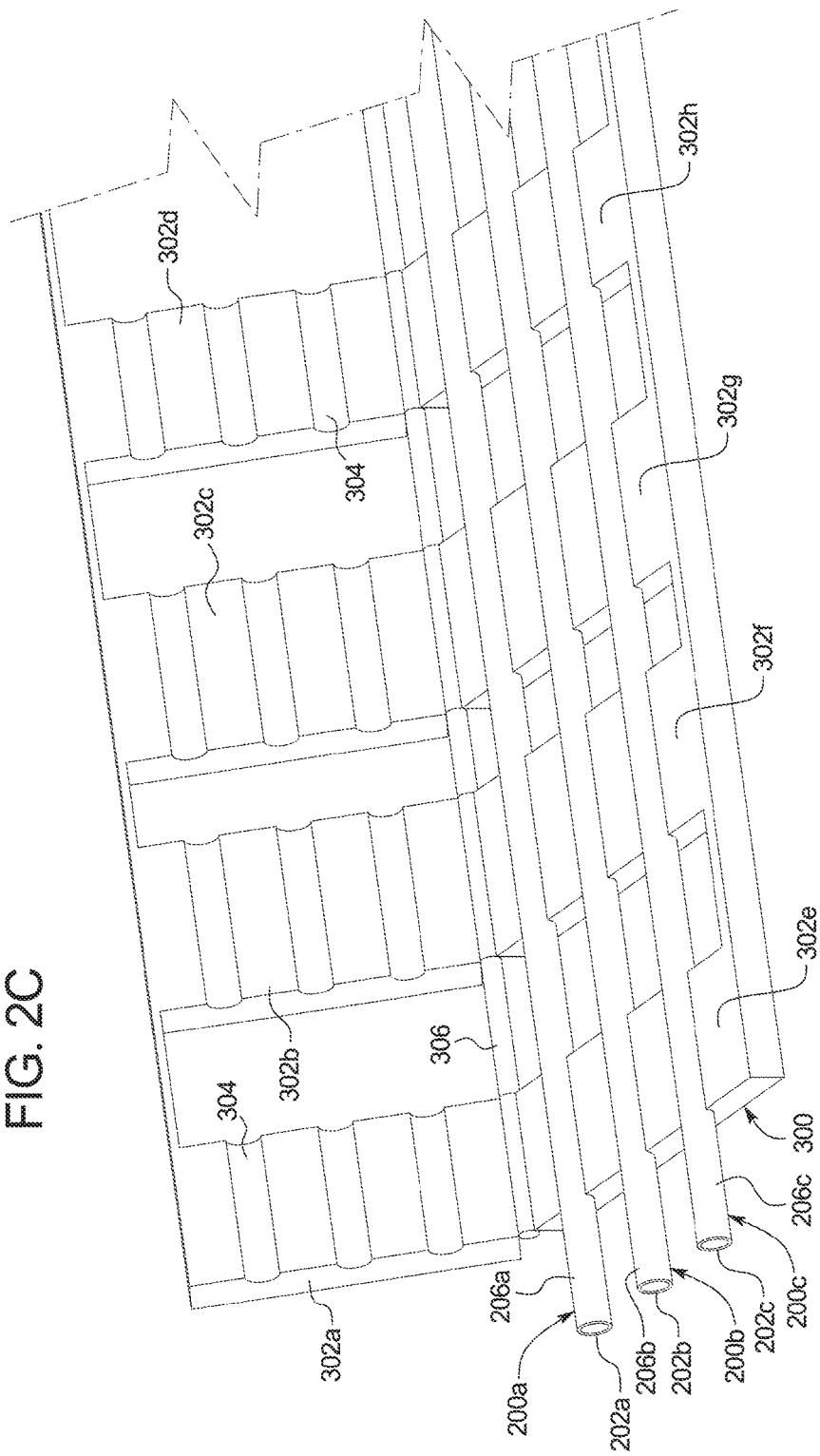

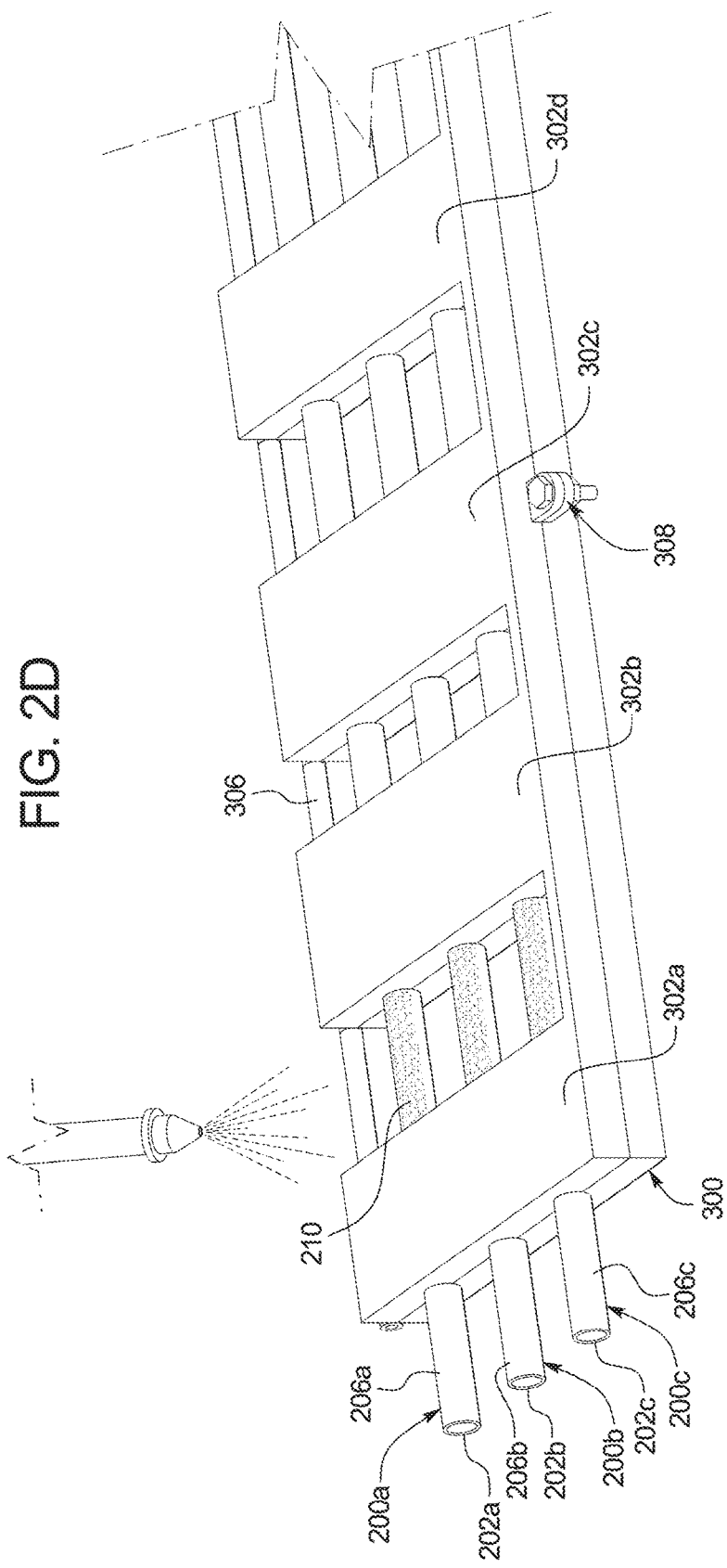

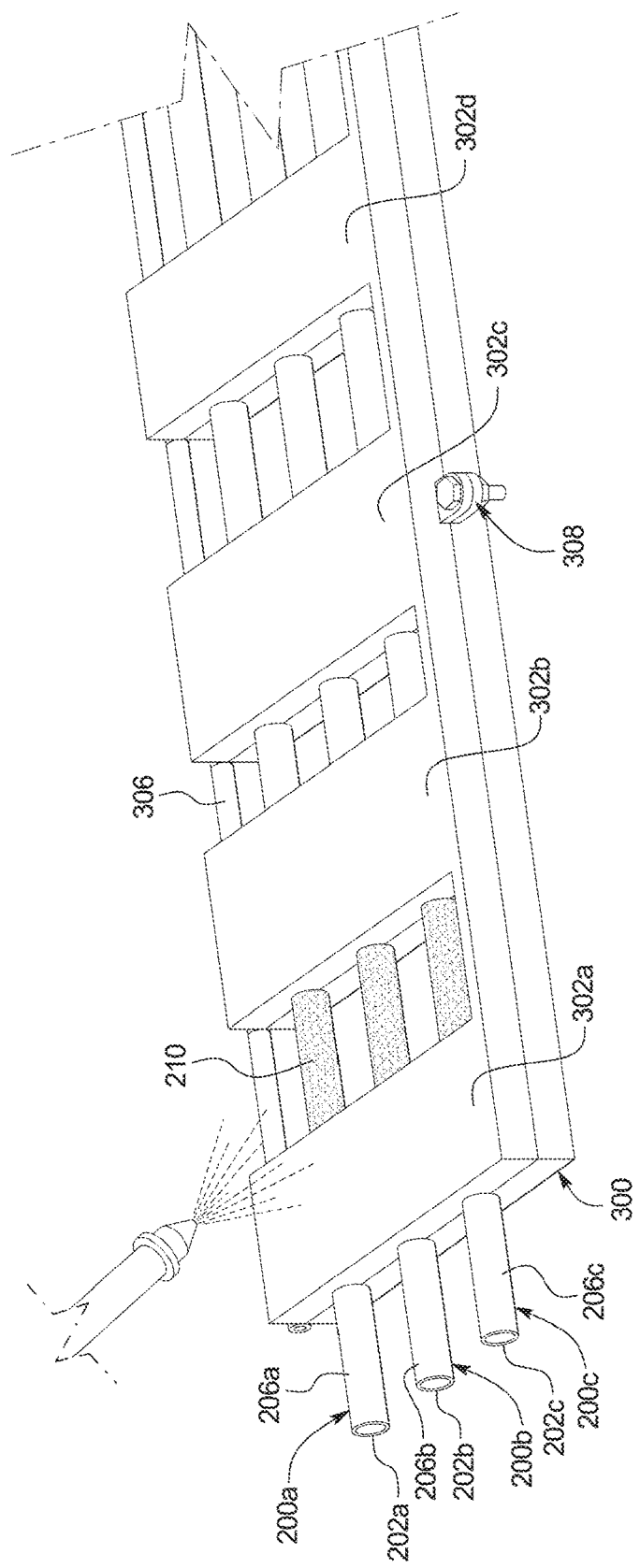

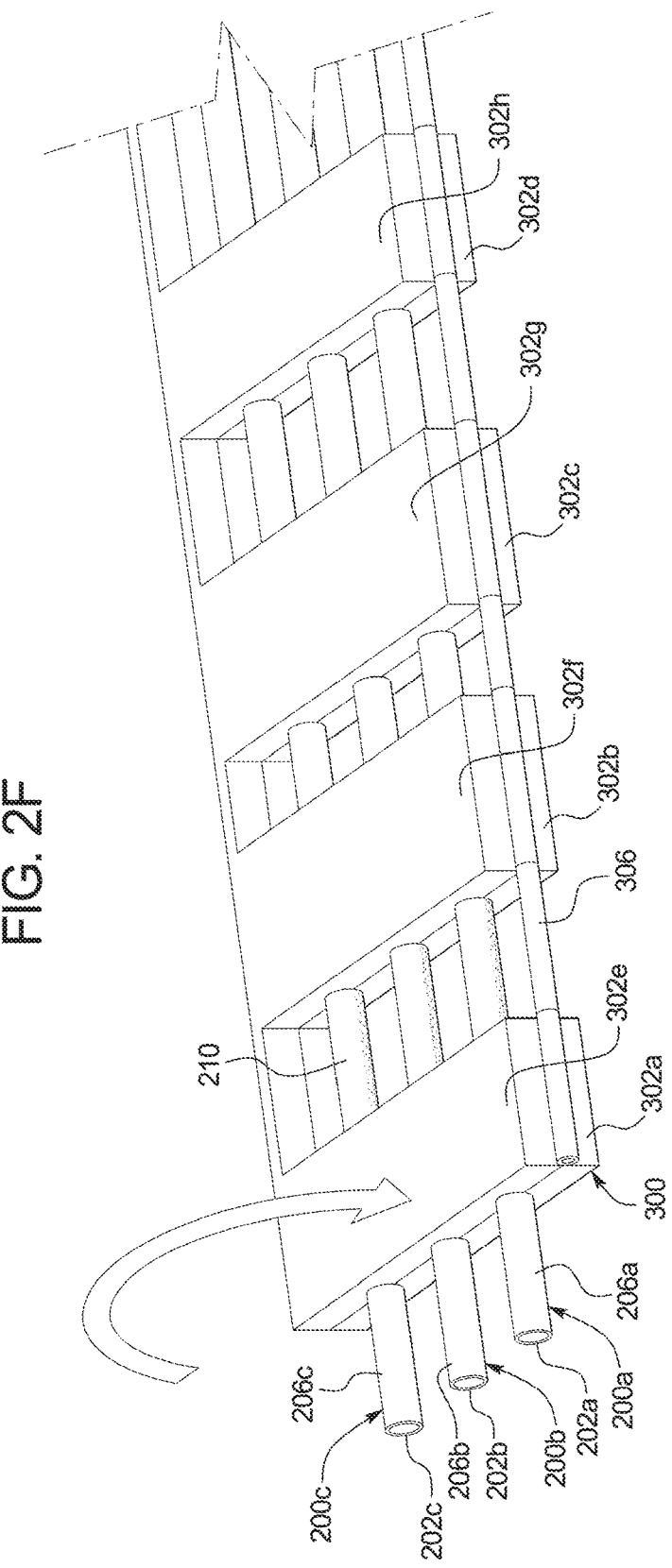

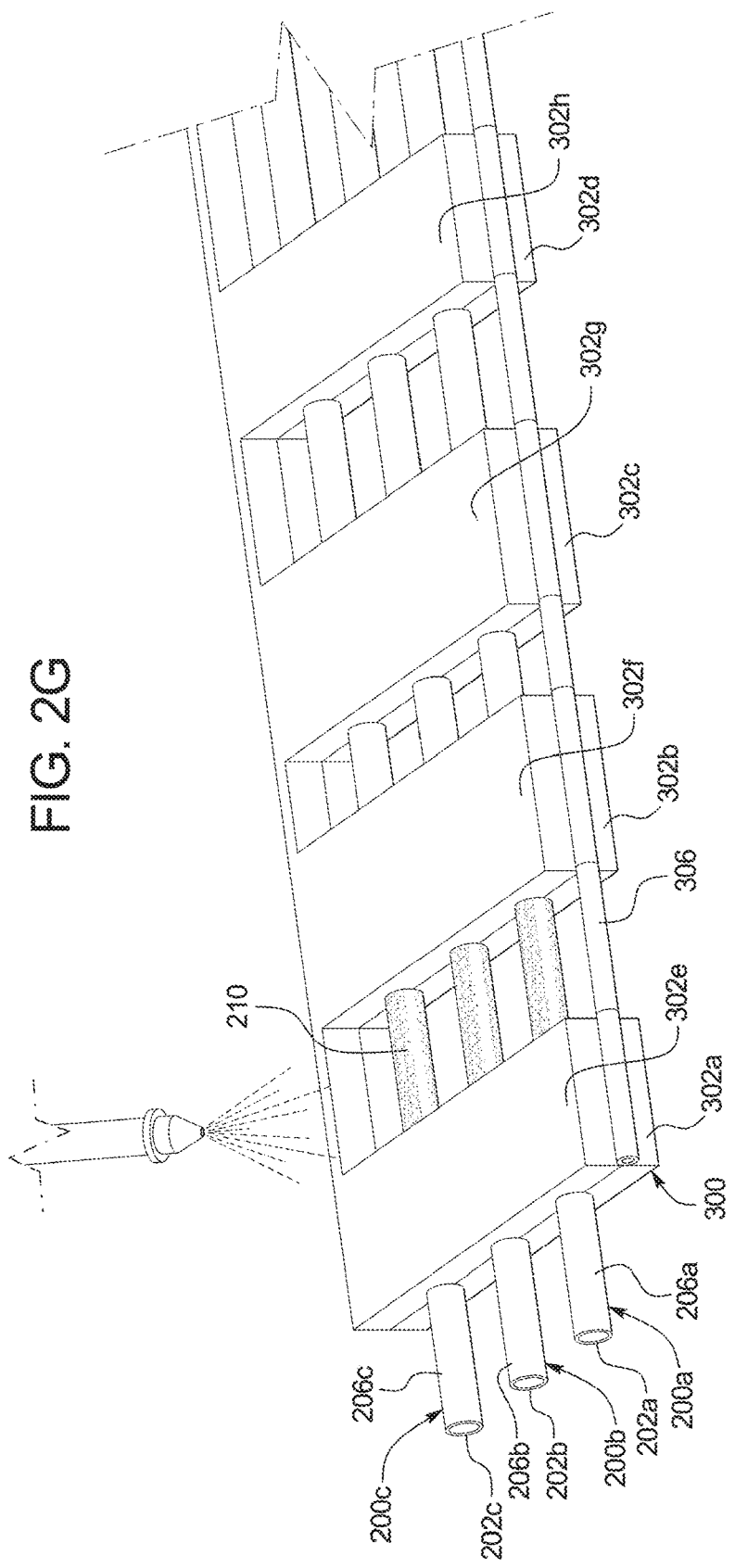

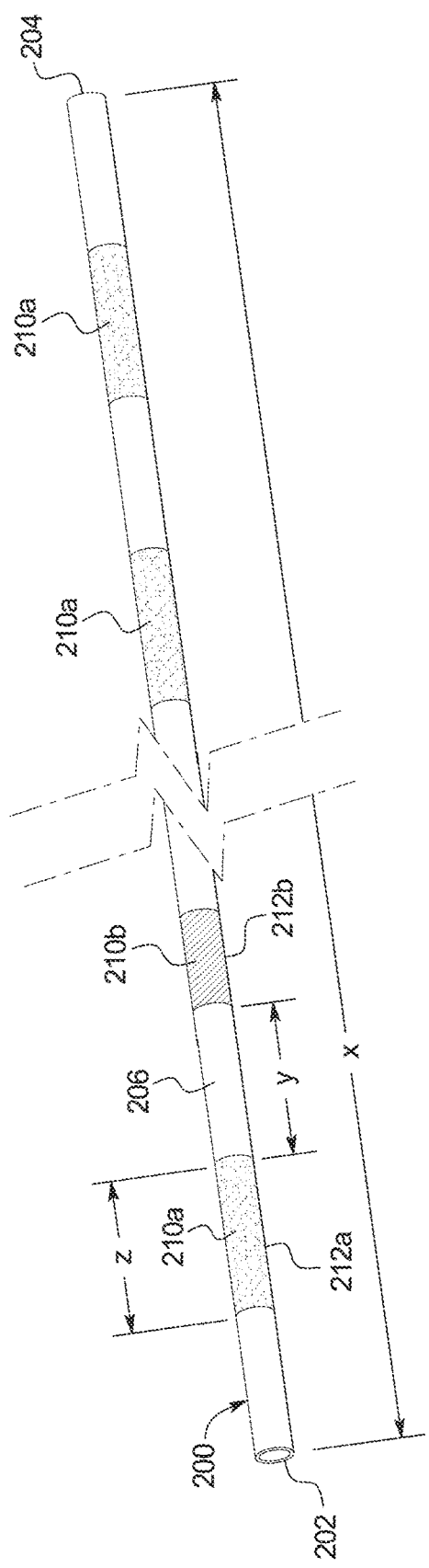

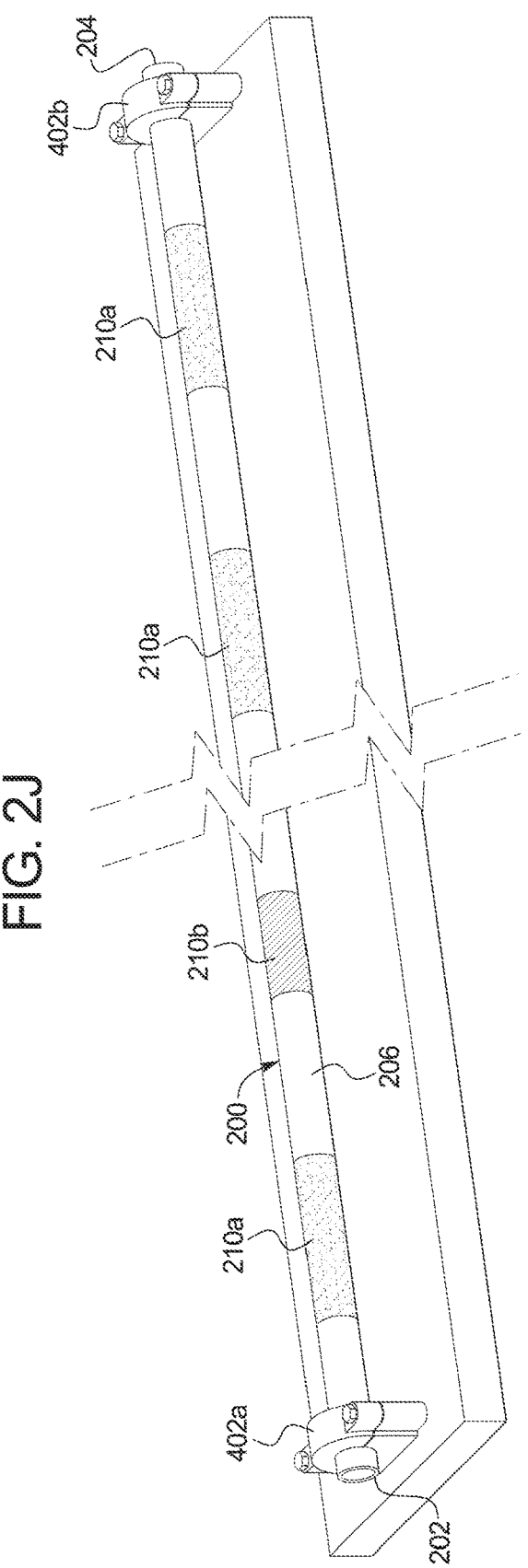

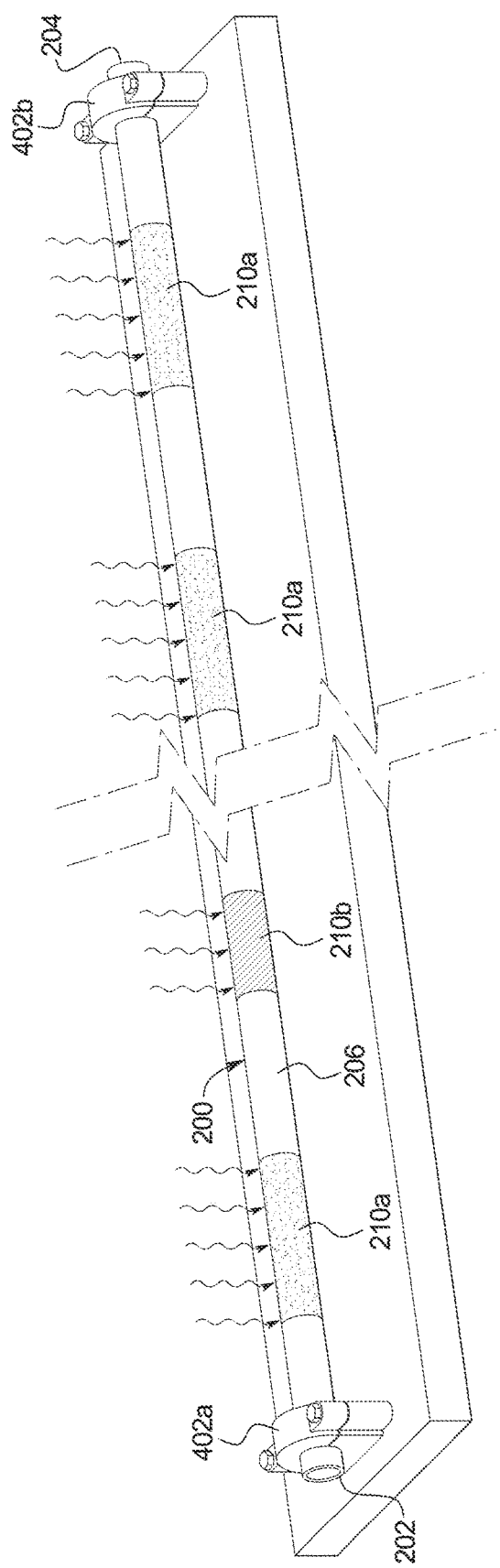

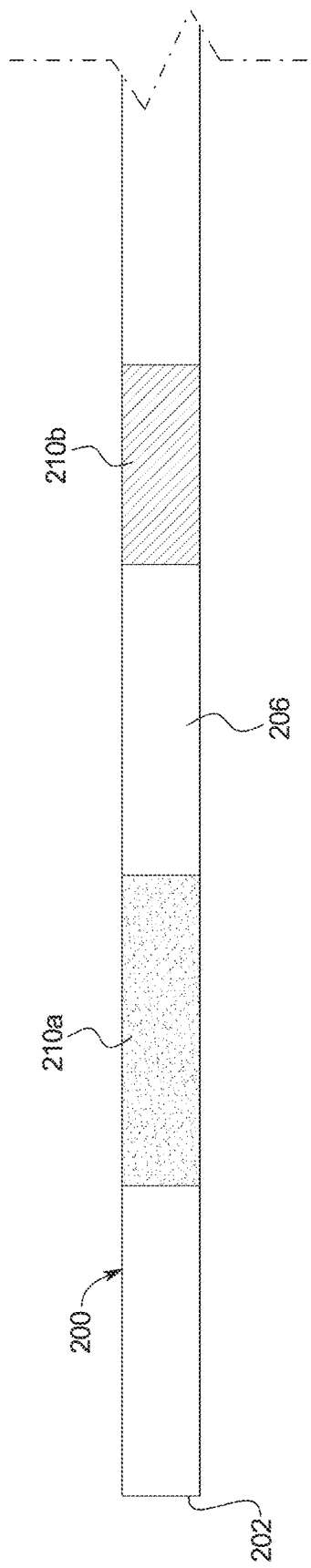

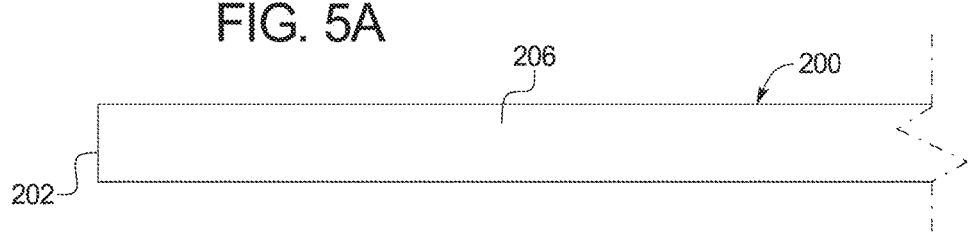
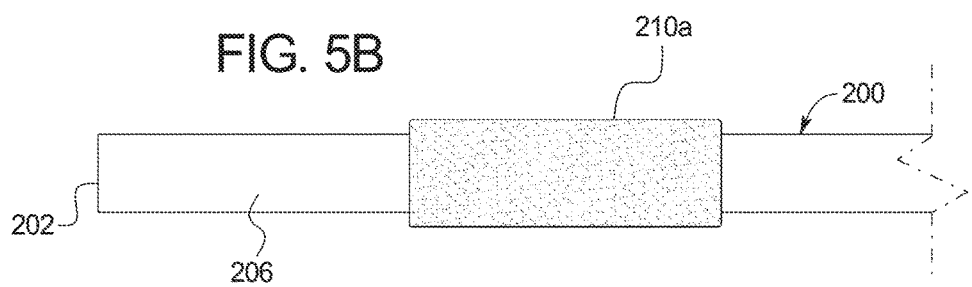
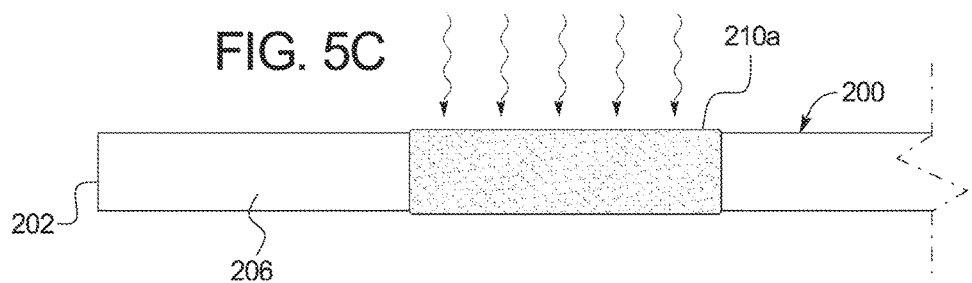
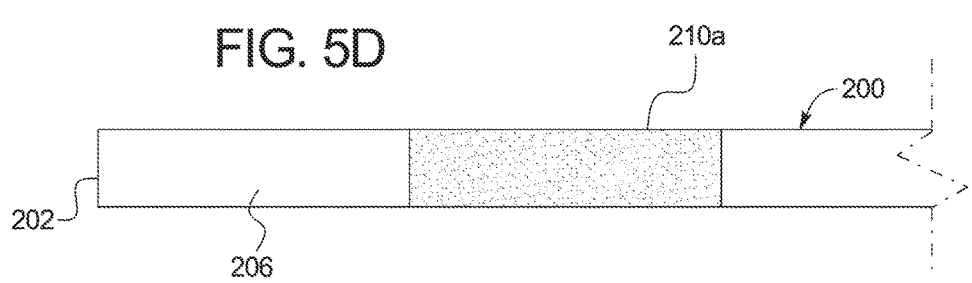

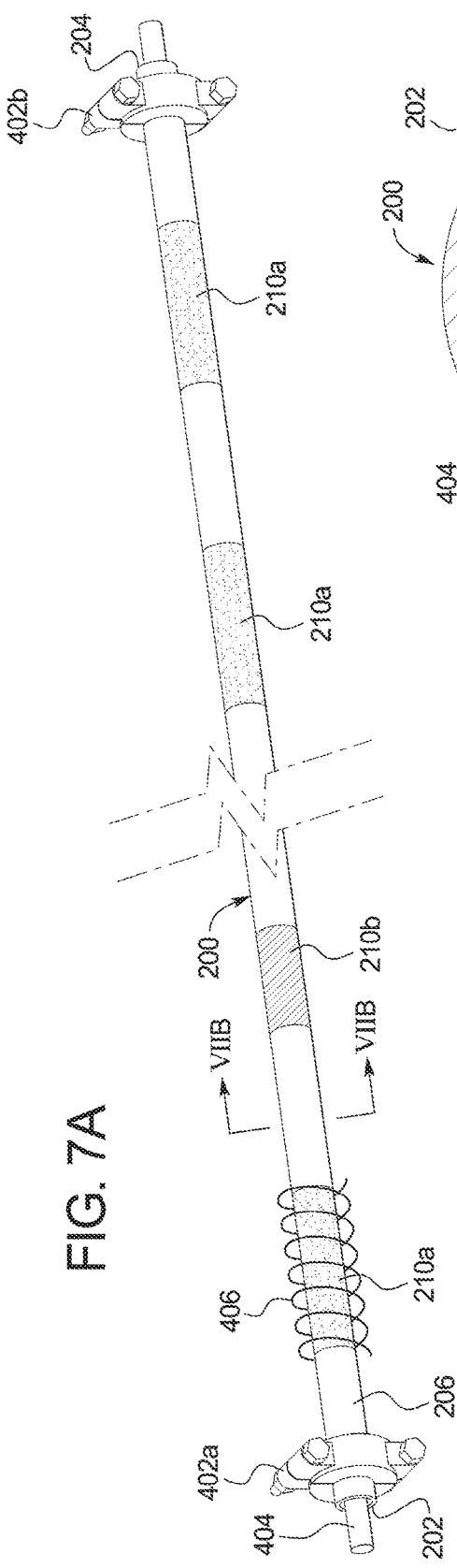

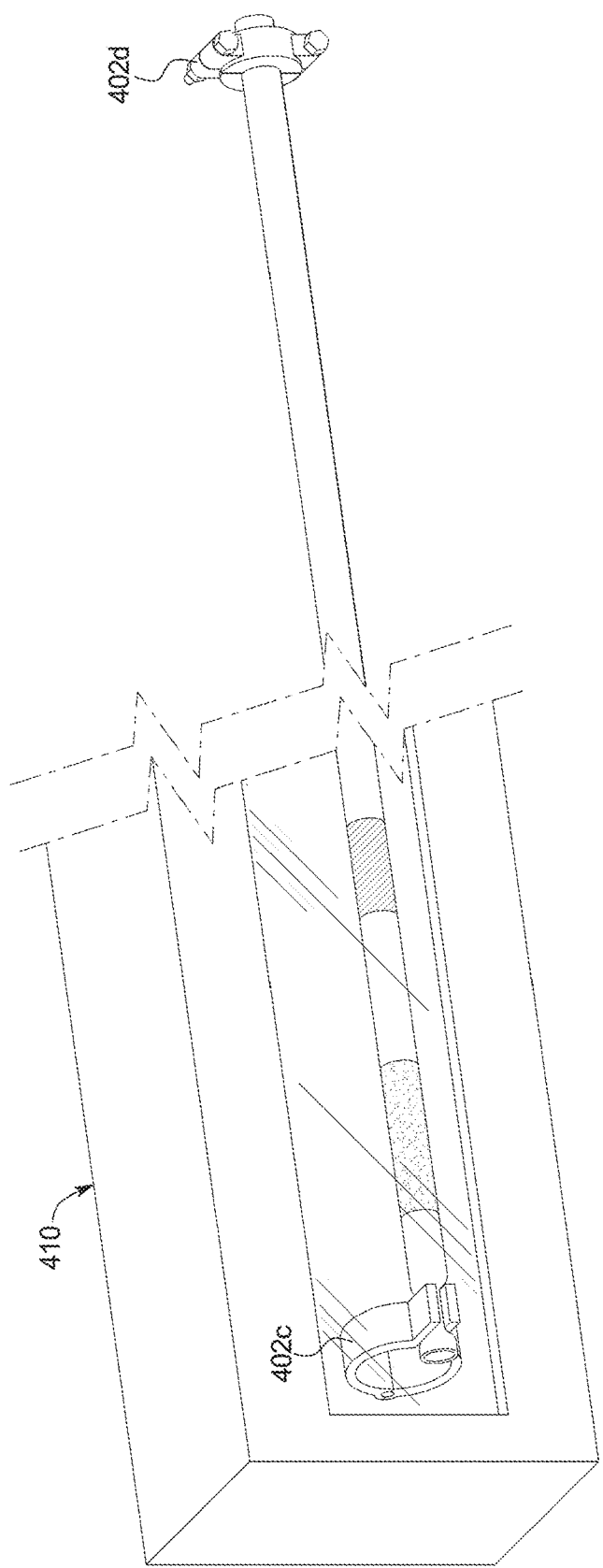

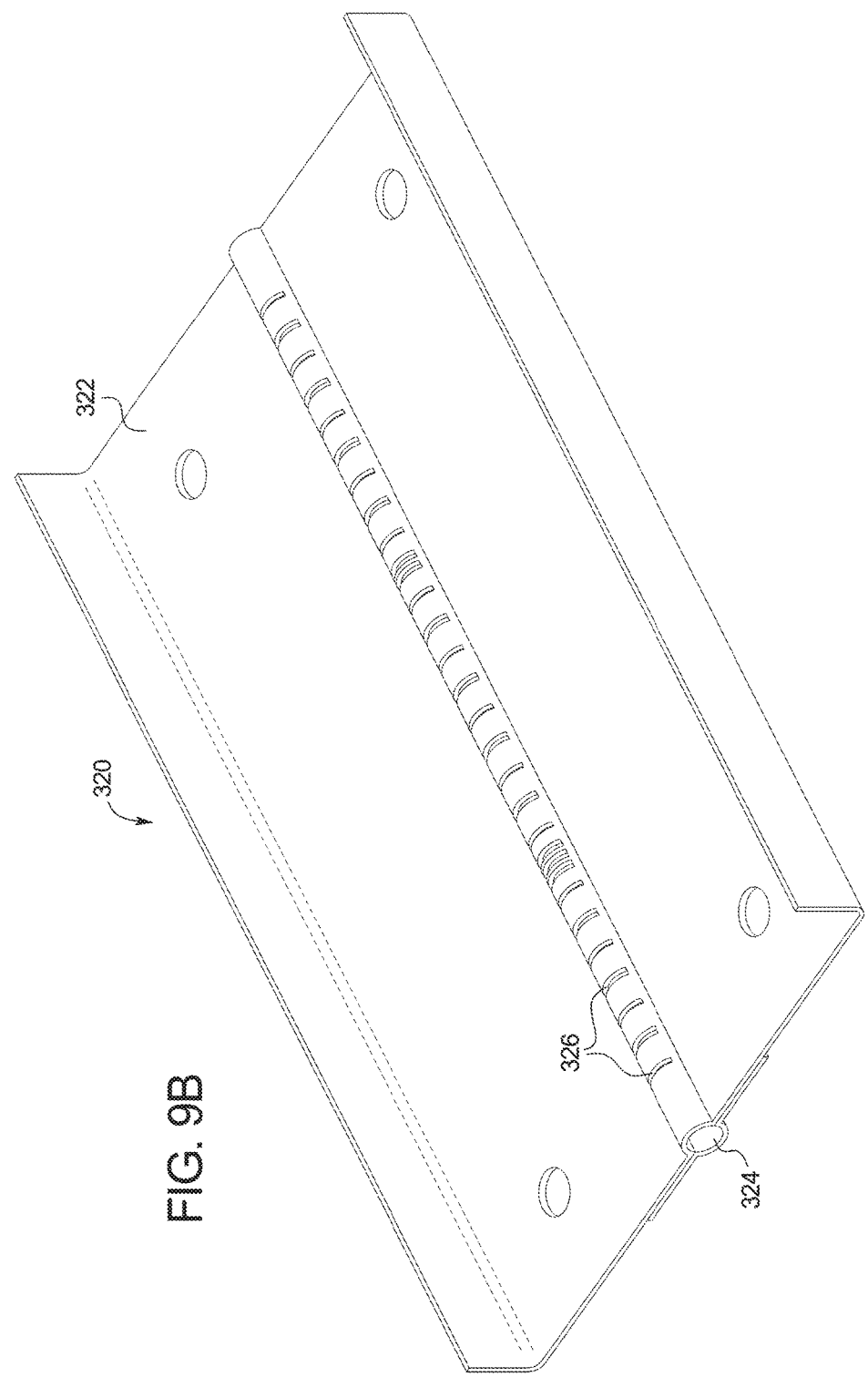

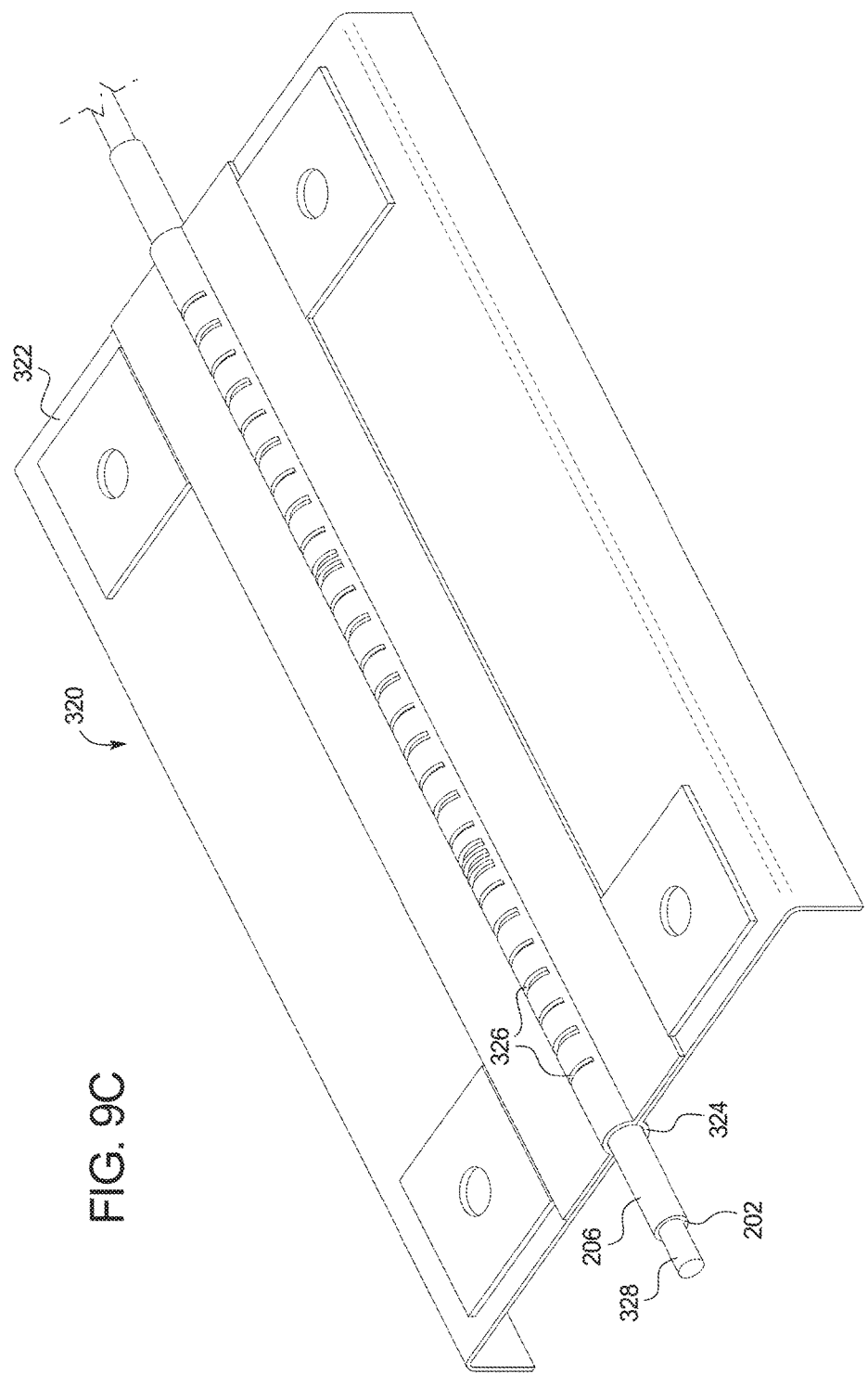

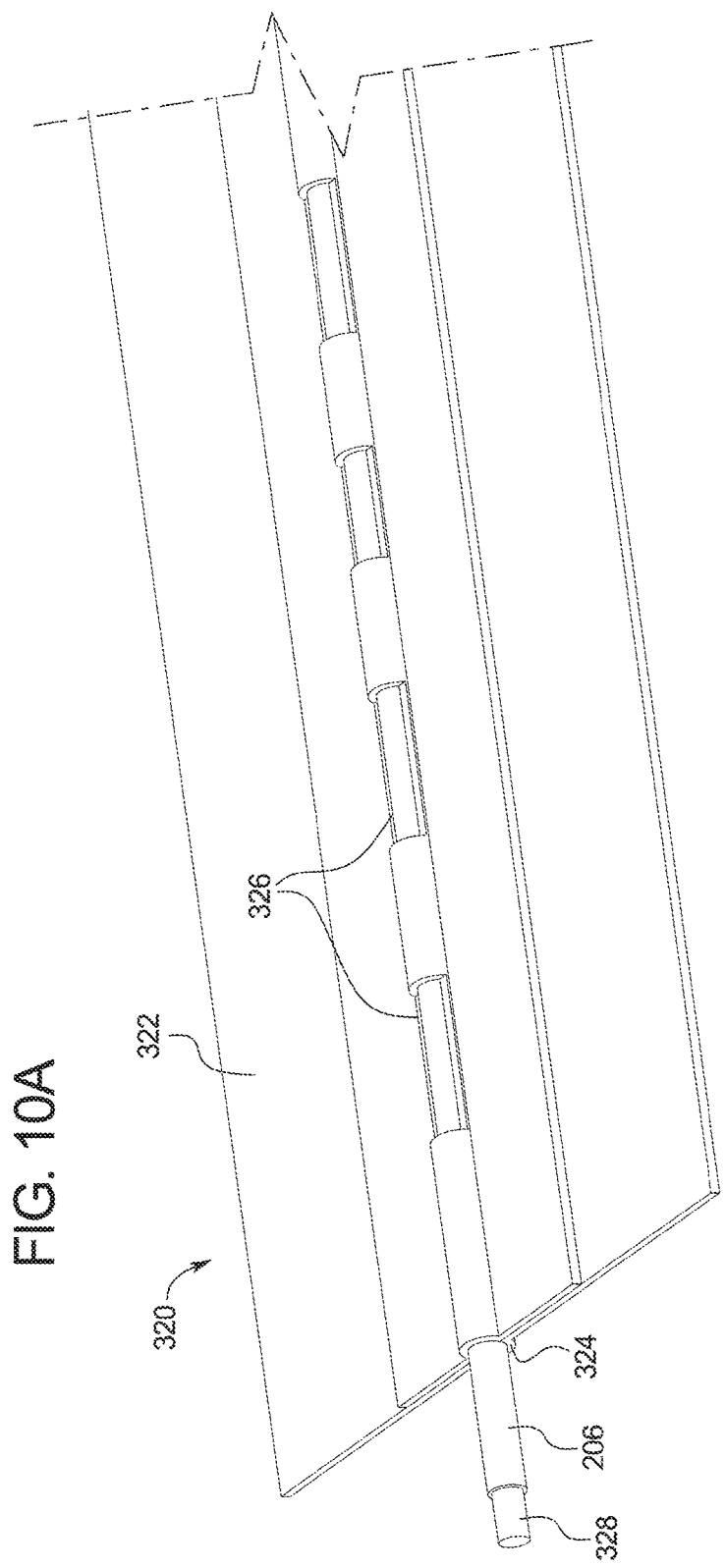

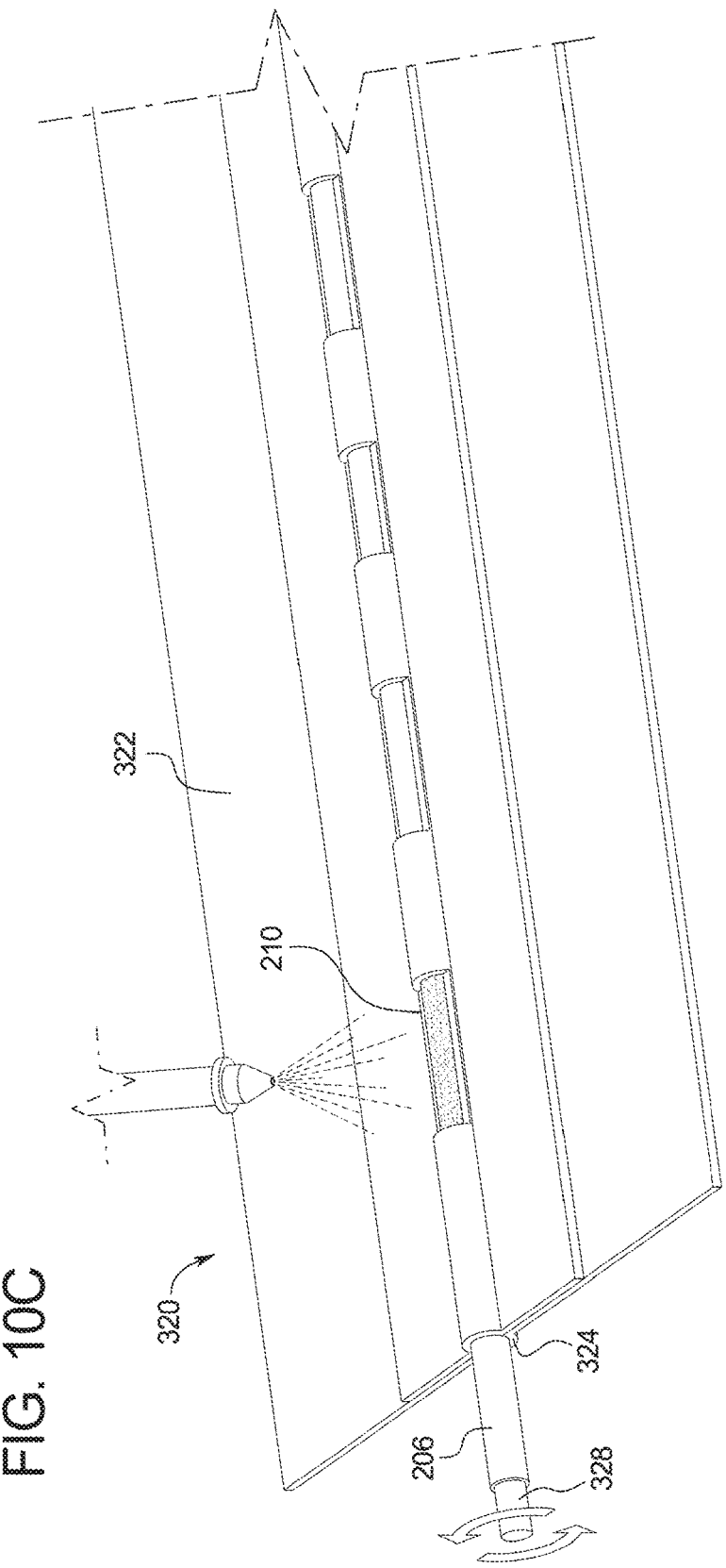

MARKED FLUOROPOLYMER SURFACES AND METHOD OF MANUFACTURING SAME

PRIORITY CLAIM

This application is a continuation of, claims priority to and the benefit of U.S. patent application Ser. No. 15/654,117, filed on Jul. 19, 2017, which is a continuation of, claims priority to and the benefit of U.S. patent application Ser. No. 14/526,099, filed on Oct. 28, 2014, now U.S. Pat. No. 9,744,271, which issued on Aug. 29, 2017, which is a continuation of, claims priority to and the benefit of U.S. patent application Ser. No. 13/416,743, filed on Mar. 9, 2012, now U.S. Pat. No. 8,900,652, which issued on Dec. 2, 2014, which claims priority to and the benefit of U.S. Provisional Patent Application No. 61/452,380, filed on Mar. 14, 2011, the entire contents of which are each incorporated by reference herein.

BACKGROUND

Medical tubing or tubes are commonly inserted into humans or animals for therapeutic and diagnostic medical procedures. Surgeons or other medical professionals must often be able to determine the specific distance that the medical tubing is inserted into a body of a patient. The accurate placement of the medical tubing is usually critical to the procedure. If medical tubing is inserted too far into a patient, it could tear, puncture, or otherwise cause damage to internal bodily tissues, vessels, and/or organs, which could be harmful or potentially fatal to the patient. Alternatively, if not inserted far enough, the procedure may not be successfully performed. Accordingly, certain medical tubing is marked with visual indicia of one or more colors at measured intervals along the length of the medical tubing to indicate to the user the length, orientation, size, or diameter of the medical tubing inserted into a patient. For example, to assist the surgeons or other medical professionals, directional arrows and/or bands of various colors are often marked on a surface of the medical tubing to enable the surgeon to denote orientation of the medical tubing.

One potential problem with such medical tubing is that the markings placed at measured intervals along the length of the medical tubing may be inaccurate. That is, such markings may be slightly misplaced (i.e., are not placed at the exact location along the length of the medical tubing indicated to the medical professional). For example, a marking that is supposed to indicate to a medical professional that a mark is 2.00 inches (or 5.08 centimeters) from a distal end of the medical tubing may be misplaced and actually be 2.10 inches (or 5.33 centimeters) from the distal end of the medical tubing. In the medical industry and specifically in the field of medical tubing that is inserted into a patient's body, such inaccuracies may be harmful or potentially fatal. In other words, when marked medical tubing is inserted into a body, such slight inaccuracies in the placement of the indicated marking may cause the medical tubing to be inserted too far into a patient (which is associated with the above-described risks to the patient) or not far enough into a patient (which is associated with the above-described risks to the patient). Accordingly, accurate placement of markings along the length of medical tubing is critical when such medical tubing is inserted into a patient.

Additionally, certain known medical tubing can "stick" to tissues, catheters, or other surfaces during insertion or extraction. If medical tubing sticks to other surfaces as it is inserted into a body, the surgeon or other medical professional must apply a greater insertion force to the medical tubing to reinitiate movement. Once movement is reinitiated, the opposing force immediately decreases so that the medical tubing is caused to quickly accelerate into or out of the body. Such extreme movements increase the risk of scraping, rubbing, tearing, puncturing, or otherwise damaging a patient's internal tissues due to misplacing the end of the medical tubing in the patient.

To address such issues, certain know medical tubing has been formed from one or more low-friction, low surface energy materials, such as polytetrafluoroethylene (PTFE). This medical tubing, such as solid PTFE tubing, non-solid PTFE tubing, cellular PTFE tubing, porous PTFE tubing, and expanded PTFE tubing (known commonly as e-PTFE), reduces the amount of friction between the medical tubing and bodily tissues, catheters, or other surfaces. Accordingly, such low-friction medical tubing is less likely to stick to other surfaces and therefore gives surgeons or other medical professionals more control over the insertion speed and depth, which reduces the risk of harm to the patient by reducing the above-described "slip-stick" phenomena. Such low-friction medical tubing generally has a smooth very slippery outer surface that will not scrape, irritate, or snag tissues, vessels or arteries. However, because of the extremely low surface energy of the smooth, very slippery low-friction surfaces of such medical tubing, there are very limited methods for securely placing and permanently adhering markings on such low-friction medical tubing, such as PTFE tubing.

One known method of marking low-friction medical tubing and specifically PTFE tubing, is to print or otherwise deposit ink (or paint) on the surface of the low-friction medical tubing and then cure the deposited ink at a cure temperature that does not affect or otherwise degrade the PTFE tubing. For example, for tetrafluoroethylene-hexafluoropropylene (FEP) Striping Ink manufactured by Colorant Chromatics, Colorant Chromatics recommends applying the FEP Striping Ink on a PTFE substrate and curing the applied FEP Striping Ink at 509° F. (265° C.). In another example, for GEM® WB1150 High-Temp Striping Ink manufactured by GEM®, GEM® recommends applying the High-Temp Striping Ink to a PTFE substrate and curing the applied High-Temp Striping Ink at 509° F. (265° C.). In another example, for GEM® WB1140 High-Temp Marking Ink manufactured by GEM®, GEM® recommends applying the High-Temp Marking Ink to a PTFE substrate and curing the applied High-Temp Marking Ink at 509° F. (265° C.).

It should be appreciated that the cure temperature of each of these inks is at or below 550° F. (288° C.) because while PTFE has a melting temperature of 621° F. (327° C.), PTFE begins to decompose or break down as the PTFE is heated to temperatures above 500° F. (260° C.). Such decomposition of the PTFE can generate toxic or noxious gasses and other harmful airborne particles. Specifically, DuPont™ (i.e., a manufacturer of PTFE) expressly warns that PTFE should not exceed 500° F. (260° C.) and that fumes released by PTFE heated above 500° F. (260° C.) can produce symptoms referred to as "polymer fume fever". Accordingly, to avoid the PTFE decomposing and emitting harmful byproducts, known methods of marking PTFE tubing with inks (or paints) expressly require that the inks or paints be cured at a temperature below the temperature which PTFE begins to decompose and possibly emit harmful byproducts.

It should be further appreciated that when PTFE tubing is heated to temperatures above 500° F. (260° C.), not only can the PTFE begin to decompose, but the dimensions of the PTFE tubing can begin to change. That is, the PTFE tubing can warp, distort, contract or otherwise shrink due to such temperatures. This warping of the PTFE tubing may result in the uncured or wet ink (or paint) markings previously placed at correct measured intervals along the length of the PTFE tubing prior to curing to become inaccurate and misplaced (i.e., not placed at the exact location along the length of the PTFE tubing indicated to the medical professional). As described above, for medical tubing that is inserted into a patient's body, such inaccuracies may be harmful or potentially fatal. Accordingly, to avoid these undesired dimensional changes (and potential accompanying inaccuracies in the placement of markings) to PTFE tubing that occur when PTFE tubing is heated to temperatures above 500° F. (260° C.), known methods of marking PTFE tubing with inks (or paints) heat the PTFE tubing below the temperature which PTFE tubing begins to warp or otherwise shrink.

In light of the known problems with heating PTFE to temperatures at or above the temperature which PTFE begins to decompose and warp, known methods of marking PTFE tubing is to print ink or otherwise deposit ink on the surface of the PTFE tubing and then cure the deposited ink to a temperature below the temperature which PTFE begins to decompose and warp. However, one known problem with marking this low-friction medical tubing is that the marked medical tubing (formed from PTFE which is a low-friction, low-surface energy, relatively inert and very slippery material) resists bonding with such inks (or paints). That is, because the bond strength of the ink to the low surface energy PTFE surface is very weak, the slippery surface of this low-friction medical tubing often allows inks printed on this type of medical tubing to easily peel or flake off the tubing (e.g., the ink can generally be scratched off with a human fingernail rubbing the deposited ink). If the ink (or paint) peels or flakes off or dislodges inside a patient's body, such ink (or paint) may harm the patient (as the ink is not as inert as the PTFE tubing). Ink may also rub or peel off before or during use of the medical tubing, thus destroying the usefulness of the markings, and increasing the risk that the medical tubing will be inserted either too deep, or not deep enough (and harm the patient and/or render the medical procedure ineffective).

Furthermore, many types of commercially available medical tubing have a relatively small outer diameter such that even thin layers of ink can significantly increase the measurable total outer diameter of the medical tubing. By significantly increasing the outer diameter of certain marked portions of the medical tubing and not increasing the outer diameter of certain other unmarked portions of the medical tubing, grooves or valleys can be created in the outer surface of the low-friction medical tubing. The shoulders of these bumps or protrusions can have relatively sharp edges which can scrape or irritate bodily tissues, snag vessels or arteries of the patient, or otherwise cause damage and/or trauma to the patient. When inserting medical tubing into delicate areas, such as various organs, the brain and/or the heart, damage caused by even the smallest of such bumps or protrusions can be harmful and potentially fatal for the patient. Additionally, creating different outer diameters along the length of the medical tubing tends to increase the required insertion force and decreases the control a surgeon or other medical professional can exercise over the speed and depth of an insertion. Therefore, such known methods of marking low-friction medical tubing adversely affects the function of the low-friction medical tubing.

Accordingly, a need exists for improved markings on low-friction medical devices, and specifically medical devices made from PTFE and blends of PTFE polymers. More specifically, a need exists for improved markings on solid PTFE medical tubing, non-solid PTFE medical tubing, expanded PTFE medical tubing (known commonly as e-PTFE), porous PTFE medical tubing, and/or cellular PTFE medical tubing. Such a need exists for such low-friction medical tubing with markings that are permanently bonded to the surface of the low-friction medical tubing, that are indelible (i.e., not readily or easily removable by solvents or liquids and relatively abrasion resistant), that are accurately placed on the low-friction medical tubing, that do not significantly increase or decrease the diameter of the low-friction medical tubing (i.e., do not significantly protrude from the surface) and that do not significantly adversely affect the function of the low-friction requirements of medical tubing.

SUMMARY

The present disclosure relates in general to low-friction, low surface energy and/or non-stick medical devices, and specifically to low-friction, low surface energy and/or non-stick medical tubing having visible markings, and a method for manufacturing the same. More specifically, the present disclosure relates to applying a coating to one or more selected portions of a surface of low-friction medical tubing, and simultaneously or substantially simultaneously: (a) curing the applied coating to a designated temperature (which is above the temperature at which the low-friction medical tubing begins to decompose and shrink) to adhere the applied coating to the surface of the low-friction medical tubing, (b) utilizing one or more anti-shrinking devices to counteract or otherwise inhibit the shrinking of the low-friction medical tubing, and (c) exhausting any harmful byproducts resulting from curing the low-friction medical tubing to a temperate above the temperature at which the low-friction medical tubing begins to decompose.

The low-friction medical tubing can be a cylindrical body made from any suitable fluoropolymer, such as any suitable polytetrafluoroethylene (PTFE) including, but not limited to: a solid PTFE, a non-solid PTFE, a porous PTFE, a cellular PTFE or an expanded PTFE (known commonly as e-PTFE), and at least one coating selectively applied to one or more spaced apart selected portions of the outer surface of the body. The body of the medical tubing is generally elongated, has a proximal end, a distal end, an outer surface, and an inner surface which defines one lumen (or a plurality of distinct lumens). The coating includes a binder or bonding material which, when cured at a designated temperature above the decomposition or melting temperature of PTFE, causes the coating to molecularly bond or otherwise adhere to portions or molecules of the outer surface of the low-friction and low-surface energy medical tubing. The coating also includes one or more pigments of a color or hue that contrasts the color of the outer surface of the cylindrical body. Such a configuration facilitates that when the coating is selectively applied to different portions along the length of the low-friction cylindrical body, the medical tubing includes markings which enable a surgeon or other medical professional to determine the length of the medical tubing inserted into a body of a patient by observing the markings on the portion of the medical tubing located exterior to the body of the patient.

In one embodiment, a coating is applied to selected portions the surface of the cylindrical body of the low-friction medical tubing, such as PTFE tubing. In one embodiment, to apply the coating to selected portion of the body, the low-friction body is placed in, attached to or otherwise coupled with a shielding device. The shielding device protects, shields or mask the parts of the outer surface of the body which are not desired to be coated or marked. In one embodiment, the shielding device includes one or more masking members spaced apart along the length of the shielding device. In this embodiment, the spacing of the gaps between masking members corresponds to the markings to be indicated along the length of the cylindrical body of the low-friction medical tubing. It should be appreciated that the shielding device may be configured to correspond with any suitable combination of lengths and patterns to indicate different lengths and locations on the body of the medical tubing.

Once placed in the shielding device, a coating is applied to one or more unprotected, unshielded or unmasked portions of the surface of the body of the low-friction medical tubing (i.e., the coating is applied to selected portions of the surface of the body of the medical tubing). The coating includes a binder such as an epoxy, phenolic, phenoxy, polyimide, polyamide, polyamide-amide, polyphenylene sulfide, polyarylsulfone, polyethylene, polytetrafluoroethylene, fluorinated ethylene propylene, perfluoroalkoxy, tetrafluoroethylene-hexafluoropropylene (FEP), polyetheretherketone (PEEK), polyetherketone (PEK), tetrafluoroethylene perfluoromethyl vinyl ether copolymer (MFA), or any other suitable binder or resin. The coating also includes at least one pigment or a combination of different pigments, such as any suitable organic pigment, inorganic pigment, extender pigment, magnetic receptive pigment and/or laser excitable pigments.

In one embodiment, a plurality of different coatings are respectively applied to a plurality of different unprotected, unshielded or unmasked portions of the surface of the body of the low-friction medical tubing. In this embodiment, the different coatings each include different colored pigments such that after the coatings are applied to different portions of the surface of the body of the low-friction medical tubing, the low-friction medical tubing includes different colored markings.

In other embodiments, depending on the shape of the medical tubing and the configuration of the shielding device, the coating is applied in two or more different or separate steps. For example, because of the cylindrical shape of the body of the medical tubing, the coating is applied to one side of the body of the medical tubing via a plurality of coating applications, then the shielding device (including the attached body of the medical tubing) is rotated and the coating is applied to another side of the body of the medical tubing via another plurality of coating applications.

After applying the coating(s) to the desired portion of the body of the low-friction medical tubing, and drying or semi-curing the applied coating (so the coating is sufficiently dry and physically stable), the coated body of the medical tubing is removed from or decoupled from the shielding device. At this point, the coated body of the medical tubing includes one or more marked codes or patterns which denote distance from the distal end of the body of the medical tubing, the proximal end of the body of the medical tubing, the centerline of the body of the medical tubing or any suitable point or location of the body of the medical tubing required by the medical tubing manufacturer or the medical tubing designer.

After drying or semi-curing the applied coating, as further explained below, the coated medical tubing is placed in, attached to or otherwise coupled with one or more anti-shrinking devices. In one such embodiment, the anti-shrinking device holds the distal and proximal ends of the body of the coated medical tubing stationary or in place (such as by holding each end with a suitable holder or clamp). In another such embodiment, the anti-shrinking device additionally or alternatively includes one or more support members, including solid and/or liquid support members, which are inserted into the lumen(s) of the PTFE tubing. In one embodiment, after securing the coated medical tubing, the body of the coated medical tubing is suitably further or finally cured at a designated temperature, such as 650° F. (343.33° C.) for a designated period of time, such as fifteen minutes. It should be appreciated that the further cure temperature is above the manufacturer's recommended and stated maximum temperature of 500° F. (260° C.) at which PTFE begins to decompose, soften, weaken, distort or otherwise warp. Such a cure temperature provides increased adhesion of the coating to the surface of the PTFE tubing (compared to curing coatings at a temperature at or below the 500° F. (260° C.) at which PTFE begins to decompose and warp). More specifically, by curing the coated PTFE tubing to a designated temperature, such as 650° F. (343.33° C.), both the binder of the coating and the molecules of the PTFE at or near the outer surface of the body of the PTFE tubing melt or begin to fuse together in either a melt flow adhesion process or a sintering process depending on the composition and formulation of the PTFE tubing, and the composition and formulation of the applied pigmented coating. In this embodiment, the melted coating and the melted molecules of the PTFE bond or otherwise adhere to each other to adhere the coating, and specifically the pigments in the coating, to the surface of the body of the PTFE tubing. Accordingly, by curing the PTFE tubing to a temperature above which the PTFE tubing begins to degrade, an increased adhesion of the coating to the surface of the PTFE tubing is achieved (and thus a reduction in the peeling off or dislodging of the coating on the surface of the PTFE tubing is also achieved).

It should be further appreciated that because one or more portions of the PTFE tubing disclosed herein are heated to a temperature above the decomposition temperature of PTFE, the present disclosure provides the cure of the applied coatings in a controlled environment with the appropriate effluent filtration systems, such as appropriate carbon filtration systems, which absorbs harmful byproducts of the decomposition of the PTFE and thus minimizes any exposure to harmful byproducts emitted during the cure of the PTFE tubing. Additionally, because the PTFE only begins to decompose and warp at temperatures above 500° F. (260° C.) and the decomposition of the PTFE is a gradual process, the amount of time the further cure occurs is limited to the designated period of time to facilitate that only the molecules of the PTFE at or near the outer surface of the body of the PTFE tubing begin to melt and the applied coating adheres to the outer surface of the body of the PTFE tubing. Such limits to the amount of time the PTFE is above the recommended maximum use temperature of 500° F. (260° C.) accomplishes that the amount of decomposition and emission of any harmful byproducts, if any, of the PTFE is minimal.

As described above, when PTFE tubing is cured to temperatures above the recommended maximum use temperature of 500° F. (260° C.), the dimensions of the PTFE tubing begin to change. Accordingly, to counteract any shrinking that might occur when the PTFE tubing is further cured at a designated temperature, such as at least 650° F. (343.33° C.) for a designated period of time, one or more anti-shrinking devices are utilized to secure PTFE tubing and inhibit, reduce or prevent such shrinking along the length of the body of the PTFE tubing. That is, as described above, compared to known methods of marking PTFE tubing, a higher cure temperature facilities a stronger bond or adhesion of the coating to the surface of the PTFE tubing, but the higher cure temperature is accompanied by potential warping of the PTFE tubing. Thus, the present disclosure employs the higher cure temperature while simultaneously accounting for or otherwise counteracting, limiting or preventing this potential shrinking of the length (and/or diameter) of the PTFE tubing.

More specifically, for certain low-friction medical tubing, such as the example PTFE tubing described herein, because: (i) the body of the PTFE tubing contracts or shrinks when the PTFE tubing is cured or heated to a temperature, such as at least 650° F. (343.33° C.), (ii) the shielding device includes gaps between the masking members (which are spaced apart at measured intervals along the length of the shielding device), and (iii) these gaps correspond with the exact locations of the intended markings to be placed at measured intervals along the length of the body of the PTFE tubing, to ensure that the markings on the fully cured PTFE tubing correspond with the locations of the intended markings on the finished PTFE tubing, one or more anti-shrinking devices are employed. In one such embodiment, the anti-shrinking device includes one or more clamps or holders which secure or otherwise hold stationary the ends of the body of the PTFE tubing during the further cure. In another such embodiment, the anti-shrinking device includes a support member which is inserted into the lumen (or into one or more of the plurality of lumens) of the PTFE tubing to secure or otherwise hold the body of the PTFE tubing stationary during the further cure. In different such embodiments, this supporting procedure includes a liquid anti-shrinking device, a gas anti-shrinking device and/or a solid anti-shrinking device. In different such embodiments, this supporting procedure includes a two-dimensional anti-shrinking device and/or a three-dimensional anti-shrinking device. In these embodiments, such securing of body of the PTFE tubing thus prevents, limits or reduces the contracting or shrinkage of the length of the body of the PTFE tubing when heated to a temperature such as at least 650° F. (343.33° C.) and also accomplishes that, after the further or final cure, the actual markings along the length of the body of the PTFE tubing will still accurately correspond to the intended markings placed at measured intervals along the length of the body of the PTFE tubing. Providing such accurate markings along the length of the body of the PTFE tubing enables the surgeon or other medical professional to insert the marked PTFE tubing into a patient at the proper position or depth and facilitates a verification to the surgeon or other medical professional that the marked PTFE tubing is inserted into the patient at the proper position or depth. Such accurate placement of the markings benefits patients by reducing the chance that a medical professional will rely on inaccurate markings when inserting the PTFE tubing into the patient (and potentially reduce the chance that the patient will be harmed by any reliance on inaccurately placed markings).

After the further or final cure, the resulting coated low-friction medical tubing includes areas of contrasting color along the length of the medical tubing which results in specific length markings at measured intervals. The markings of such width, depth or distance of the resulting medical tubing enables surgeons or other medical professionals to determine, based on a predetermined pattern known to the device user, the length or depth of the medical tubing inserted into a patient, whether from the proximal or distal end. It should be appreciated that the markings disclosed herein are not limited to indicating lengths, but also can indicate one or more of: a size of the medical tubing, a type of the medical tubing, a material of the medical tubing, a part number of the medical tubing, a serial number of the medical tubing, a lot number of the medical tubing, a manufacturing date of the medical tubing, a manufacturer of the medical tubing, at least one property or instruction associated with the medical tubing, at least one warning, at least one directional arrow, at least one location arrow, at least one bar code or other code, at least one band or stripe along the entire length or along selected lengths from the distal end to the proximal end of the medical tubing, a stripe applied to the outer diameter either in a longitudinal manner or a spiral manner around and along a specified or the entire length of the diameter of the medical tubing, at least one linear line, at least one band or stripe along the longitudinal axis of the medical tubing, at least one spiral patterned line, band or stripe along the length of the medical tubing, a plurality of parallel lines, bands or stripes, a plurality of perpendicular lines, bands or stripes, a plurality of transverse lines, bands or stripes, or any combination thereof.

In one embodiment, the coated portions of the body of the low-friction medical tubing are exposed to temperatures higher than the temperatures that will deform the low-friction tubing (i.e., 500° F. (260° C.)) and the uncoated portions of the body of the low-friction medical tubing are not subjected to such high temperatures. Such selective curing of certain portions of the body of the low-friction medical tubing (i.e., the coated portions) and selectively not curing certain other portions of the body of the low-friction medical tubing (i.e., the uncoated portions) causes the binder of the coating to bond or otherwise bind with the surface of the body of the low-friction medical tubing and the coated portions of the body of the medical tubing to be a different color than the color of the uncoated, uncured portions of the body of the medical tubing. It should be appreciated that such selectively heating of certain portions of the PTFE tubing prevents the decomposition along the entire length of the body of the PTFE tubing and rather provides for the selective decomposition of certain portions along the length of the PTFE tubing.

In one embodiment, in addition to compensating or accounting for any dimensional changes (i.e., any shrinking or contracting) along the length of the body of the low-friction medical device, such as the PTFE tubing, any dimensional changes occurring to the diameter of the body of the low-friction medical device are also compensated or accounted for. Specifically, in this embodiment, since heating or curing of the PTFE to a temperature of at least 650° F. (343.33° C.) causes the body of the PTFE tubing to contract or shrink, curing the coated portions of the body of the PTFE tubing (while not heating or limiting heat to the uncoated portions of the body of the PTFE tubing) causes the diameter of the body of the PTFE tubing at these coated, cured portions to contract or shrink. In one such embodiment, the thickness or amount of the coating applied to these portions of the PTFE tubing is configured to compensate for the reduction in the diameter at these coated, cured portions of the PTFE tubing. Such application of an amount of coating which equals or substantially equals the amount the outer diameter of the body of the PTFE tubing is reduced facilitates that the uncoated portions of the resulting PTFE tubing will have the same or substantially the same outer diameter as the coated portions of the resulting PTFE tubing. Such equal outer diameters reduces or prevents grooves or valleys or bumps or protrusions from being created in the surface of the marked PTFE tubing. That is, by accounting for the subsequent reduction in the outer diameter of the PTFE tubing when determining an amount of coating to apply to certain portions of the PTFE tubing, less bumps or protrusions having shoulders with sharp edges (which can scrape or irritate bodily tissues, snag vessels or arteries of the patient, or otherwise cause damage and/or trauma to the patient) are created in marking the PTFE tubing disclosed herein.

It should be appreciated that while the low-friction medical device disclosed herein is often referred to and illustrated as medical tubing or PTFE tubing, the present disclosure of applying a coating to one or more selected portions of a surface of low-friction medical device, and simultaneously or substantially simultaneously: (a) curing the applied coating to a designated temperature (which is above the temperature at which the low-friction medical device begins to decompose and shrink) to adhere the applied coating to the surface of the low-friction medical device, (b) utilizing one or more anti-shrinking devices to counteract or otherwise inhibit the shrinking of the low-friction medical device, and (c) exhausting any harmful byproducts resulting from curing the low-friction medical device to a temperate above the temperature at which the low-friction medical device begins to decompose; may be employed with any suitable low-friction device that is inserted into a patient or connects to a low-friction device that inserts a device into a patient in connection with any medical procedure and/or any suitable low-friction device that is employed or utilized outside of the medical field. Such suitable low-friction medical devices and such suitable low-friction non-medical devices include, but are not limited to: medical tubes, medical wires, medical tapes, medical guide wires, catheters, needles, soft tissue needles, biopsy devices, biopsy tubular sampling devices, soft tissue biopsy devices, soft tissue tubular devices, hook-type biopsy devices, laminates, vents, medical patches, cannulas, probes, electrosurgical electrodes, sheets, gaskets, blades, knives and any suitable low friction, low surface area medical device which flexes, bends or is required to move in any suitable direction. Such suitable low-friction non-medical devices include, but are not limited to: sight tubes, air meters, gas meters, flow meters, labware, containers, plates, sleeves, molded devices, vessels, and any suitable low friction, low surface area non-medical device. Moreover, in different embodiments, the low-friction medical device and/or low-friction non-medical device is constructed from any suitable low-friction and/or low surface energy material, including but not limited to: solid PTFE, non-solid PTFE, expanded PTFE, porous PTFE, micro-porous PTFE, cellular PTFE, fluorinated ethylene propylene (FEP), polyethylene (PE), perfluoroalkoxy (PFA) and/or any low surface energy particulate material.

It is therefore an advantage of the low-friction medical device and method disclosed herein to provide a marked low-friction medical device having markings which do not affect the function or form of the low-friction medical device and which enable a surgeon or other medical professional to determine the length of a medical device inserted into a patient's body, and to control the speed and consistency of the tactile feel at which the medical device is being inserted or extracted from the patient's body. Such medical device does not require special handling that may be required to prevent any non-adhered or non-bonded markings from being dislodged during a medical procedure or during a cleaning procedure. The medical device and method disclosed herein further provides a marked medical device with a smooth, continuous low-friction surface with a substantially constant diameter which reduces occurrences of or otherwise prevents the medical device from snagging, sticking, tearing, or otherwise damaging or irritating vessels, arteries, or other tissues of a patient during insertion, positioning, and extraction of the medical device. That is, the marked low-friction medical device disclosed herein assists a surgeon or other medical professional in smoothly, easily, accurately, and safely inserting and positioning the medical device in a patient's body during a medical procedure with a more consistent tactile "feel" (compared to a marked medical device with protrusions due to the thickness of an added layer of pigmented marking) and know what amount of the medical device is inserted into the patient's body and what amount of the medical device remains outside of the patient's body. In other words, the marked low-friction medical device disclosed herein, such as the solid PTFE medical device, the non-solid PTFE medical device, the expanded PTFE medical device, the porous PTFE medical device, and the cellular PTFE medical device, disclosed herein each include markings that are permanently bonded to the surface of the low-friction medical device, are configured to flex or bend and remain adhered to (i.e., not become dislodged from) the PTFE medical device when the PTFE medical device flexes or bends when inserted into a patient, that are indelible (i.e., not readily or easily removable by solvents or liquids and relatively abrasion resistant), that are accurately placed on the low-friction medical device, that do not significantly increase or decrease the diameter of the low-friction medical device (i.e., do not significantly protrude from the surface) and that do not significantly adversely affect the function of the low-friction medical device.

Additional features and advantages are described herein, and will be apparent from, the following Detailed Description and the Figures.

BRIEF DESCRIPTION OF THE FIGURES

FIG. 1 is a flow chart generally illustrating one embodiment of the disclosed method of marking PTFE tubing.

FIG. 2C is a fragmentary perspective view of a plurality of the PTFE tubes of FIG. 2A being positioned in an example shielding device.

FIG. 2D is a fragmentary perspective view of the PTFE tubes of FIG. 2C being coated from a first direction to selectively coat portions of the surfaces of each of the PTFE tubes.

FIG. 2E is a fragmentary perspective view of the PTFE tubes of FIG. 2D being coated from a second, different direction to selectively coat portions of the surfaces of each of the PTFE tubes.

FIG. 2F is a fragmentary perspective view of the PTFE tubes and the shielding device of FIG. 2E being rotated.

FIG. 2G is a fragmentary perspective view of the PTFE tubes of FIG. 2F being coated from the first direction to selectively coat portions of the surfaces of each of the PTFE tubes.

FIG. 2I is a fragmentary perspective view of one of the coated, partially cured PTFE tubes of FIG. 2H removed from the example shielding device.

FIG. 2J is a fragmentary perspective view of the coated, partially cured PTFE tubing of FIG. 2I being secured at each end by anti-shrinking devices.

FIG. 2K is a fragmentary perspective view of the coated PTFE tubing of FIG. 2J being selectively cured while each end is secured.

FIG. 2L is a fragmentary side view of the cured, coated PTFE tubing of FIG. 2K.

FIG. 5A is a fragmentary side view of the uncoated, uncured PTFE tubing disclosed herein.

FIG. 5B is a fragmentary side view of the coated, uncured PTFE tubing of FIG. 5A.

FIG. 5C is a fragmentary side view of the coated, partially cured PTFE tubing of FIG. 5D.

FIG. 5D is a fragmentary side view of the coated, further cured PTFE tubing of FIG. 5C.

FIG. 7A is a fragmentary perspective view of an alternative embodiment generally illustrating a magnetic induction coil for selectively heating portions of coated PTFE tubing.

FIG. 7B is a cross-sectional view, taken substantially along line VIIB of FIG. 7A, illustrating the diameter of the coated, uncured PTFE tubing of FIG. 7A.

FIG. 8 is a fragmentary perspective view of an alternative embodiment of one of the coated PTFE tubes disclosed herein being cured in a curing device.

FIG. 9B is a fragmentary bottom perspective view of the example shielding device of FIG. 9A.

FIG. 9C is a fragmentary top perspective view of the example shielding device of FIG. 9A coupled with a PTFE tube.

FIG. 10A is a fragmentary perspective view of a PTFE tube being positioned in an example shielding device.

FIG. 10C is a fragmentary perspective view of the PTFE tube of FIG. 10B being coated from a first direction to selectively coat a first portion of the surface of the PTFE tube.

DETAILED DESCRIPTION

Figure 2A:
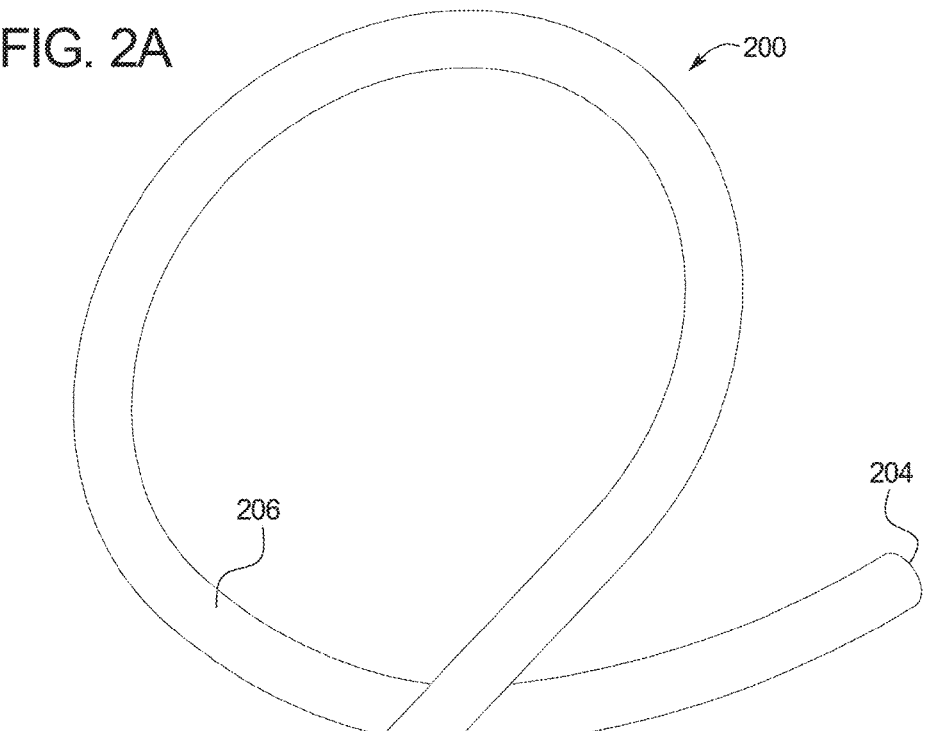
FIG. 2A is a fragmentary perspective view generally illustrating uncoated PTFE tubing.
Figure 2B:
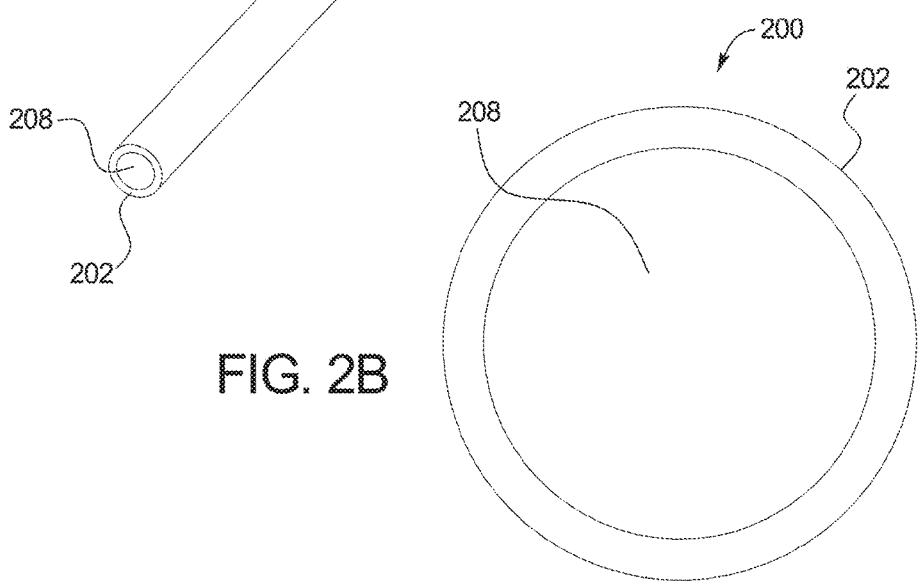
FIG. 2B is an end view of the uncoated PTFE tubing of FIG. 2A.

Referring now to the example embodiments of the present disclosure illustrated in FIGS. 1 to 8, the medical tubing illustrated in FIGS. 2A and 2B is seen before having any coating applied thereto. In this illustrated embodiment, the low-friction medical tubing includes a cylindrical body 200 made from a fluoropolymer, such as polytetrafluoroethylene (PTFE) (which includes a solid PTFE, a non-solid PTFE, a cellular PTFE, a porous PTFE, or an expanded PTFE). The body 200 of the medical tubing is generally elongated, has a proximal end 202, a distal end 204, an outer surface 206, and an inner surface which defines a lumen 208. Since the PTFE tubing is constructed from the low-friction material of PTFE, such tubing includes the properties of high lubricity, high temperature use, high chemical resistance, and biocompatibility. The outer surface 206 is very slippery and more particularly has a very low friction measurement or coefficient of friction measured at 0.10.

In one embodiment, before applying a coating to the surface of the body of the PTFE tubing, the PTFE tubing is prepared for coating as indicated in block 102 of FIG. 1. In one such embodiment, the body of the PTFE tubing is cleaned with a cleaner to remove impurities which are present on the surface of the PTFE tubing. Impurities such as oils may impede bonding of a coating to the outer surface of the body of PTFE tubing, and also may cause damage to a patient if inserted into a patient's body during a medical procedure. The cleaner, such as a solvent, acid solution or alkaline, is suitably applied, such as manually applied, mechanically applied or ultrasonically applied to the PTFE tubing. In another such embodiment, thermal heat, such as heat from a flame, open flame, infrared heat or hot air, is selectively applied to the PTFE tubing to clean the PTFE tubing prior to applying the coating. It should be appreciated that any suitable cleaning method or any suitable combination of cleaning methods may be used to clean the PTFE tubing prior to applying the coating.

After cleaning the outer diameter of the body of the PTFE tubing, one or more parts of the body of the PTFE tubing not desired to be coated are blocked or shielded as indicated in block 104 of FIG. 1. As described below, such blocking, protecting, shielding or otherwise suitably masking of one or more parts of the body of the PTFE tubing enables that certain parts or portions of the PTFE tubing are coated and certain other parts or portions of the body of the PTFE tubing are not coated (as further discussed and illustrated below).

In one embodiment, one or more PTFE tubes are placed in, attached to or otherwise coupled with a suitable shielding device. In one embodiment, as seen in FIG. 2C, to enable a plurality of PTFE tubes to be simultaneously coated, a plurality of PTFE tubes 200a, 200b and 200c are simultaneously positioned in the shielding device.

In the illustrated embodiment of FIG. 2C, to protect or mask one or more parts of the PTFE tubing, a shielding device 300 is utilized. Shielding device 300 includes one or more masking members 302a, 302b, 302c, 302d, 302e, 302f, 302g and 302h. Each masking member includes or defines a plurality of grooves 304 to receive a portion of a PTFE tube. Each masking member is attached to a hinge 306 which enables rotation of the masking members. Such rotation enables masking members 302a and 302e, masking members 302b and 302d, masking members 302c and 302g, and masking members 302d and 302h to each be moved toward each other to engage the PTFE tubing in a closed position (as seen in FIG. 2D) and away from each other to disengage the PTFE tubing in an open position (as seen in FIG. 2C). This example shielding device includes one or more locking devices 308, such as fasteners connected to certain of the masking members, to lock the shielding device in the closed position. It should be appreciated that other suitable shielding devices may be employed in accordance with the present disclosure.

In this illustrated embodiment, the gap or distance between the masking members corresponds to the gap or distance that will be between the markings on the marked PTFE tubing. It should be appreciated that the distances between the masking members of the shielding device corresponds to different portions along the length of the body of the PTFE tubes. Accordingly, this embodiment facilitates that the portions of the body of the PTFE tubes that correspond to the placement of the masking members of the shielding device are protected or masked (and the portion of the body of the PTFE tubes that do not correspond to the placement of the masking members of the shielding device are not protected or masked).

In one embodiment, to create equally spaced apart markings along the length of the body of the PTFE tubing, the masking members of the shielding device are equally spaced apart. In another embodiment, to create unequally spaced apart markings along the length of the body of the PTFE tubing, the masking members of the shielding device are unequally spaced apart. Accordingly, it should be appreciated that by positioning the masking members of the shielding device in any suitable configuration, markings in any desired pattern or any combination of patterns can be created on the surface of the body of the PTFE tubing.

Figure 9A:
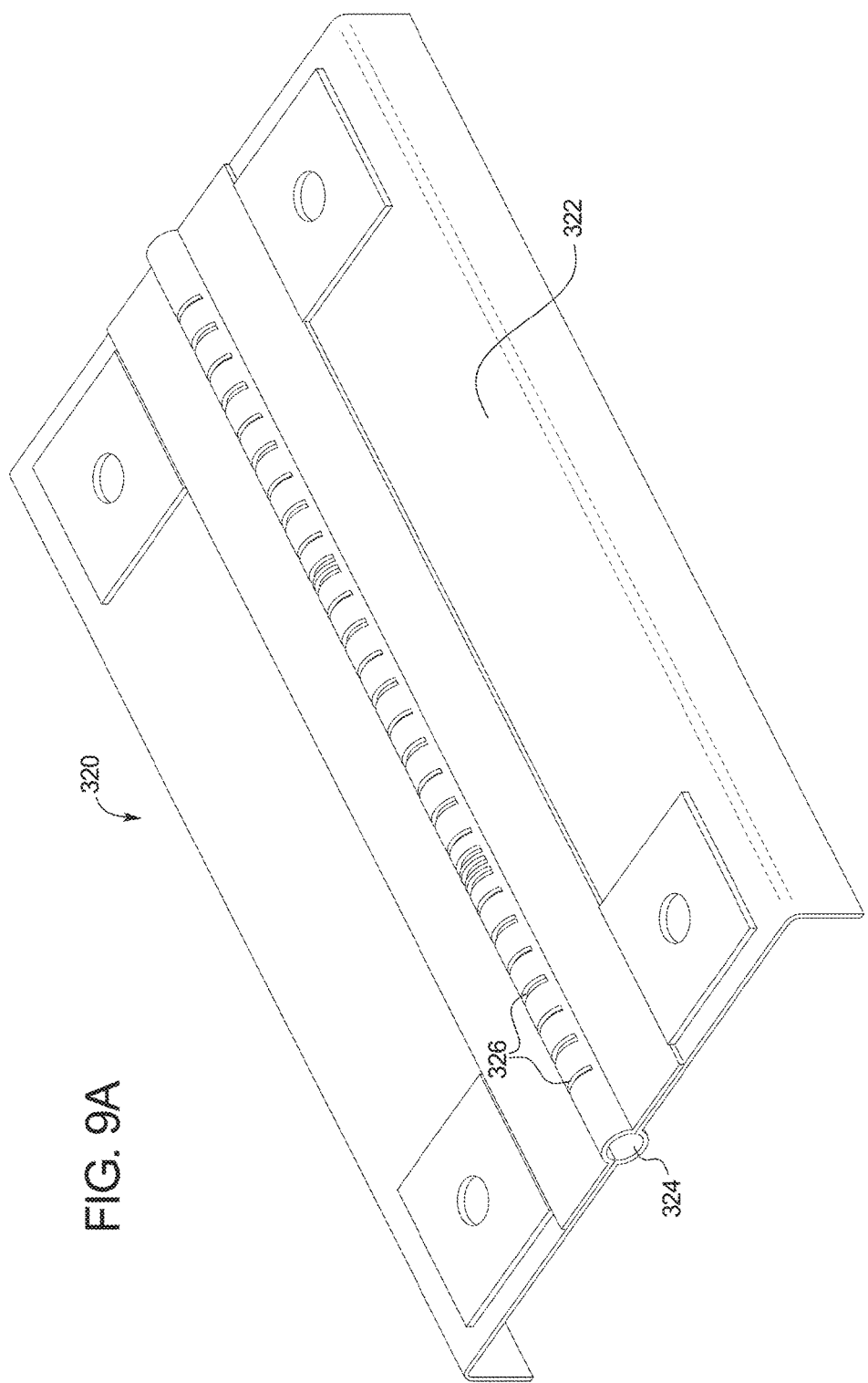
FIG. 9A is a fragmentary top perspective view of another example shielding device utilized in association with coating one or more PTFE tubes.

In another embodiment, the shielding device includes one or more slots, openings or apertures that are designated lengths apart. For example, as seen in FIGS. 9A and 9B, to protect or mask one or more parts of the PTFE tubing, shielding device 320 is utilized. Shielding device 320 includes a body 322 which includes or defines a channel 324 configured to receive a portion of a PTFE tube. As also seen in FIGS. 9A and 9B, the body of shielding device includes a semi-cylindrical member or guard that includes or defines one or more slots, openings or apertures 326. In this embodiment, the positioning of the slots of the shielding device correspond to the positioning of the markings on the marked PTFE tubing. That is, the distances between the slots of the shielding device corresponds to the distances, along the length of the body of the PTFE tubing, between the markings on the PTFE tubing. Accordingly, this embodiment causes portions of the body of the PTFE tubes that correspond to the slots of the shielding device to be not protected or masked (and the portion of the body of the PTFE tubes that corresponds to the shielding device to be protected or masked).

After shielding one or more PTFE tubes using the shielding device, as indicated in block 106 of FIG. 1, a coating is applied along a portion or all of the unprotected or unmasked length of the surface of the body of each PTFE tube. In this embodiment, the application of the coating to certain unblocked, unprotected, unshielded or otherwise unmasked parts or portions of the body of the PTFE tubing (coupled with the coating not being applied to certain blocked, protected, shielded or otherwise masked parts or portions of the body of the PTFE tubing) accomplishes that the coating is selectively applied to the surface of the body of the PTFE tubing.

In one embodiment, the coating includes a binder, such as an epoxy, phenolic, phenoxy, polyimide, polyamide, polyamide-amide, polyphenylene sulfide, polyarylsulfone, polyethylene, polytetrafluoroethylene, fluorinated ethylene propylene, perfluoroalkoxy, tetrafluoroethylene-hexafluoropropylene (FEP), polyetheretherketone (PEEK), polyetherketone (PEK), tetrafluoroethylene perfluoromethyl vinyl ether copolymer (MFA), an acid based PTFE, FEP or MFA primer, or any suitable binder or resin. In one embodiment, the coating includes an ultraviolet light cure resin to semi or fully cure the coating. In another embodiment, the coating includes an electron beam cure resin. It should be appreciated that the coating may include any suitable binders which, when cured, adheres to the surface of the PTFE tubing, and is flexible, stable, resistant to chemicals, and/or is readily sterilized and resistant to contamination.

The coating also includes at least one pigment or combination of pigments such as one or more suitable organic pigments, inorganic pigments, extender pigments, magnetic receptive pigments and/or laser excitable pigments. The organic pigments (with low to moderate heat resistance and which are represented as bright colors) include, but are not limited to: phthalocyanine blues and greens, diarylide yellows and oranges, quanacridone, naphthol and toluidine reds, carbizole violets, and carbon black. The inorganic pigments (with moderate to high temperature resistance and which are represented as dull to moderately bright colors) include, but are not limited to: iron oxide reds and yellows, chrome oxide greens, titanium oxide white, cadmium reds, ultramarine blues, moly oranges, lead chromate yellows, and mixed metal oxides of various shades of brown, yellow, blue, green and black. The extender pigments (which are inorganic and provide a reinforcing/strengthening function) include, but are not limited to: talc, calcium carbonate, silicate and sulfate, silica, mica, aluminum hydrate and silicate, barium sulfate (blanc fixe/barites), and attapulgite. The laser exciteable pigments (which are excited by laser energy), such as near-infrared reflective pigements include, but are not limited to: mica, pearl pigment, Kaolin and aluminum silicate derivatives, antomony trioxide, metallic pigment, aluminum flake pigment, iron oxide, and attapulgite. Additionally, the coating may also include one or more of the following functional pigments, such as conductive pigments, flattening pigments for controlling gloss, clays and other rheology modifying pigments. In another embodiment, the coating includes one or more metal oxide pigments, and/or one or more FDA non-objection status for food contact approved end use pigments.

In different embodiments, the coating is a Standard Technical Applied Resources, Inc. FEP Ink with the appropriate pigments, a Standard Technical Applied Resources, Inc PTFE ink with the appropriate pigments, a GEM® WB1150 High-Temp Striping Ink with the appropriate pigments, a GEM® WB1140 High-Temp Marking Ink with the appropriate pigments, a GEM® 7700 Band Marking coating with the appropriate pigments, a GEM® 6000 Series High Temp Ink with the appropriate pigments, a GEM® 4700 Series PTFE Colorant coating with the appropriate pigments, a Colorant Chromatics FEP Striping Ink with the appropriate pigments, a Tiger Inks & Coatings TIGERMARK T1000 Series coating with the appropriate pigments, a Xylan®

1514 low-friction coating with the appropriate pigments, a VICOTE® 700 Series coating with the appropriate pigments, a VICOTE® 800 Series coating with the appropriate pigments, a DuPont™ 420 Series coating with the appropriate pigments, a DuPont™ 857N504 coating with the appropriate pigments, a DuPont™ 851N504 coating with the appropriate pigments, a DuPont™ 857G504 coating with the appropriate pigments, a DuPont™ 851G504 coating with the appropriate pigments, a DuPont™ 851G204 coating with the appropriate pigments, a DuPont™ 851G321 coating with the appropriate pigments, a WHITFORD® OC 600 Series coating with the appropriate pigments, a WHITFORD® OC 600D8686Z coating, a WHITFORD® OC 600D8686Z coating with the appropriate pigments, a WHITFORD® OC 606D8881Z coating with the appropriate pigments, a WHITFORD® OC 625D17012Z coating with the appropriate pigments, a WHITFORD® OC D10712Z coating with the appropriate pigments, a WHITFORD® OC 625D8684Z coating with the appropriate pigments, a WHITFORD® OC 655D8692Z coating with the appropriate pigments, an MPC 992003 coating with the appropriate pigments, a Ultralon® OC Series coating with the appropriate pigments, a Fluoroplate® 41141 Series coating with the appropriate pigments manufactured by Orion Industries, or any suitable coating and specifically any suitable coating which is manufactured without perfluorooctanoic acid (PFOA) material (as mandated by the Environmental Protection Agency's requirement that PFOA materials be eliminated from the manufacturing process of certain coatings by 2015).

In the illustrated embodiment, the coating is applied by spraying the outer surface of the body of the PTFE tubing with the coating. For example, a layer approximately 0.0003" to 0.0005" thick of the wet coating is applied to one or more unmasked portions of the outer surface of the body of the PTFE tubing. In this example, a wet coating is about 25% solids (by volume) such that a coating which is 0.0005" thick when applied wet will be 0.000125" thick when the coating is fully cured. In one such embodiment, as described below, the amount or thickness of the coating applied to certain unblocked portions of the body of the PTFE tubing is determined based on the amount or thickness which the diameter of the PTFE tubing will contract or shrink when the PTFE tubing is fully cured.

Figure 2H:
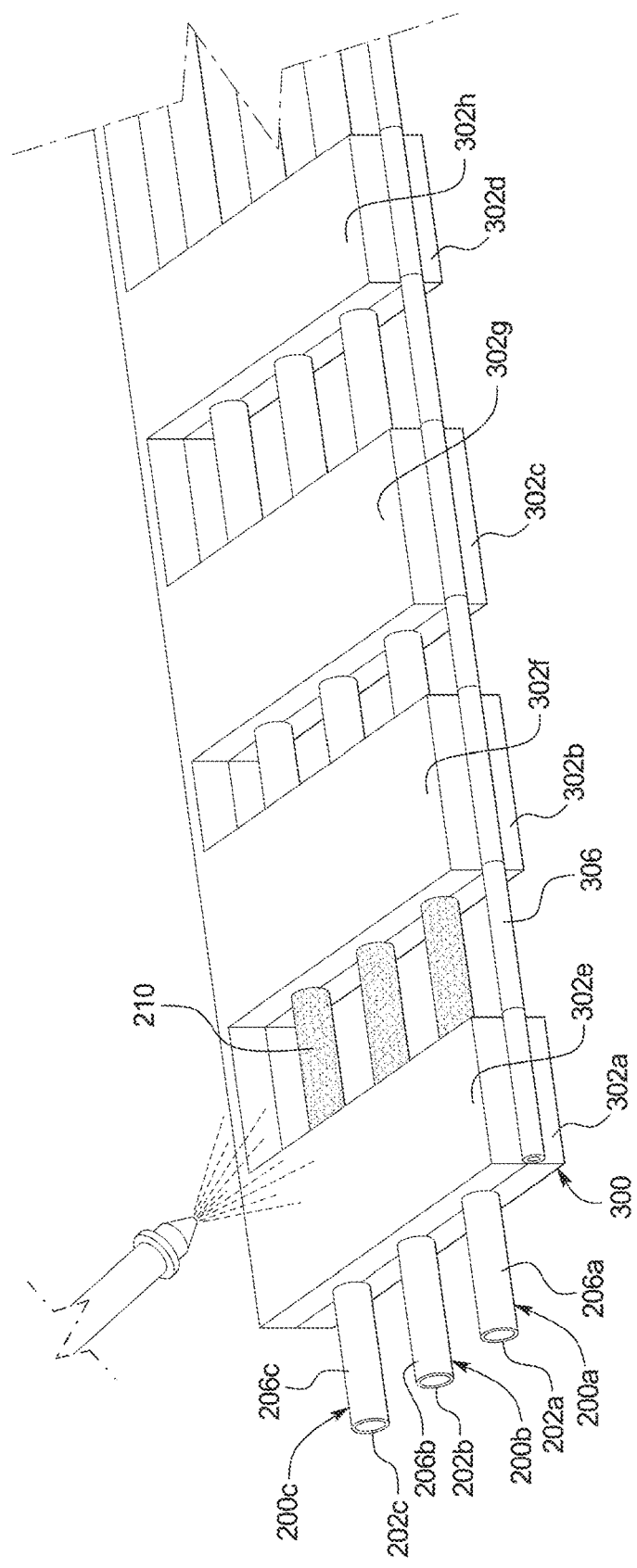
FIG. 2H is a fragmentary perspective view of the PTFE tubes of FIG. 2G being coated from the second, different direction to selectively coat portions of the surfaces of each of the PTFE tubes.

In the illustrated embodiment, to account for the cylindrical shape of the body of the PTFE tubing, a coating is applied to one or more of the unshielded portions of the body of the PTFE tubing in a plurality of sequential coating applications. For example, as seen in FIG. 2D, a first coating 210 is applied to a first unshielded portion of the body of the PTFE tubing from a first direction. As seen in FIG. 2E, the first coating is then applied to the first unshielded portion of the body of the PTFE tubing from a second, different direction. In this illustrated embodiment, as seen in FIG. 2F, the shielding device (including the PTFE tubes) is rotated, such as the illustrated 180° rotation, to expose an uncoated surface of the first unshielded portion of the body of the PTFE tubing. Following this rotation, as seen in FIGS. 2G and 2H, to completely coat this portion of the body of the PTFE tubing, the coating is then applied to the first unshielded portion of the body of the PTFE tubing from two different directions. In this illustrated embodiment, because of the shape of the body of the PTFE tubing, to completely coat the unmasked portions of the body of the PTFE tubing, a multi-directional application process is implemented. In another embodiment, to account for the shape of the body of the PTFE tubing, the coating is applied from one side of the shielding device at different directions and then the coating is applied from different directions from the opposite side of the shielding device. In another embodiment, to account for the shape of the body of the PTFE tubing, the coating is simultaneously or substantially simultaneously applied from different sides of the shielding device at different directions. Such processes ensure that the coating is applied to the unblocked, unprotected, unshielded or otherwise unmasked portions of the body of the PTFE tubing.

In the illustrated embodiment, a plurality of different colored coatings are applied to different unblocked, unprotected, unshielded or otherwise unmasked portions of the body of the PTFE tubing. This embodiment facilitates that different portions of the coated PTFE tubing will be different colors to indicate different information to the medical professional using the PTFE tubing. For example, as seen in FIG. 2I, a first coating 210a of a first color is applied to one or more unblocked, unprotected, unshielded or otherwise unmasked portions of the body of the PTFE tubing and a second, different coating 210b of a second, different color is subsequently applied to one or more unblocked, unprotected, unshielded or otherwise unmasked portions of the body of the PTFE tubing. In this example, the resulting coated PTFE tubing includes a first marking 212a of a first color along one or more portions of the PTFE tubing and a second marking 212b of a second, different color along one or more different portions of the PTFE tubing. In another embodiment, at designated points on the body of the PTFE tubing, different colored coatings are applied and the marks are created in a gradation of successively, incrementally darker colors to create a progressively darker and darker mark to further enhance the ability to create distance codes or even directional force guides on the PTFE tubing.

After applying the coating, the coating is dried, semi-cured or slightly under-cured as indicated in block 108 of FIG. 1. In one example embodiment, the coated PTFE tubing is under cured to between 250° F. (121.11° C.) and 400° F. (204.44° C.). In another embodiment, the coated PTFE is air dried for a designated period of time to enable the applied coating to dry. Such drying or partial curing of the coating causes the coating to be sufficiently dry and physically stable.

After partially curing the coating, the PTFE tubing is removed from or otherwise decoupled from the shielding device as indicated in block 110 of FIG. 1 and seen in FIG. 2I. As indicated in block 112 of FIG. 1, both ends of the coated PTFE tubing are then secured (i.e., held stationary or otherwise held in place). In one such embodiment, as seen in FIG. 2J, a first or proximal end 202 of the body of the PTFE tubing is connected to a first suitable holder or clamp 402a of a securing device and a second or distal end 204 of the body of the PTFE tubing is connected to a second suitable holder or clamp 402b of the securing device. In one embodiment, each clamp is configured to engage or secure a PTFE tubes. In another embodiment, each clamp is configured to engage or secure a plurality of PTFE tubes such that a plurality of PTFE tubes can be simultaneously secured (and thus cured simultaneously).

While the ends of the coated PTFE tubing remain secured to prevent shrinking of the PTFE tubing, as indicated in block 114 of FIG. 1, the coated PTFE tubing is suitably further or finally cured. In one such embodiment, as seen in FIG. 2K, with the two clamps securing the ends of the PTFE tubing, the coated portions of the PTFE tubing is cured, such as by radiated heat, to a designated temperature, such as 650° F. (343.33° C.) for a designated duration, such as fifteen minutes. In this illustrated embodiment, radiated heat is directed to specific portions of the coating by masking the uncoated portions of the PTFE tubing (with a suitable temperature resistant masking device configured to shield the uncoated portions of the PTFE tubing from the heat source). In another such embodiment, the further or final curing process includes curing at the coated portions of the PTFE tubing at a temperature between 610° F. (321.11° C.) to 1050° F. (565.56° C.). In this embodiment, the duration of the further or final cure depends on the further or final cure temperature, wherein a higher final cure temperature requires a shorter cure duration and a lower final cure temperature requires a longer cure duration.

It should be appreciated that as described below, the further or final cure is at such a designated temperature (i.e., above the recommended maximum temperature which exceeds the use temperature rating of PTFE and at which the PTFE tubing begins to warp) that the further cure causes the body of the PTFE tubing to shrink or contract. Accordingly, the disclosed embodiment of utilizing an anti-shrinking device, such as a plurality of clamps to secure the ends of the coated PTFE tubing for the further or final cure limits, inhibits or prevents the PTFE tubing from shrinking or contracting along the length of the PTFE tubing. Specifically, the force applied by the clamps to the ends of the body of the PTFE tubing is of a force at least equal to the force of contraction of the PTFE tubing, thus limiting or preventing the length of the PTFE tubing from contracting. In certain embodiments, to provide the degree of force necessary to limit or prevent the length of the PTFE tubing from contracting, for one or both ends of the PTFE tubing, a clamp is used which holds that end of the PTFE tubing tight enough to damage or crush the end of the PTFE tubing. In these embodiments, after the PTFE is cured, the damaged ends of the PTFE tubing are cut off and discarded. It should be appreciated that in these embodiments, no coating is initially applied to these discarded portions of the PTFE tubing and the coatings are placed at designated intervals along the length of the PTFE tubing to account for the subsequent cutting off of these portions of the PTFE tubing.

The final cure causes the binder to melt and bond to the surface of the body of the PTFE tubing. Specifically, in one embodiment, by curing the coated PTFE tubing to a designated temperature of 650° F. (343.33° C.), both the binder of the coating and the molecules of the PTFE at or near the outer surface of the body of the PTFE tubing melt. The melted coating and the melted molecules of the PTFE bond or otherwise adhere to each other to adhere the coating, and specifically the pigments in the coating, to the surface of the body of the PTFE tubing. More specifically, because the PTFE is a thermoset and the binder material, such as FEP or MFA, is a thermoplastic, the final cure causes the melt flow PTFE at or near the outer surface of the body of the PTFE tubing to melt and molecularly bond with the binder. Such a cure temperature provides increased adhesion of the coating to the surface of the body of the PTFE tubing (compared to curing coatings at the recommended temperature at or below the 500° F. (260° C.) at which PTFE begins to decompose and soften). Such bonding minimizes or ensures that the coating will not easily or readily peel or rub off during use of the PTFE tubing and be left inside the patient's body. Moreover, such bonding ensures that the coating will not readily rub or peel off before or after use of the PTFE tubing, thus destroying the usefulness of the markings, and increasing the risk that the PTFE tubing will be inserted either too deep, or not deep enough (and harm the patient and/or render the medical procedure ineffective). In other words, by curing the PTFE tubing to a temperature above which the PTFE tubing begins to degrade, an increased adhesion of the coating to the surface of the PTFE tubing is achieved (and thus a reduction in the peeling off or dislodging of the coating on the surface of the PTFE tubing is also achieved). Such adhesion of the pigmented coating to the surface of the PTFE tubing provides that when the PTFE tubing flexes or bends when inserted into a patient, the applied pigmented coating is enabled to also flex or bend and remain adhered to (i.e., not become dislodged from) the PTFE tubing.

It should be appreciated that different types of PTFE have different melting temperatures and thus the further or final cure temperature of the coated PTFE tubing is based, at least in part, on the construction of the PTFE tubing. For example, a further or final cure temperature of at least 650° F. (343.33° C.) is employed to cause the molecules of solid PTFE at or near the outer surface of the body of the solid PTFE tubing to melt. In another example, a further or final cure temperature of at least 500° F. (260° C.) is employed to cause the molecules of expanded PTFE at or near the outer surface of the body of the expanded PTFE tubing to melt. Accordingly, by accounting for the melting temperature of the specific type of PTFE used to form the PTFE tubing (and further accounting for the same type of PTFE made from different manufacturers may have different melting temperatures), the present disclosure achieves an increased adhesion of the coating to the surface of each specific type of PTFE tubing while also minimizing the amount of decomposition and emission of any harmful byproducts caused by heating such PTFE above the recommended maximum use temperature for that specific type of PTFE.

It should also be appreciated that because one or more portions of the PTFE tubing disclosed herein are heated to a temperature above the initial decomposition temperature of PTFE, the cure of the applied coatings occurs in a controlled environment with the appropriate exhaust and filtration systems, such as appropriate carbon filtration systems, which absorbs harmful airborne effluent byproducts of the decomposition of the PTFE and thus minimizes any exposure to harmful byproducts emitted during the cure of the PTFE tubing. It should be further appreciated that because the PTFE only begins to decompose and soften at temperatures above 500° F. (260° C.) and the decomposition of the PTFE is a gradual process, the amount of time the further cure occurs is limited to the designated period of time to facilitate that only the molecules of the PTFE at or near the outer surface of the body of the PTFE tubing begin to melt and the applied coating adheres to the outer surface of the body of the PTFE tubing. Such limits to the amount of time the PTFE is above the recommended maximum use temperature of 500° F. (260° C.) accomplishes that the amount of decomposition and emission of any harmful byproducts, if any, of the PTFE is minimal. In this embodiment, such limited duration of the further cure also facilitates that only the molecules of the PTFE at or near the outer surface of the body of the PTFE tubing reach a temperature of at least 650° F. (343.33° C.) and other cured portions not at or near the outer surface of the body of the PTFE tubing do not reach a temperature of at least 650° F. (343.33° C.).

Figure 3A:
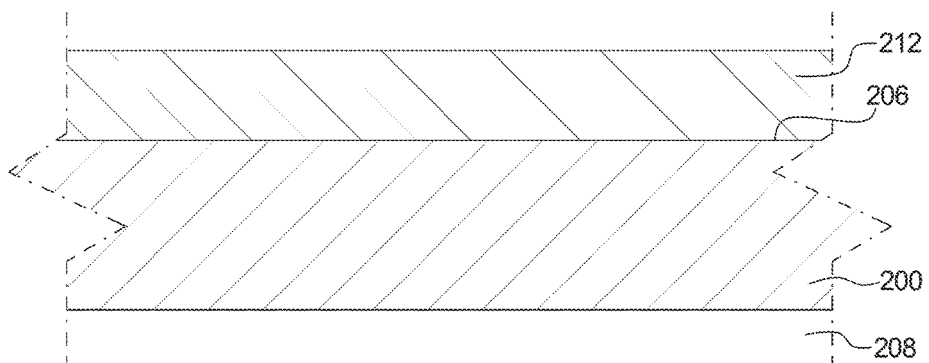
FIG. 3A is a fragmentary cross-sectional view of the coated, uncured PTFE tubing.
Figure 3B:
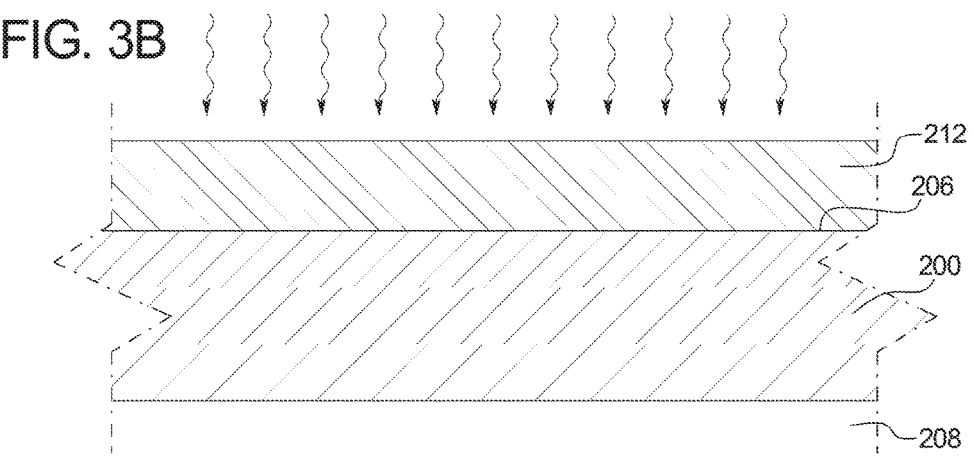
FIG. 3B is a fragmentary cross-sectional view of the coated, partially cured PTFE tubing of FIG. 3A

For example, as illustrated in FIG. 3A, prior to the final cure, the applied coating 212 and the outer surface 206 of the body of the PTFE tubing 200 are the same temperature or substantially the same temperature (as indicated by the equally spaced apart thermal temperature indicating hash markings). In this illustrated example, as seen in FIG. 3B and as indicated by the different spaced apart thermal temperature indicating hash markings, near the beginning of the final or further cure, the heat is applied to the coated PTFE tubing such that the temperature of the coating 212 is increased to a second temperature (which is greater than the first temperature) and the molecules of the PTFE tubing at or near the outer surface 206 of the body of the PTFE tubing are increased to a third temperature (which is lower than the second temperature). As further seen in FIG. 3B, the heat is applied to the coated PTFE tubing such that the molecules near the center of the PTFE tubing are increased to a fourth temperature (which is lower than the third temperature) and the molecules of the PTFE tubing at or near the lumen 208 of the PTFE tubing are increased to a fifth temperature (which is lower than the fourth temperature).

Figure 3C:
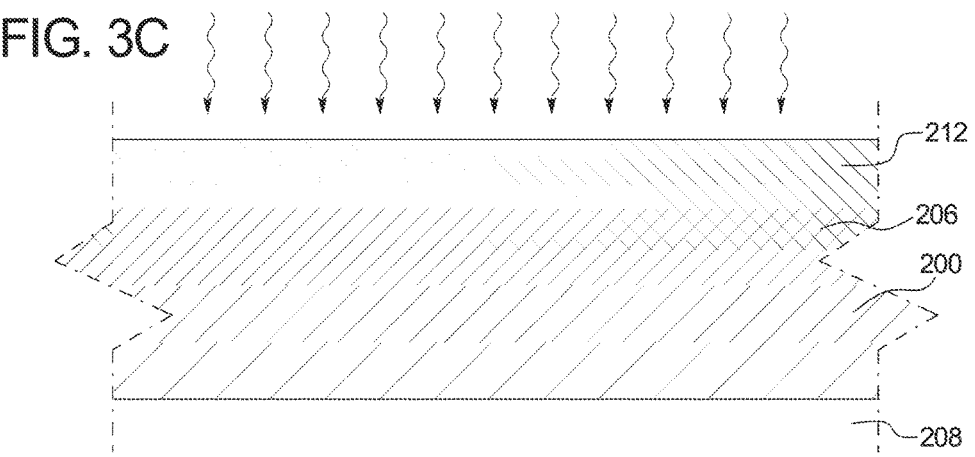
FIG. 3C is a fragmentary cross-sectional view of the coated, fully cured PTFE tubing of FIG. 3B.

As seen in FIG. 3C, near the end of the final or further cure, the coating 212 and the molecules of the PTFE tubing at or near the outer surface 206 of the body of the PTFE tubing are each increased to a temperature of at least 650° F. (343.33° C.) which causes both the binder of the coating and the molecules of the PTFE at or near the outer surface of the body of the PTFE tubing to melt. The melted coating and the melted molecules of the PTFE bond or otherwise adhere to each other (as indicated by the cross-hatching of FIG. 3C) to adhere the coating, and specifically the pigments in the coating, to the surface of the body of the PTFE tubing. As further seen in FIG. 3C, the heat is applied to the coated PTFE tubing such that the molecules near the center of the PTFE tubing and the molecules of the PTFE tubing at or near the lumen of the PTFE tubing are each increased to lower temperatures (than the temperature of the molecules of the PTFE tubing at or near the outer surface of the body of the PTFE tubing) which will minimize and/or prevent the decomposition of the PTFE caused by the PTFE being heated above the PTFE decomposition temperature of 500° F. (260° C.). It should be appreciated that the cure temperature utilized and the duration which the PTFE tubing is cured is based on the composition of the PTFE tubing and/or one or more pigments of the applied coating.

After the final cure, each secured end of the body of the PTFE tubing is released as indicated in block 116 of FIG. 1. In one such embodiment, after the final cure, the PTFE tubing remains in the securing device and forced cooling, ramped or controlled reduction in temperature or room temperature cooling is employed to minimize any stress relief or other factors that may contribute to the shrinking of the PTFE tubing length. The resulting PTFE tubing, as seen in FIG. 2L, includes one or more marking used to convey information to the medical professional using the PTFE tubing. It should be appreciated that because PTFE tubing often flexes or bends when inserted into a patient, the markings bonded to the surface of the PTFE tubing disclosed herein are enabled to also flex or bend and remain adhered to the PTFE tubing.

It should be appreciated that as described above, if the indicated markings along the length of the body of the PTFE tubing are inaccurate, the PTFE tubing may be inserted too far into a patient or the PTFE tubing may not be inserted far enough into a patient. It should be further appreciated that as also described above, when PTFE tubing is cured to temperatures above the recommended maximum use temperature of 500° F. (260° C.), the dimensions of the PTFE tubing begin to warp or change. Accordingly, in this embodiment, to counteract any shrinking along the length of the body of the PTFE tubing that might occur when the PTFE tubing is further or final cured at a designated temperature, such as 650° F. (343.33° C.) for a designated period of time, the PTFE tubing disclosed herein is secured to limit, inhibit or prevent such shrinking. That is, as described above, compared to known methods of marking PTFE tubing, a higher cure temperature facilities a stronger bond or adhesion of the coating to the surface of the PTFE tubing, but the higher cure temperature is accompanied by warping of the PTFE tubing. Thus, the present disclosure employs the higher cure temperature while simultaneously or substantially simultaneously accounting for and/or otherwise counteracting this potential warping or shrinking along the length of the PTFE tubing.

More specifically, because: (i) the body of the PTFE tubing contracts when heated to a designated temperature, such as at least 650° F. (343.33° C.) for a designated period of time, (ii) the shielding device includes gaps between the masking members (which are spaced apart at measured intervals along the length of the shielding device), and (iii) these gaps correspond with the locations of the intended markings to be placed at measured intervals along the length of the body of the PTFE tubing, as described above and as seen in the illustrated embodiment of FIGS. 2A to 2L, to ensure that the markings on the fully cured PTFE tubing correspond with the locations of the intended markings, the PTFE tubing is secured in one or more anti-shrinking devices. That is, one or more anti-shrinking devices are utilized to secure the body of the PTFE tubing such that after the final cure, the actual markings along the length of the body of the PTFE tubing still accurately correspond to the intended markings placed at measured intervals along the length of the body of the PTFE tubing.

In one such embodiment, as seen in FIGS. 2J, 2K, 7A and 8, the anti-shrinking device includes utilizing one or more clamps or holders which secure or otherwise hold stationary the ends of the body of the PTFE tubing during the further cure. In another such embodiment, as also seen in FIG. 7A, the anti-shrinking device additionally or alternatively includes utilizing a support member which is fully inserted into the lumen of the PTFE tubing to secure or otherwise hold the body of the PTFE tubing stationary during the further cure. In another such embodiment, the anti-shrinking device or fixtures includes utilizing one or more clamps or holders which each include a support member, such as a cylindrical rod, that is partially inserted into the lumen of the PTFE tubing. In this embodiment, the clamps engage the outer surface of the body of the PTFE tubing and the support member engages the inner surface of the body of the body of the PTFE tubing to secure or otherwise hold the body of the PTFE tubing stationary during the further cure.

It should be appreciated that any suitable anti-shrinking device which inhibits, limits, reduces or prevents the shrinking of the body of the PTFE tubing during the final cure may be utilized in accordance with the present disclosure. In different embodiments, the anti-shrinking device includes one or more liquid anti-shrinking devices, one or more gas anti-shrinking devices, one or more solid anti-shrinking devices, one or more two-dimensional anti-shrinking devices and/or one or more three-dimensional anti-shrinking devices. Moreover, in different embodiments, the support member of the anti-shrinking device includes one or more liquid support members, one or more gas support members, one or more solid support members, one or more two-dimensional support members and/or one or more three-dimensional support members. For example, a portion of the outer surface of the coated PTFE tubing is cured at 900° F. (482.22° C.) while water is passed or flowed under pressure through a tubular support member inserted into the lumen of the PTFE tubing. Such water inside the support member functions to remove the heat from the inside surface of the PTFE tubing (i.e., cool the PTFE tubing) to reduce the shrinkage or deformation of the cured PTFE tubing.

Figure 4A:
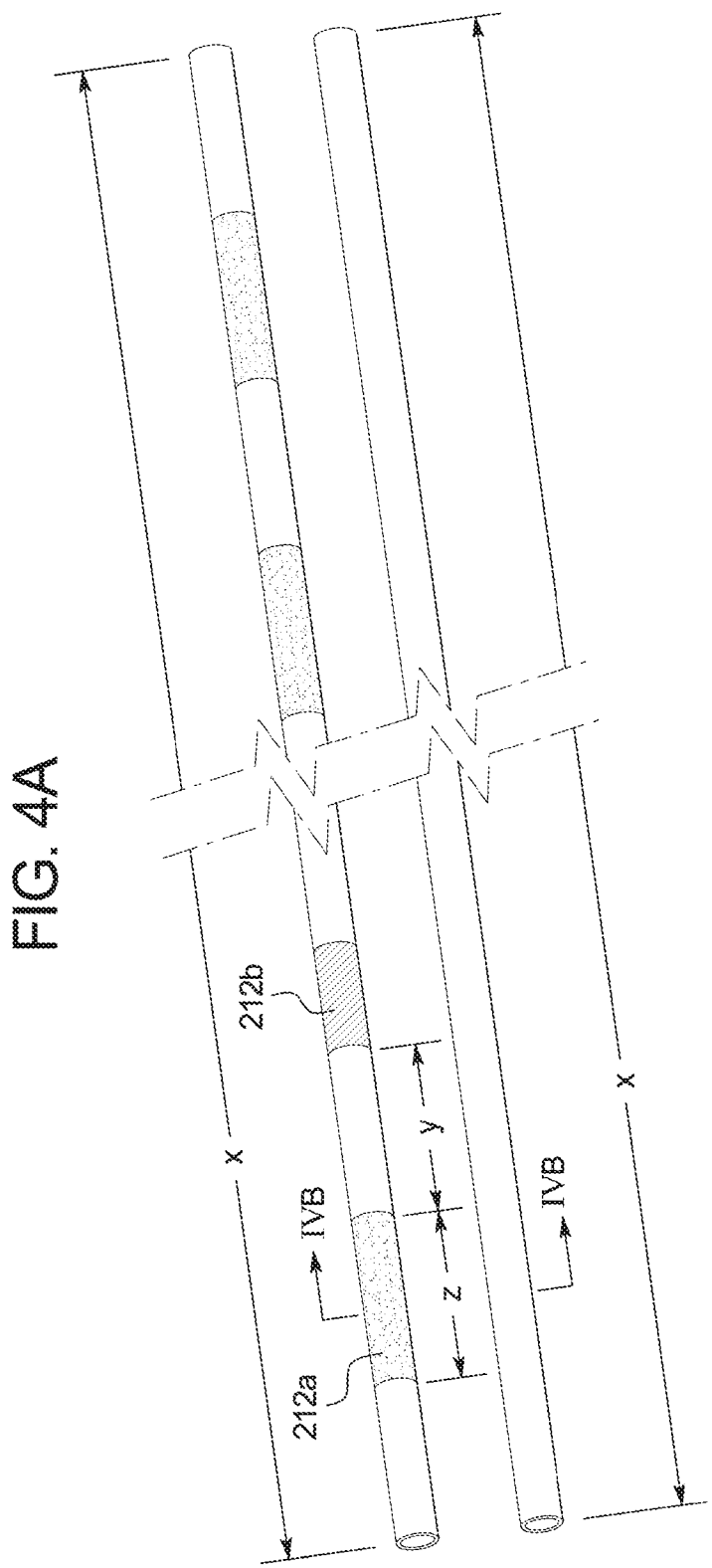
FIG. 4A is a fragmentary perspective view comparing the length of the uncoated, uncured PTFE tubing to the length of the coated, cured PTFE tubing.

In one example, as seen in FIGS. 2I and 4A, the length of the body of the PTFE tubing (indicated as X) remains constant from the pre-coated, pre-cured PTFE tubing of FIG. 4A to the coated, pre-cured PTFE tubing of FIG. 2I, to the coated, cured PTFE tubing of FIG. 4A. As further seen in FIGS. 2I and 4A, the distance between the first applied marking 212a and the second applied marking 212b (indicated as Y) on the coated, pre-cured PTFE tubing of FIG. 2I is the same as the distance between the first applied marking 212a and the second applied marking 212b (also indicated as Y) on the coated, cured PTFE tubing of FIG. 4A. As also seen in FIGS. 2I and 4A, the length of the first applied marking 212a (indicated as Z) on the coated, pre-cured PTFE tubing of FIG. 2I is the same as the length of the first applied marking 212a (also indicated as Z) on the coated, cured PTFE tubing of FIG. 4A. Accordingly, by providing that the markings along the length of the body of the PTFE tubing are accurately placed at designated intervals ensures that when surgeons or other medical professionals have inserted the PTFE tubing into a patient, the PTFE tubing is actually inserted to the length indicated to the surgeons or other medical professionals. Such accurate placement of the markings benefits patients by reducing the likelihood that a medical professional will rely on inaccurate markings along the length of the PTFE tubing when inserting the PTFE tubing into the patient.

Figure 4B:
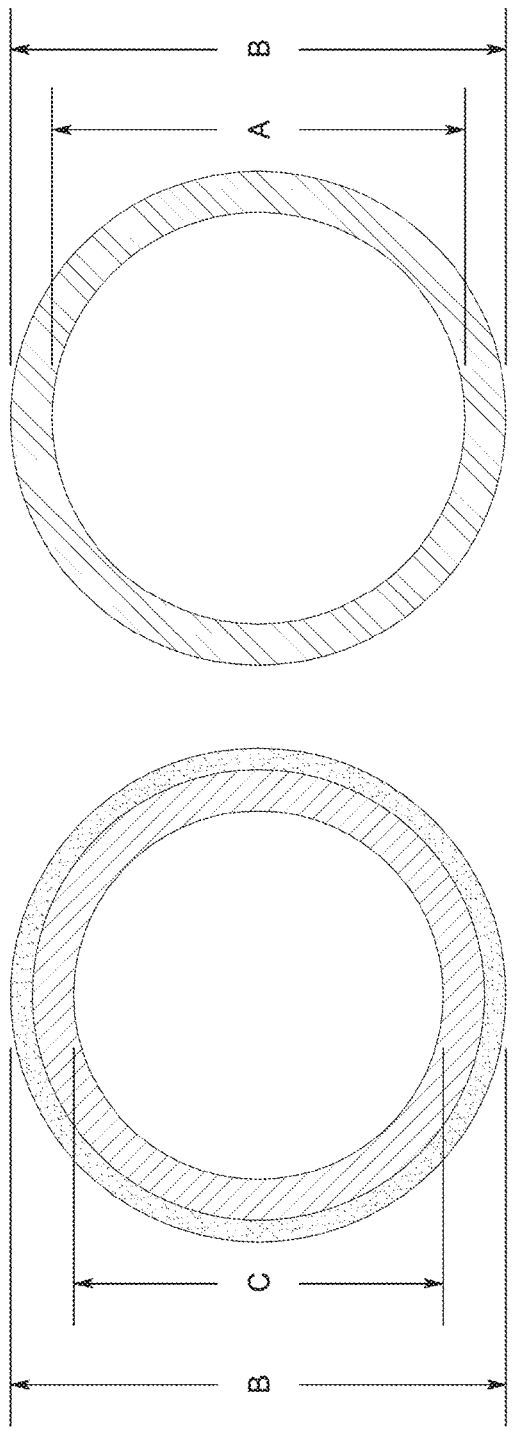
FIG. 4B are cross-sectional views, taken substantially along line IVB of FIG. 4A, comparing the diameter of the uncoated, uncured PTFE tubing of FIG. 4A to the diameter of the coated, cured PTFE tubing of FIG. 4A.

In one embodiment, in addition to compensating or accounting for any dimensional changes (i.e., any shrinking or contracting) along the length of the body of the PTFE tubing, any dimensional changes occurring to the diameter of the body of the PTFE tubing are also compensated or accounted for. Specifically, it should be appreciated that selectively heating the coated portions of the body of the PTFE tubing (without heating the uncoated portions of the body of the PTFE tubing) causes the diameter of the body of the PTFE tubing at these cured portions to contract or shrink. Accordingly, in various embodiments of the present disclosure, to prevent the cured and uncured portions of the marked PTFE tubing from having different outer diameters, the amount of subsequent reduction in the diameter at certain portions of the PTFE tubing is accounted for when determining a thickness or amount of coating to be applied to certain portions of the PTFE tubing. For example, as seen in FIG. 4B, the body of the uncoated, uncured PTFE tubing of FIG. 5A has an inner diameter (indicated as A) which defines the lumen and the uncoated uncured PTFE tubing of FIG. 5A has an outer diameter (indicated as B). In this example, a designated amount or thickness of the coating is applied to certain portions of the outer surface of the body of the PTFE tubing (as seen in FIG. 5B). In this example, this designated amount or thickness of the coating is determined such that when the body of the PTFE tubing is cured (as seen in FIG. 5C), the amount of applied coating compensates for the reduction in the outer diameter of the body of the PTFE tubing. As seen in FIGS. 4B and 5D, this configuration provides that while the inner diameter of the cured, coated portions of the body of the PTFE tubing (indicated as C) will be less than or smaller than the inner diameter of the uncured, uncoated portions of the body of the PTFE tubing (indicated as A), the outer diameter of the cured, coated portions of the body of the PTFE tubing (indicated as B) will be the same or substantially the same as the uncured, uncoated portions of the body of the PTFE tubing (indicated as B). Accordingly, such equal or substantially equal outer diameters reduces or prevents grooves or valleys from being created in the surface of the marked PTFE tubing. That is, by accounting for the subsequent reduction in the diameter of the PTFE tubing when determining an amount of coating to apply to certain portions of the PTFE tubing, less bumps or protrusions having shoulders with sharp edges (which can scrape or irritate bodily tissues, snag vessels or arteries of the patient, or otherwise cause damage and/or trauma to the patient) are created in marking the PTFE tubing disclosed herein.

In one such embodiment, the size of the markings and/or the number of marks grouped together to form a marking indicating different lengths of the marked PTFE tubing. In another such embodiment, small markings can be created at measured intervals along the length of the PTFE tubing to indicate uniform length markers of the PTFE tubing. In another embodiment, markings are created to indicate a specific distance from a reference point on the PTFE tubing, such as a distance from the middle point, the proximal end and/or the distal end. For instance, one band of a color can indicate a first distance from the distal end, while two bands of colors in close proximity can indicate a second distance from the distal end. Likewise, in another embodiment, depending on the size and shape of the PTFE tubing, numbers or characters are created on the surface of the PTFE tubing to indicate a distance from a middle point, the distal end and/or the proximal end. In another embodiment, one or more geometric shapes, including but not limited to: circles, squares, rectangles, triangles, parallelograms, and other polygrams are created to indicate lengths of the PTFE tubing.

In another embodiment, a plurality of different colored coatings are applied to the PTFE tubing such that different colors are created to indicate distances from the middle point, proximal end or distal end of the PTFE tubing. In another embodiment, a plurality of different colored coatings are applied to the PTFE tubing such that a progression of a plurality of interrupted colors is created along the length of the PTFE tubing. In another embodiment, a plurality of different colored coatings are applied such that the PTFE tubing includes a first color (which runs from a distal end of the PTFE tubing to a halfway or middle point of the PTFE tubing) and a second, different, contrasting color (which runs from the proximal end of the PTFE tubing to the halfway or middle point of the PTFE tubing). Such a configuration accomplishes that a surgeon or medical professional can quickly identify when more than 50% of the PTFE tubing is internal to the patient and determine whether a different PTFE tube of a different length should be employed. That is, the PTFE tubing of this embodiment (and other disclosed embodiments wherein different segments of a PTFE tubing are marked with different colors) is utilized by a surgeon or medical professional during a medical procedure to determine the length of the PTFE tubing inserted into a patient's body (i.e., by observing the color of the segments of the PTFE that are external to the patient's body).

It should be appreciated that the markings disclosed herein are not limited to: indicating lengths, but also can indicate the size, type, material, part number, serial number, lot number, manufacturing date, manufacturer of the PTFE tubing. The markings can also include directional arrows, location arrows, bar codes or other codes, or other properties or instructions associated with the PTFE tubing. In another embodiment, the markings disclosed herein form a band or stripe along the entire length or along selected lengths from the distal end to the proximal end of the PTFE tubing. The markings can include a stripe applied to the outer diameter either in a longitudinal manner or a spiral manner around and along a specified or the entire length of the diameter of the PTFE tubing. In different embodiments, these markings can form one or more: linear lines, bands or stripes along the longitudinal axis of the PTFE tubing, spiral patterned lines, bands or stripes along the length of the PTFE tubing, parallel lines, bands or stripes, perpendicular lines, bands or stripes, transverse lines, bands or stripes, any indicia or marking disclosed herein or any combination thereof. It should be appreciated that such formed markings can be utilized in combination with any suitable marking disclosed herein to denote one or more dimensions or sizes along the length of the PTFE tubing.

Unsecured Curing Embodiment

Figure 6A:
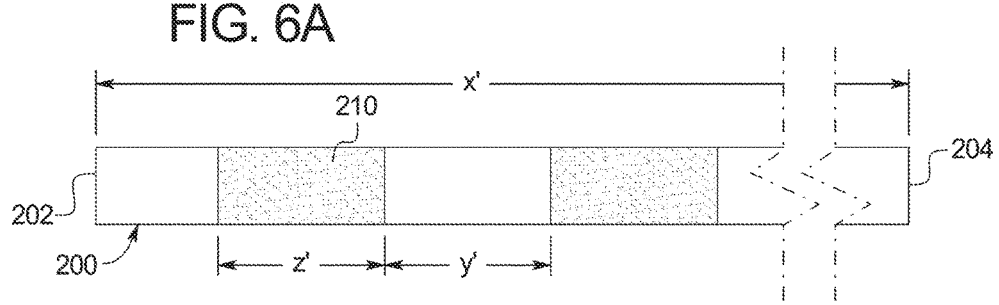
FIG. 6A is a fragmentary side view of an alternative embodiment generally illustrating coated PTFE tubing.
Figure 6B:
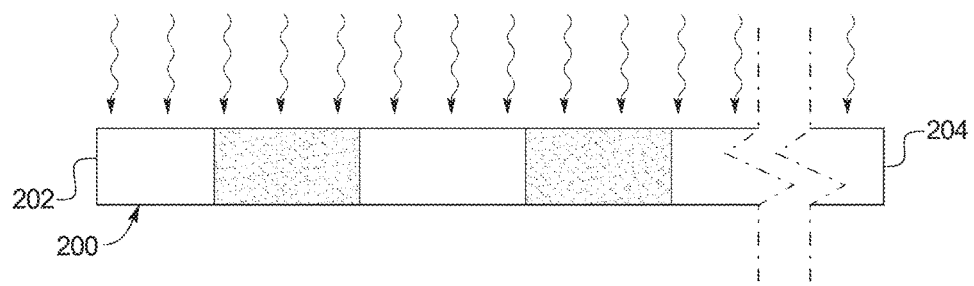
FIG. 6B is a fragmentary side view of the coated PTFE tubing of FIG. 6A being cured while each end is unsecured.
Figure 6C:
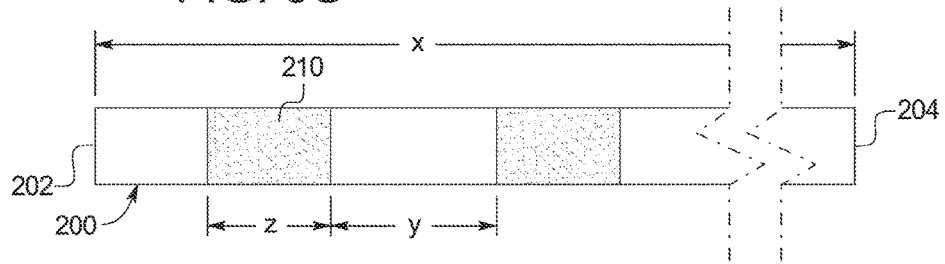
FIG. 6C is a fragmentary side view of the coated, cured and shrunk PTFE tubing of FIG. 6B.

In another embodiment, rather than securing the ends of the body of the PTFE tubing prior to the further or final cure, the masking members of the shielding device are spaced apart to compensate for the contraction or shrinkage of the length of the cured body of the PTFE tubing. In this embodiment, to account for the reduction in length of the body of the PTFE tubing caused by the curing process, the masking members of the shielding device are spaced a greater distance apart such that after the further or final cure (and the shrinkage of the length of the body of the PTFE tubing), the length of the body of the PTFE tubing and the markings along the length of the body of the PTFE tubing corresponds with the intended length of the body of the PTFE tubing and the intended markings along the length of the body of the PTFE tubing. In one example embodiment, if a plurality of masking members of a first shielding device (to be used with PTFE tubing having its ends secured for the final cure) are each a first distance apart and the final cure of the body of the PTFE tubing causes a reduction of the length of the body of the PTFE tubing by designated percentage, then the plurality of masking members of a second shielding device (to be used with body of the PTFE tubing having its ends unsecured or free for the final cure) are each a second distance apart which accounts for this reduction of the length of the body of the PTFE tubing by the designated percentage. In this embodiment, as seen in FIG. 6A, after the coating is selectively applied to the outer surface of the body of the PTFE tubing and the body of the PTFE tubing is partially cured, the partially cured body of the PTFE tubing has: (i) a first length (indicated as X'), (ii) at least two markings which are a first distance apart (indicated as Y'), and (iii) the length of a first of the markings is a first distance (indicated as Z'). As seen in FIG. 6B, the body of the PTFE tubing is positioned in a suitable curing device and cured while both ends of the body of the PTFE tubing remain free or unsecured. Such curing the body of the PTFE tubing having free ends causes at least the length of the body of the PTFE tubing to shrink or contract. Accordingly, after the body of the PTFE tubing is cured (with both ends unsecured or free), as seen in FIG. 6C, the length of the body of the PTFE tubing is reduced by the designated percentage and the resulting PTFE tubing has: (i) a second length (indicated as X), (ii) at least two markings which are a second distance apart (indicated as Y), and (iii) the length of a first of the markings is a second distance (indicated as Z). It should be appreciated that when compared to the PTFE tubing of FIG. 4A (i.e., the PTFE tubing that is cured with the ends of the PTFE tubing secured), the spacing of the masking members of the shielding device of this embodiment accounts for the reduction in the length of the PTFE tubing to accomplish that both the marked PTFE tubing of FIG. 4A and the marked PTFE tubing of FIG. 6C have: (i) the same length (indicated as X), (ii) at least two markings which are the same distance apart (indicated as Y), and (iii) the length of a first of the markings is the same distance (indicated as Z). In this embodiment, by providing that the markings along the length of the body of the PTFE tubing are accurately placed at designated intervals ensures that when surgeons or other medical professionals have inserted the marked PTFE tubing into a patient, the marked PTFE tubing is actually inserted to the length indicated to the surgeons or other medical professionals.

Alternative for Preparing PTFE Tubing to Coat

In one alternative embodiment, prior to selectively coating the body of the PTFE tubing, the body of the PTFE tubing is cleaned by condensing a vaporized cleaner on the surface of the body of the PTFE tubing, wherein the cleaner dissolves and washes away the oils on the surface of the body of the PTFE tubing. In another embodiment, laser energy from a laser device, such as a YAG laser or $CO_2$ laser, is directed at the surface of the PTFE tubing to clean or otherwise selectively etch the surface of the body of the PTFE tubing.

In another embodiment, the body of the PTFE tubing is cleaned with an ultrasonic cleaner used in combination, prior or after the ultrasonic degreaser, with a solvent such as acetone, alcohol or another degreaser. Alternatively, the body of the PTFE tubing is pre-cleaned or the method is performed in a "clean room" where the cleaned part is manufactured and the step is not necessary. In another embodiment, the body of the PTFE tubing is heated to a temperature in excess of at least 450° F. (232.22° C.) for a period of time sufficient to thermally degrade surface impurities, draw oils and other impurities out of any pores in the surface of the body of the PTFE tubing and create a non-acidic "passivation" of the surface of the body of the PTFE tubing. In another embodiment, the body of the PTFE tubing is cleaned in a batch or bulk cleaning method, thereby cleaning all of the surfaces of the body of the PTFE tubing. In another embodiment, the body of the PTFE tubing is heated before applying a coating to reduce ambient moisture on the surface of the PTFE tubing and improve adhesion of a coating to the body of the PTFE tubing. In other embodiments, any combination of the cleaning methods mentioned above are used to improve the cleaning process of the body of the PTFE tubing.

Alternative Coatings of PTFE Tubing

In one alternative embodiment, a coating which is formulated with magnetic receptive pigments and/or electromagnetic receptive pigments is utilized, wherein these magnetic receptive pigments will provide internal heat when subjected to one or more appropriate magnetic fields or electromagnetic fields. In this embodiment, such magnetic receptive pigments are applied to non-magnetic substrates, such as the body of the PTFE tubing. Such magnetic receptive pigments are formulated with low-friction materials and appropriate color pigments and binders, such as epoxy and polyimide, which when cured at a suitable temperature provides adhesion to the surface of the body of the PTFE tubing. In this embodiment, the body of the PTFE tubing is subsequently internally heated by exciting or energizing the dispersed magnetic receptive particles.

In one embodiment, a plurality of anti-microbial particles such as silver, ceramic, silver ceramic, silver oxide, glass silver or silver compounds or any suitable anti-microbial agent are applied to one or more of the surfaces of the body of the PTFE tubing to reduce and kill bacteria and other potential germs that are located on the surface(s) of the body of the PTFE tubing or otherwise incorporated into the coating formulation. In one embodiment, the anti-microbial particles are interspersed with the uncured coating. During the below-described curing process, some of the anti-microbial particles migrate or rise to the surface of the coating. The anti-microbial particles are capable of killing bacteria and other harmful organisms which contact the surface of the coated PTFE tubing while in storage or while the medical device is deployed into the body. The coated PTFE tubing therefore minimizes or reduces the chance of infections or other complications in the body after the surgical procedure is complete.

In another embodiment, the coating also includes particles of a low-friction material, such as a fluoropolymer material including PTFE, FEP and MFA. In one embodiment, the particles are micron- and/or sub-micron-sized. In another embodiment, the low-friction material is resistant to chemicals such that the low-friction material will provide a low surface energy outer layer and will resist corrosion, resist oxidization, resist breaking down, resist forming bonds with other materials, and otherwise be unaffected by contacting other chemicals. In another embodiment, the low-friction material is pure and free of contaminants such that the low-friction material can safely be used in medical procedures and can safely contact food for human consumption. In another embodiment, the low-friction material is irradiated, prior to incorporation in the coating, with an electron beam (or other suitable energy source) so that the resulting particles create an easily wetted surface which enables better adhesion to the binder material.

In another embodiment, the coating includes additives, such as silane coupling agents, acids and other materials formulated to improve the bonding capabilities of a coating to the surface of the body of the PTFE tubing or other materials which modify the curing characteristics or the drying characteristics of the coating before curing. In another embodiment, the coating includes additives to improve the wear characteristics, corrosion resistance, and/or electrical properties of the coating. In another embodiment, an alcohol (or other suitable solvent) and a silane coupling agent (or other suitable adhesion promoting agent) are utilized as a primer dip on the smooth or semi-smooth surface of the body of the PTFE tubing.

In another embodiment, a radiopaque material, such as barium sulfide, barium sulfate or a suitable metal, such as tungsten or palladium, is included in the coating and otherwise applied (or selectively applied) to one or more of the inner or outer surfaces of the body of the PTFE tubing. In this embodiment, the radiopaque material provides that a suitable marking shows up when using a suitable imaging device. In these embodiments, the surgeon or other medical professional utilize the imaging device to determine an exact location of the PTFE tubing inside a patient and/or to determine one or more measurements inside the patient.

Alternative Methods of Applying Coating to PTFE Tubing

In one alternative embodiment, the shielding device is made of laser engraved plastic sheet. In another embodiment, the shielding device is made of a laser engraved adhesive sheet of biaxially-oriented polyethylene terephthalate (BoPet). In this embodiment, the adhesive sheet is wrapped around selective portions of the body of the uncoated, uncured PTFE tubing and the coating is applied to the unwrapped portions of the body of the PTFE tubing. In this embodiment, a first cure at 300° F. (148.89° C.) occurs, the adhesive mask is then removed and a final cure at 650° F. (343.33° C.) occurs. It should be appreciated that any suitable laser engraved or machined stencil type shield or mask made of any suitable material, such as stainless steel, copper or aluminum may be employed as a suitable shielding device.

In different alternative embodiments, the coating is sprayed on, applied using an air atomizer or appropriate atomizing device, applied by a siphon, gravity, ultrasonic or pressure pot method which forces the coating through a nozzle at high pressure such that the coating forms a vapor or mist which is directed toward the surface of the body of the PTFE tubing. In these embodiments, the air velocity around the PTFE tubing helps contain any overspray of the coating. In another embodiment, the coating is applied with a variation of siphon or gravity spraying wherein the coating is sprayed at a lower pressure and in higher volume to reduce the amount of volatile organic compounds released during the spraying process. In another embodiment, high speed or low speed rollers are used to apply a film of coating to the surface of the body of the PTFE tubing. In another embodiment, the body of the PTFE tubing is passed under a falling curtain of the coating to coat the surface of the PTFE tubing such that the exposed surface receives a coating on approximately half the outer diameter of the PTFE tubing. In another embodiment, a powder coating system is employed. This powder coating system includes a primer, where required, of a liquid that is preapplied and either cured to dry or remains wet prior to the application of a topcoat of a powder. In another embodiment, an electrostatic, tribo-charged or opposite electrostatic charged spray or powder spray method is used to apply the coating to the surface of the body of the PTFE tubing. The electrostatically charged spray enables an operator to better control the application uniformity of the coating and thereby enhances the uniformity, density and application of the coating on the surface of the body of the PTFE tubing. It should be appreciated that the coating may have one or more characteristics altered to allow for more efficient electrostatic, tribo-charged or opposite electrostatic charged spray techniques to be used to apply the coating to a surface of the body of the PTFE tubing.

In another embodiment, the coating is applied vertically or substantially vertically while the PTFE tubing is also positioned vertically or substantially vertically. In another embodiment, the coating is applied horizontally or substantially horizontally while the PTFE tubing is also positioned horizontally or substantially horizontally. In another embodiment, the coating is applied vertically or substantially vertically while the PTFE tubing is also positioned horizontally or substantially horizontally. In another embodiment, the coating is applied horizontally or substantially horizontally while the PTFE tubing is also positioned vertically or substantially vertically. In these embodiments, the curing of the applied coating occurs while the PTFE tubing is positioned vertically or substantially vertically and/or horizontally or substantially horizontally.

In another embodiment, pad printing is employed to coat one or more portions of the body of the PTFE tubing. Pad printing utilizes an indirect offset printing process that involves an image being transferred from the printing plate via a silicone pad onto the surface of the body of the PTFE tubing. It should be appreciated that any suitable method of applying the coating to one or more portions of any surface of the body of the PTFE tubing may be employed in accordance with the present disclosure.

In another embodiment, rather than applying the coating to the unshielded portion(s) of the body of the PTFE tubing in a plurality of sequential coating applications as described above, a coating is applied to one or more of the unshielded portions of the body of the PTFE tubing in a single coating application. In this embodiment, to account for the cylindrical shape of the body of the PTFE tubing, the PTFE tubing is rotated as the coating is applied.

In one such embodiment, to facilitate the rotation of the PTFE tubing, a support member is inserted into the lumen of the PTFE tubing and the support member is secured or attached to the PTFE tubing, such as using one or more fasteners. In one embodiment, the outer diameter of the body of the support member is slightly smaller than the inner diameter of the body of the PTFE tubing such that the support member tightly fits into the lumen of the PTFE tubing. In another embodiment, the support member includes a hollow tube with an outer diameter which is slightly smaller than the inner diameter of the body of the PTFE tubing. In this embodiment, when air pressure and/or heat is/are applied to the hollow tube, the hollow tube swells to contact the inner surface of the body of the PTFE tubing and support the PTFE tubing. In this embodiment, when the hollow tube is subsequently cooled, the hollow tube will shrink several thousandths of an inch in diameter to allow the support tubing to be easily withdrawn. In these embodiments, either before or after placing the support member into the lumen of the PTFE tubing, the PTFE tubing is placed in, attached to or otherwise coupled with a suitable shielding device. For example, as seen in FIG. 9C, a support member 328, such as a cylindrical rod, is interested into the lumen 208 of the PTFE tubing 200 and the PTFE tubing (including the support member) is then placed in, attached to or otherwise coupled with a suitable shielding device. In one embodiment, when the PTFE tubing (including the support member) is placed in, attached to or otherwise coupled with the shielding device, the surface of the PTFE tubing does not contact the surface of the shielding device (to facilitate the rotation of the PTFE tubing as described below).

Figure 10B:
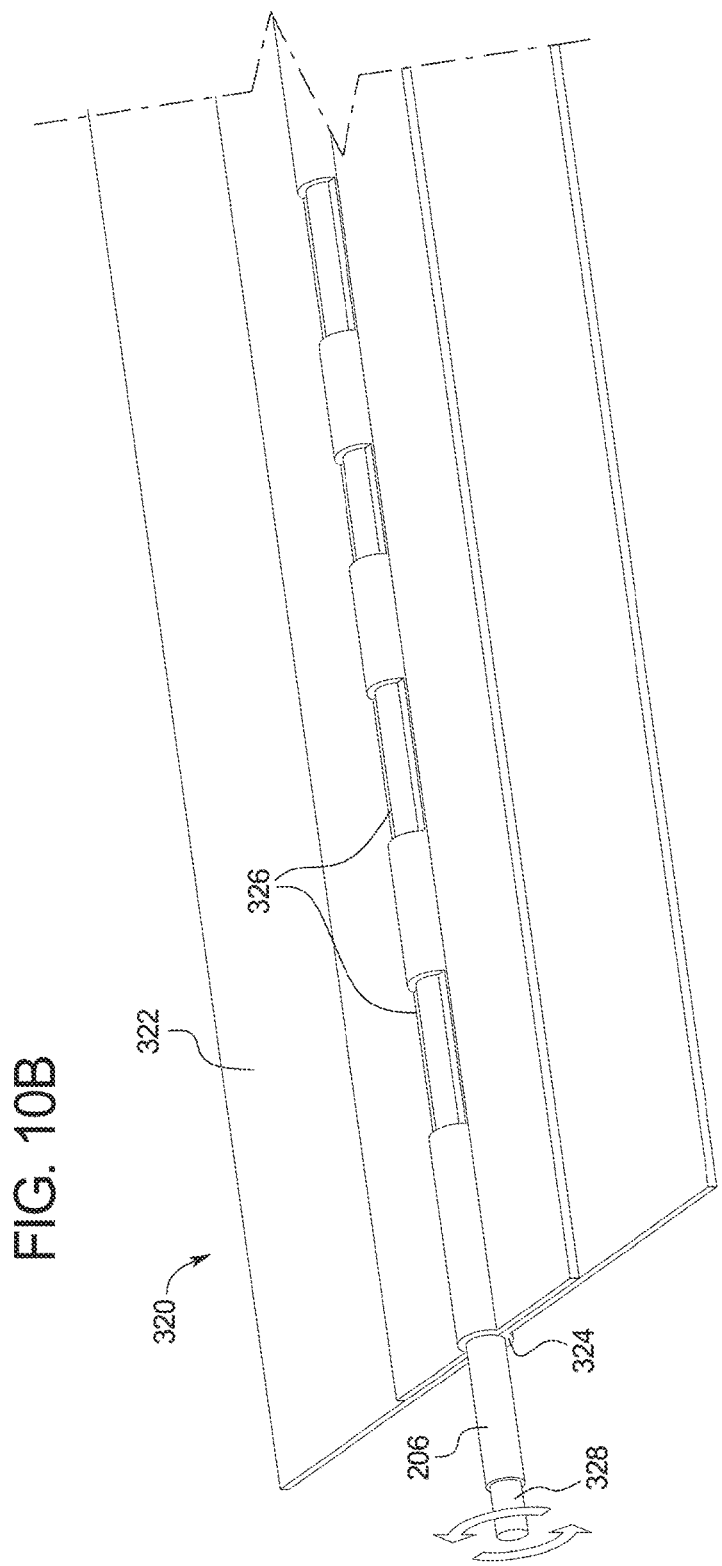
FIG. 10B is a fragmentary perspective view of the PTFE tube of FIG. 10A being rotated.

As seen in FIGS. 10A and 10B, after placing the PTFE tubing in the defined channel of the body of the shielding device, the support member is connected to a rotating device, such as mandrel, which causes the support member to rotate in either a clockwise or a counterclockwise direction. In this example, as the PTFE tubing is secured to the support member, the PTFE tubing is thus rotated in either a clockwise or a counterclockwise direction.

Figure 10D:
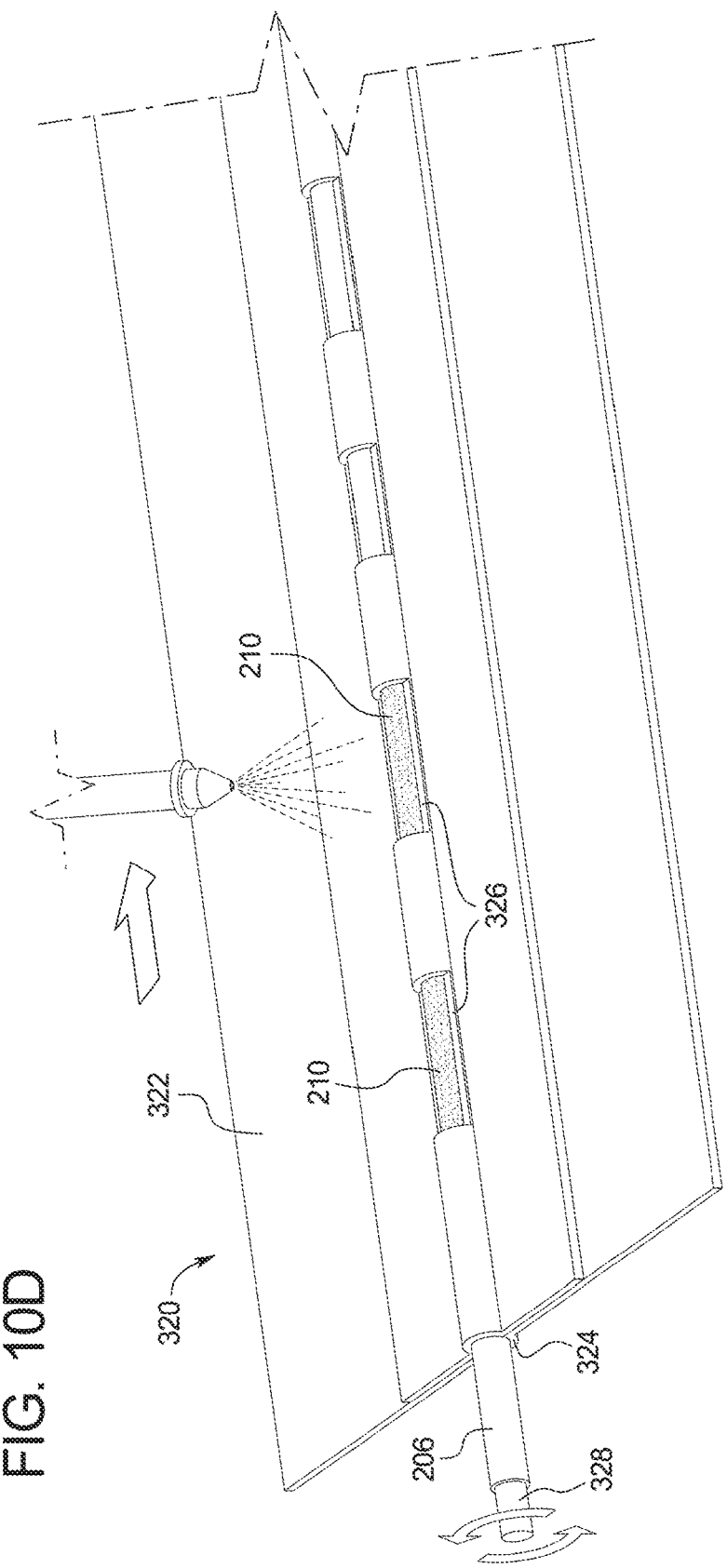
FIG. 10D is a fragmentary perspective view of the PTFE tube of FIG. 10D being coated from the first direction to selectively coat a second portion of the surface of the PTFE tube.

As seen in FIG. 10C, while the support member (and the attached PTFE tubing) is rotating, a first coating 210 is applied to a first unshielded portion of the body of the PTFE tubing from a suitable direction. As seen in FIG. 10D, after applying the first coating to the first unshielded portion of the body of the PTFE tubing, while the support member (and the attached PTFE tubing) remains rotating, the first coating 210 is then applied to a second unshielded portion of the body of the PTFE tubing from the suitable direction. In this illustrated embodiment, because of the shape of the body of the PTFE tubing, to body of the PTFE tubing is continuously rotated to completely coat the unmasked portions of the body of the PTFE tubing. Such a process ensures that the coating is applied to the unblocked, unprotected, unshielded or otherwise unmasked portions of the body of the PTFE tubing.

Alternative Curing Methods for Coating of PTFE Tubing

In one or more of the embodiments described herein, the coated portions of the body of the PTFE tubing are exposed to temperatures equal to or higher than the temperatures that will deform the PTFE tubing (i.e., 500° F. (260° C.)) and the uncoated portions of the body of the PTFE tubing are not subjected to such high temperatures. In one embodiment, a heat shielding device, such as a slotted metal mask, is employed to shield the heat from the uncoated portions of the body of the PTFE tubing. In another embodiment, one or more cooling methods are employed to prevent the uncoated portions of the body of the PTFE tubing from reaching such high temperatures. In one such embodiment, the PTFE tubing is frozen after the coating has been selectively applied. In this embodiment, while the PTFE tubing is cold or frozen (and specifically while the PTFE tubing made from expanded PTFE is cold or frozen), a further or final cure utilizing hot air or infrared heat is used to cure the coating applied to certain portions of the body of the PTFE tubing. In another such embodiment, one or more metal heat sinks and/or air flow devices are employed to prevent the uncoated portions of the body of the PTFE tubing (and specifically the PTFE tubing made from expanded PTFE) from reaching such high temperatures. In another embodiment, nitrogen, expanding air and/or inert gasses are passed through the lumen of the PTFE tubing (and specifically the PTFE tubing made from expanded PTFE) to keep the inside of the PTFE tubing cooler. In another embodiment, one or more spot coolers, such as the Adjustable Spot Cooler—Frigid-X™ device manufactured by Nex Flow™ Air Products Corp are employed to remove heat or btu's from the lumen(s) of the PTFE tubing (and specifically the PTFE tubing made from expanded PTFE). It should be appreciated that any suitable manner of preventing one or more portions of the body of the PTFE tubing from being heated (to the decomposition temperature of such PTFE tubing) may be employed in accordance with the present disclosure.

In different embodiments, radiated heat is applied from a radiant source, such as hot air, open flame, heated filaments, or lasers. In one embodiment, hot air is blown toward a specific coated portion of the body of the PTFE tubing through a nozzle or other apparatus of directing or funneling air. In another embodiment, heat is directly applied to the surface of the coated portion of the body of the PTFE tubing coating such that intimate contact occurs between the heat source and the coated surface.

In another illustrated embodiment, as seen in FIGS. 7A and 7b, a magnetic member 404, such as a cylindrical rod formed from a magnetic-type stainless or otherwise appropriate steel, is interested into the lumen 208 of the PTFE tubing 200. In one such embodiment, the diameter of the magnetic member is less than the inner diameter of the body of the PTFE tubing such that, as described above, the inner diameter of the body of the PTFE tubing is enabled to contract during the curing process. In this embodiment, one or more induction coils 406 are then placed around the body of the PTFE tubing. The induction coils are placed along the length of the body of the PTFE tubing to correspond to the coated portions of the body of the PTFE tubing. The coated portions of the body of the PTFE tubing are then heated by magnetic induction wherein the induction coils are energized with a frequency current, which imparts thermal energy. Specifically, electrical resistance in the magnetic member causes electrical current energy to transform into heat energy. Heat from the magnetic member then transfers to the coating by thermal conduction, thus causing the coating to cure. This method also has the advantage of keeping the body of the PTFE tubing at a cooler temperature.

In another embodiment, infrared heat is directed to a portion of the coating. In one such embodiment, a first infrared bulb is placed above a coated portion of the body of the PTFE tubing and a second infrared bulb is placed below the coated portion of the body of the PTFE tubing. In this embodiment, the infrared heat is selectively applied to the coated portion of the body of the PTFE tubing. In another such embodiment, two infrared bulbs are placed relative to the coated portion of the body of the PTFE tubing and a heat shielding device, such as a slotted metal mask, is employed to shield the heat from the uncoated portions of the body of the PTFE tubing. In these embodiments, the at least partially transparent body of the PTFE tubing enables certain designated amounts of infrared heat to pass through the body of the PTFE tubing to the coating, which absorbs the heat. This method heats the coating while simultaneously keeping the uncoated portions of the body of the PTFE tubing at a cooler temperature.

In another embodiment, the anti-shrinking device includes two clamps which, along with the coated, partially cured PTFE tubing, are placed in a curing device, such as an oven, and the coated PTFE tubing is cured at 650° F. (343.33° C.) for fifteen minutes. In another embodiment, as seen in FIG. 8, one of the clamps and part of the coated, partially cured PTFE tubing are placed in a curing device, such as an oven 410, and one of the claims and part of the coated, partially cured PTFE tubing is not placed in the curing device. In this embodiment, the coated PTFE tubing which is placed in the curing device is cured at 650° F. (343.33° C.) for fifteen minutes to cause the coating to bond to the surface of the PTFE tubing. It should be appreciated that because these embodiments include curing both the coated portions and the uncoated portions of the PTFE tubing, the diameter of both the coated portions and the uncoated portions of the PTFE tubing are reduced.

It should be appreciated that because the holder or clamps of the anti-shrinking device may or may not be heated along with the partially cured PTFE tubing and because a portion of the PTFE tubing disclosed herein may be discarded, any suitable type of holder made of any suitable material may be used in accordance with the present disclosure. In one such embodiment, as seen in FIG. 8, a first type of holder 402c, such as a metal holder suitable to be placed in a curing device, such as an oven, is used to secure a first end of the body of the coated PTFE tubing and a second type of holder 402d not suitable to be placed in a curing device, such as a silicone rubber or rubber molded clamp, is used to secure a second end of the body of the coated PTFE tubing. In one embodiment, the holders or clamps of at least one of the ends of the partially cured PTFE tubing directly engage the surface of the PTFE tubing. In this embodiment, the clamp engages a designated length, such as two inches, of the outer surface of the body of the PTFE tubing to hold the body of the PTFE tubing secure and limit or prevent the body of the PTFE tubing from shrinking. In another embodiment, one or more of the clamps is configured with a support member which is partially inserted into the lumen of the PTFE tubing. In this embodiment, the support member engages the inner surface of the body of the PTFE tubing and the clamp engages a designated length of the outer surface of the body of the PTFE tubing to hold the body of the PTFE tubing secure and limit or prevent the body of the PTFE tubing from shrinking.

As described above, because the force applied by the clamps or holders of the anti-shrinking device may damage the PTFE tubing, certain of the clamps are often employed when one piece of PTFE tubing is coated and then cut into a plurality of smaller pieces of PTFE tubing (with the damaged ends cut and discarded). In another embodiment, rather than the holders or clamps directly engaging the body of the PTFE tubing, a protector, such as a pad, is placed between at least one of the holders and the body of the PTFE tubing. Such protectors prevent the holders or clamps from directly engaging the body of the PTFE tubing and protect the PTFE tubing from any damage potentially caused by the clamping of the PTFE tubing.

In another embodiment, monel or inconel rings (which are resistance heated) emit convection heat to cure the coated portions of the body of the PTFE tubing. In one such embodiment, electrical current is passed thru horse shoe shaped inconel rings to raise the temperature of the inconel ring to 2000° F. (1093.33° C.). The inconel ring then emits both convection heat and infrared energy to cure the coating selectively applied to a portion of the outer surface of the body of the PTFE tubing.

In another embodiment, microwave heat is used to cure the coated portions of the body of the PTFE tubing. In another embodiment, one or more of the heat or energy sources described herein is coupled with the flow of water, oil or any suitable heat dispersing fluid thru the PTFE tubing (or thru a fluid containing device inserted into the lumen of the PTFE tubing) to facilitate the selective curing of certain coated portions of the body of the PTFE tubing. In another embodiment, heating elements having an outer diameter smaller than the lumen of the PTFE tubing are inserted into the lumen of the PTFE tubing and cure the applied coating. In one such embodiment, one or more heated tubes which use compressed air passing thru a heated tube are placed relative to the coated portions of the body of the PTFE tubing and are utilized to selectively heat such coated portions of the body of the PTFE tubing.

It should be appreciated that any suitable external energy source, such as flame heat, short and medium wave infrared, hot air (electrically heated) with accurately placed orifices to make a specific and accurate marks on the PTFE tubing, induction heat provided through a "bobby pin" or circular shaped coil and/or at right angles, heat provided using induction energy, and/or any combination of the curing methods disclosed herein may be used to cure the applied coating.

In another embodiment, one or more anti-shrinking devices, (such as one or more cylindrical metal rod support members or one or more tubing support members which may/may not be heated and/or cooled with liquids and/or gasses) are inserted into one or more defined lumens of the PTFE tubing. In this embodiment, when on or more portions of the body of the PTFE tubing are selectively cured, a portion of the heat or energy from the selective cure is transferred from the PTFE tubing to the support member. Such heat or energy transfer at least partially dissipates the heat or energy and reduces the temperature which the surface of the PTFE tubing rises to (or at least which the uncured surface of the PTFE tubing rises to) and thus reduces the decomposition, warp and shrinkage of the PTFE tubing (both along the circumference of the PTFE tubing and along the length of the PTFE tubing). Accordingly, such anti-shrinking devices serves a plurality of different functions including supporting the PTFE tubing during coating and curing, facilitating in the rotation of the PTFE tubing during coating and curing, absorbing and dissipating heat applied to the PTFE tubing during curing.

Figure 11A:
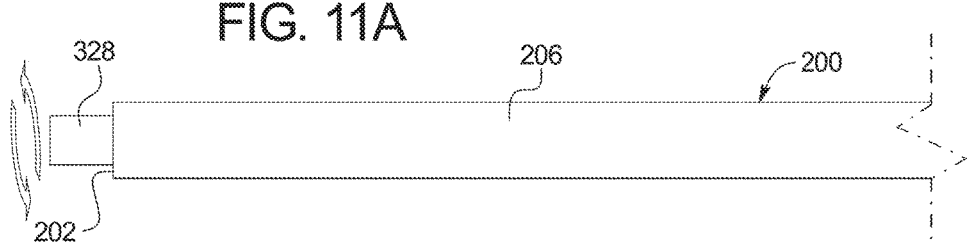
FIG. 11A is a fragmentary side view of a rotating PTFE tubing disclosed herein which is uncoated and uncured.
Figure 11B:
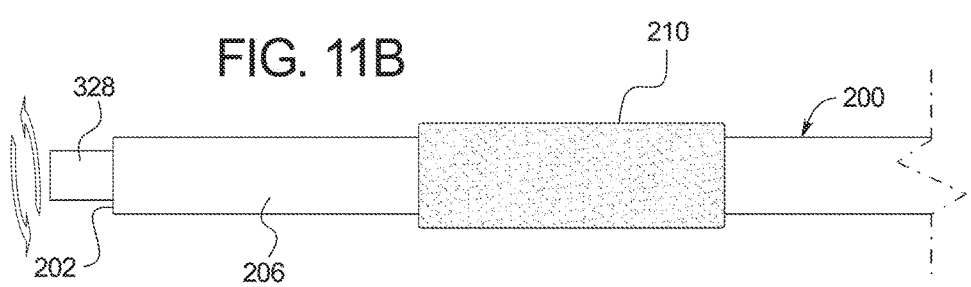
FIG. 11B is a fragmentary side view of the rotating PTFE tubing of FIG. 11A which is coated and uncured.
Figure 11C:
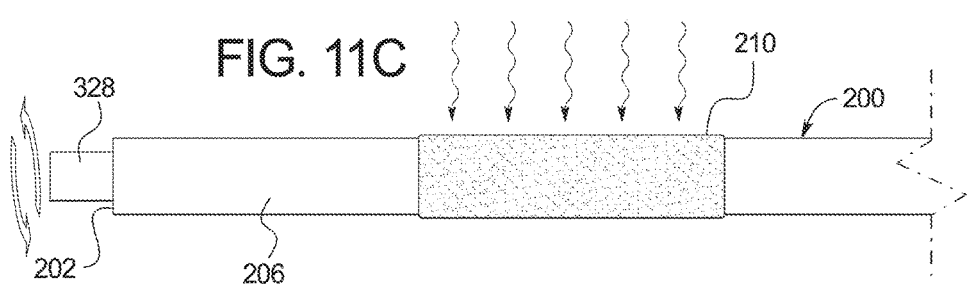
FIG. 11C is a fragmentary side view of the rotating PTFE tubing of FIG. 11B which is coated and partially cured.
Figure 11D:
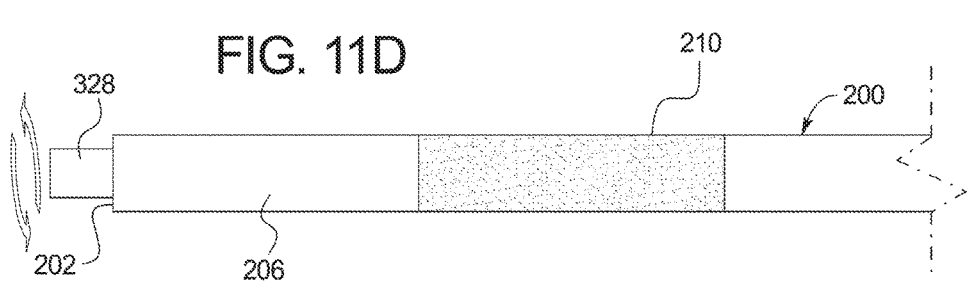
FIG. 11D is a fragmentary side view of the rotating PTFE tubing of FIG. 11D which is coated and further cured.

In another embodiment, one or more anti-shrinking devices are inserted into one or more defined lumens of the PTFE tubing and the PTFE tubing is then rotated to further increase the distribution of the heat or energy transferred to the PTFE tubing. In one such embodiment, as seen in FIG. 11A, to facilitate the rotation of the PTFE tubing, an anti-shrinking device, such as support member 328 is inserted into the lumen of the PTFE tubing and the anti-shrinking device is connected to a rotating device which causes the anti-shrinking device (and the PTFE tubing) to rotate in either a clockwise or a counterclockwise direction. In this example, as seen in FIG. 11C, following the application of the coating 210 to a first unshielded portion of the body of the PTFE tubing, the coated portion of the body of the PTFE tubing is selectively heated (without heating the uncoated portions of the body of the PTFE tubing). As seen in FIG. 11D, such selective heating coupled with the rotation of the PTFE tubing causes the diameter of the body of the PTFE tubing at these cured portions to contract or shrink. Accordingly, in various embodiments of the present disclosure, to prevent the cured and uncured portions of the marked PTFE tubing from having different outer diameters, the amount of subsequent reduction in the diameter at certain portions of the PTFE tubing is accounted for when determining a thickness or amount of coating to be applied to certain portions of the PTFE tubing.

In another embodiment, a supporting member is configured to utilize the contraction or shrinkage of the cured portions of the PTFE tubing. In one such embodiment, the supporting member is configured such that the cure of the PTFE tubing selectively reduces the size or diameter of the PTFE tubing to create a PTFE tubing with optimum dimensions and markings permanently bonded in the appropriate areas. For example, if a support member with tapered end(s) is inserted into the lumen of the PTFE tubing, then after the further cure, the end(s) of the PTFE tubing will contract or shrink to create tapered end(s). In this example, such created tapered end(s) provide for easier insertion into a patient.

In another embodiment, one side of the surface of the PTFE tubing is cured while the opposite side of the surface of the PTFE tubing is cooled to further control the shrinking or compacting of the PTFE tubing.

Additional Markings/Coatings on PTFE Tubing

In another embodiment, in addition to the markings formed along the surface of the body of the PTFE tubing by selectively applying one or more coatings, one or more additional markings are created in either the applied coating or the surface of an uncoated portion of the body of the PTFE tubing. For example, laser energy, from a $CO_2$ laser, a fiber laser or a YAG laser, is utilized to ablate a distinctive mark or markings into either the coating applied to the surface of the PTFE tubing or the surface of an uncoated portion of the body of the PTFE tubing. For example, a coating of a first color, such as black, is applied to a portion of the body of the PTFE tubing and then a $CO_2$ laser is utilized to laser engrave a contrasting marking, such as a work number or a part number, in the coated and cured portion of the body of the PTFE tubing.

Such additional markings indicate one or more of: a length, a size of the PTFE tubing, a type of the PTFE tubing, a material, a part number of the PTFE tubing, a serial number of the PTFE tubing, a lot number of the PTFE tubing, a manufacturing date of the PTFE tubing, a manufacturer of the PTFE tubing, a bar code or other code, a property or instruction associated with the PTFE tubing, an arrow, a band or a stripe along the entire length or along selected lengths from the distal end to the proximal end of the PTFE tubing, a linear line, a band or stripe along the longitudinal axis of the PTFE tubing, spiral patterned lines, bands or stripes along the length of the PTFE tubing, parallel lines, bands or stripes, perpendicular lines, bands or stripes, transverse lines, bands or stripes, any indicia or marking disclosed herein or any combination thereof.

In another embodiment, a clear or transparent top coat is applied to one or more of the surfaces of the body of the coated PTFE tubing after the coating has been selectively applied to the exposed surfaces of the body of the PTFE tubing. In one embodiment, the top coating is a low-friction or release coating or material, such as fluorinated materials, polytetrafluoroethylene, microfine FEP, melt processable pigmented powders made into liquid coatings, a low-melt low-molecular weight PTFE resin with the appropriate pigments, perfluoro-alkoxy, fluoroethylenepropylene, MFA, microfine MFA, polyethylene, silicone, a resin like clear medical grade epoxy in liquid or power form, ceramic composites, paralyene silane polymers and other suitable low-friction coatings. Such a top coating provides that the markings described above are substantially covered or sealed underneath an additional layer skin of a low-friction coating.

Further Alternative Embodiments

In another embodiment, to account for the reduction in diameter of the body of the PTFE tubing caused by the curing process, prior to the final cure of the body of the coated PTFE tubing, a support and anti-shrinking device, such as a cylindrical metal rod or a hollow tube (which may/may not be heated and/or cooled with liquids and/or gasses), is inserted into the defined lumen of the PTFE tubing. In another embodiment wherein the PTFE tubing defines a plurality of lumens, the support device is configured to be inserted into one or more of the plurality of lumens defined by the PTFE tubing. In these embodiments, the support device prevents or inhibits the inner diameter of the body of the PTFE tubing from contracting or substantially contracting when the PTFE tubing is heated. In one such embodiment, the support device further prevents the PTFE tubing from being crushed or damaged when the ends of the PTFE tubing are placed in suitable clamps. In this embodiment, the support device enables the clamp to exert additional force on the PTFE tubing without otherwise damaging the PTFE tubing.

In another embodiment, the low-friction medical device is made from a non-fluoropolymer substrate, such as metal substrate. In this embodiment, a first fluoropolymer coating including at least one pigment (or a combination of different pigments) is applied to the non-fluoropolymer substrate. After applying the first fluoropolymer coating, a second fluoropolymer coating including at least one different pigment (or a different combination of different pigments) is applied to the first fluoropolymer coating. In one such embodiment, this second fluoropolymer coating is selectively applied to the first fluoropolymer coating, such as utilizing any of the above-described shielding devices.

In this embodiment, following the application of the second fluoropolymer coating, the low-friction medical device of this embodiment is then cured to a designated temperature (such as above 500° F. (260° C.) at which the fluoropolymer coatings begin to decompose) to cause the first fluoropolymer coating to bond with the second fluoropolymer coating. As described above with respect to the curing of the coating to the low-friction medical tubing, such a cure causes the molecules at or near the surface of the applied first fluoropolymer coating and the molecules at or near the surface of the applied second fluoropolymer coating to melt. The melted coatings bond or otherwise adhere to each other to adhere the first fluoropolymer coating and the second fluoropolymer coating together. Such an embodiment thus provides a method to securely adhere one or more markings to one or more fluoropolymer coated non-fluoropolymer substrates, such as one or more PTFE coated non-fluoropolymer substrates. This embodiment thus facilitates that one or more coatings of a first color are permanently bonded to a fluoropolymer coating of a second color, such as a Teflon® coating (manufactured by DuPont™) to create one or more markings as disclosed herein.

It should be appreciated that in one such embodiment, the non-fluoropolymer substrate does not deform as a result of this cure and thus the non-fluoropolymer substrate of this embodiment does not need to be held or stabilized as described above with respect to the use of an anti-shrinking device with low-friction medical tubing. In another such embodiment, the non-fluoropolymer substrate deforms as a result of this cure and thus the non-fluoropolymer substrate of this embodiment needs to be held or stabilized as described above with respect to the use of an anti-shrinking device with low-friction medical tubing.

It should be appreciated that any of the methods of manufacturing PTFE tubing disclosed herein may be fully or partially manually performed. It should also be appreciated that any of the methods of manufacturing PTFE tubing disclosed herein may be fully or partially automated for precision. It should further be appreciated that any of the methods of manufacturing PTFE tubing disclosed herein may be individually performed on a single PTFE tube or simultaneously performed for a plurality of PTFE tubes.

For the purposes of this application only, the low-friction medical device is referred to and illustrated as medical tubing or PTFE tubing. However, the low-friction medical device disclosed herein can also be any low-friction device that is inserted into a patient or connects to a low-friction device that inserts a device into a patient in connection with any medical procedure. Such suitable low-friction medical devices include, but are not limited to: medical tubes, intravenous therapy (IV) tubes, valves, ports, medical wires, medical tapes, medical guide wires, catheters, needles, soft tissue needles, biopsy devices, biopsy tubular sampling devices, soft tissue biopsy devices, soft tissue tubular devices, hook-type biopsy devices, laminates, vents, medical patches, orthapaedic implants (made from fluoropolymers, such as e-PTFE), fluoropolymer based low-friction implantable surfaces, cannulas, probes, electrosurgical electrodes, sheets, gaskets, blades and knives. For example, any suitable low friction, low surface area medical device which flexes, bends or is required to move in any suitable direction may be marked or coated in accordance with the present disclosure. In different embodiments, the low-friction medical device is constructed from any suitable low-friction and/or low surface energy material, including but not limited to one or more of: solid PTFE, non-solid PTFE, expanded PTFE, porous PTFE, micro-porous PTFE, cellular PTFE, fluorinated ethylene propylene (FEP), polyethylene (PE), perfluoroalkoxy (PFA), any suitable fluoropolymer or any low surface energy particulate material. Other suitable materials of which a medical device may be constructed include but are not limited to one or more of: natural materials, synthetic materials, combinations of natural and synthetic materials, polyamides, non-metallic composite materials, metals such as steel (both high-carbon and low-carbon content), stainless steel, aluminum, titanium, copper, nickel, bronze, silver, nitinol and other metals or metal alloys, glass, acrylic, carbon, graphite, cellulose, fabric, ceramics, rubber, any suitable polymer material and any suitable plastic, including but not limited to: nylon, polyetheretherketone (PEEK), polyetherketone (PEK), polyphenylenesulphide (PPS), acrylonitrile-butadiene-styrene (ABS), polycarbonate, epoxy, polyester, and phenolic, or any combination thereof. It should also be appreciated that in certain embodiments in which the medical device is a different device than the medical tubing described herein, the shielding device and/or the anti-shrinking device utilized as described above is suitable shaped and configured to operate with this different device.

It should further be appreciated that while the above-described embodiments pertaining to applying a coating, curing the applied coating to a designated temperature, utilizing one or more anti-shrinking devices and exhausting any potentially harmful byproducts are described and illustrated in relation to medical tubing or PTFE tubing, these above-described embodiments may also be utilized with respect to any suitable low-friction non-medical device. Such suitable low-friction non-medical devices include, but are not limited to: sight tubes, air meters, gas meters, flow meters which include a ball inside a tube, beakers, beaker covers, test tubes, centrifuge tubes, flasks, volumetric flasks, Erlenmeyer flasks, ampules, burettes, condensers, cuvettes, cylinders, dishes, well plates, mortars, pestles, bottles, dropping bottles, bottle pourers, wash bottles, carboys, jars, vials, sleeves, sleeves for glass joints, adapters for glass joints, funnels, Buchner funnels, evaporating dishes, petri dishes, crucibles, syringes, micro-titre plates, dippers, ladles, scoopers, bags, stir bars, magnetic stir bars, tweezers, forceps, cookware, bakeware, sports strings, musical strings, transparent vessels, translucent vessels, and molded containers. In different embodiments, the non-medical device is constructed from any suitable low-friction and/or low surface energy material, including but not limited to one or more of: solid PTFE, non-solid PTFE, expanded PTFE, porous PTFE, micro-porous PTFE, cellular PTFE, fluorinated ethylene propylene (FEP), polyethylene (PE), perfluoroalkoxy (PFA), any suitable fluoropolymer or any low surface energy particulate material. Other suitable materials of which a non-medical device may be constructed include, but are not limited to one or more of: natural materials, synthetic materials, combinations of natural and synthetic materials, polyamides, non-metallic composite materials, metals such as steel (both high-carbon and low-carbon content), stainless steel, aluminum, titanium, copper, nickel, bronze, silver, nitinol and other metals or metal alloys, glass, acrylic, carbon, graphite, cellulose, fabric, ceramics, rubber, any suitable polymer material and any suitable plastic, including but not limited to: nylon, polyetheretherketone (PEEK), polyetherketone (PEK), polyphenylenesulphide (PPS), acrylonitrile-butadiene-styrene (ABS), polycarbonate, epoxy, polyester, and phenolic, or any combination thereof. It should also be appreciated that in certain embodiments in which the non-medical device is a different device than the tubing described herein, the shielding device and/or the anti-shrinking device utilized as described above is suitable shaped and configured to operate with this different device.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of manufacturing a coated polytetrafluoroethylene tube, said method comprising:
    inserting a support member into a lumen of a body of a polytetrafluoroethylene tube;
    coupling the support member and the body of the polytetrafluoroethylene tube to a shielding device;
    blocking, via the shielding device, a plurality of spaced apart portions of an outer surface of the body of the polytetrafluoroethylene tube;
    rotating the support member and the body of the polytetrafluoroethylene tube;
    while rotating the support member and the body of the polytetrafluoroethylene tube, applying a coating to each of a plurality of spaced apart unblocked portions of the outer surface of the body of the polytetrafluoroethylene tube; and
    curing the applied coating to cause the applied coating to bond to the outer surface of the body of the polytetrafluoroethylene tube to indicate a plurality of spaced apart markings formed on the outer surface of the body of the polytetrafluoroethylene tube.

2. The method of claim 1, wherein the support member includes a cylindrical rod.

3. The method of claim 1, wherein the support member includes a hollow tube.

4. The method of claim 1, wherein the support member has an outer diameter that is smaller than an inner diameter of the lumen of the body of the polytetrafluoroethylene tube.

5. The method of claim 1, which includes securing the body of the polytetrafluoroethylene tube to the support member.

6. The method of claim 1, wherein the support member is longer than the body of the polytetrafluoroethylene tube.

7. The method of claim 1, wherein coupling the support member and the body of the polytetrafluoroethylene tube to the shielding device includes attaching the support member to a first member of the shielding device.

8. The method of claim 7, wherein blocking, via the shielding device, the plurality of spaced apart portions of the outer surface of the body of the polytetrafluoroethylene tube includes attaching a second member to the first member, the second member including a plurality of blocking portions.

9. The method of claim 8, wherein the second member defines a plurality of apertures.

10. The method of claim 8, wherein the second member is securable to the first member.

11. The method of claim 8, wherein the second member defines a plurality of slots.

12. The method of claim 8, wherein the second member defines a plurality of semi-cylindrical tube engagement surfaces.

13. The method of claim 7, wherein the first member defines a plurality of semi-cylindrical tube engagement surfaces.

14. The method of claim 1, wherein the coating includes a polytetrafluoroethylene.

15. The method of claim 1, wherein the coating includes a binder selected from the group consisting of: an epoxy, a phenolic, a phenoxy, a polyimide, a polyamide, a polyamide-amide, a polyphenylene sulfide, a polyarylsulfone, polyethylene, a polytetrafluoroethylene, a fluorinated ethylene propylene, a perfluoroalkoxy, tetrafluoroethylene-hexafluoropropylene, a polyetheretherketone, a polyetherketone, and a tetrafluoroethylene perfluoromethyl vinyl ether copolymer.

16. The method of claim 1, wherein the coating includes a pigment selected from the group consisting of: an organic pigment, an inorganic pigment, an extender pigment, a magnetic receptive pigment, and a laser excitable pigment.

17. The method of claim 1, wherein the coating includes a pigment selected from a group consisting of: a phthalocyanine blue, a phthalocyanine green, a diarylide yellow, a diarylide orange, a quanacridone, a naphthol, a toluidine red, a carbizole violet, a carbon black, an iron oxide red, an iron oxide yellow, a chrome oxide green, a titanium oxide white, a cadmium red, a ultramarine blue, a moly orange, a lead chromate yellow, a mixed metal oxide, a talc, a calcium carbonate, a silicate and sulfate, a silica, a mica, an aluminum hydrate and silicate, a barium sulfate, a pearl pigment, a kaolin, an aluminum silicate derivative, an antomony trioxide, a metallic pigment, an aluminum flake pigment, and an iron oxide.

18. The method of claim 1, wherein the coating includes a plurality of anti-microbial particles.

19. The method of claim 18, wherein the anti-microbial particles are selected from the group consisting of: silver particles, glass-silver particles, silver-ceramic particles, and ceramic particles.

20. The method of claim 1, wherein the polytetrafluoroethylene tube is selected from the group consisting of: a cellular polytetrafluoroethylene tube, a porous polytetrafluoroethylene tube, and an expanded polytetrafluoroethylene tube.

21. The method of claim 1, wherein applying the coating to each of the plurality of spaced-apart unblocked portions of the outer surface of the body of the polytetrafluoroethylene tube includes: (i) applying the coating to a first one of the unblocked portions of the outer surface of the body of the polytetrafluoroethylene tube; and (ii) subsequently applying the coating to a second one of the unblocked portions of the outer surface of the body of the polytetrafluoroethylene tube.

22. The method of claim 1, wherein applying the coating to each of the plurality of spaced-apart unblocked portions of the outer surface of the body of the polytetrafluoroethylene tube includes: (i) applying the coating to a first one of the unblocked portions of the outer surface of the body of the polytetrafluoroethylene tube; and (ii) simultaneously applying the coating to a second one of the unblocked portions of the outer surface of the body of the polytetrafluoroethylene tube.

23. The method of claim 1, wherein curing the applied coating includes heating the coating to a designated temperature for a designated period of time.

24. The method of claim 23, wherein the designated temperature is at least a decomposition temperature of the polytetrafluoroethylene tube.

25. The method of claim 1, wherein curing the applied coating includes heating the coating and the body of the polytetrafluoroethylene tube to a designated temperature for a designated period of time.

26. The method of claim 25, wherein the designated temperature is at least a decomposition temperature of the polytetrafluoroethylene tube.

27. The method of claim 1, wherein curing the applied coating includes heating the coating and a plurality of selective portions of the body of the polytetrafluoroethylene tube to which the coating is applied to a designated temperature for a designated period of time.

28. The method of claim 27, wherein the designated temperature is at least a decomposition temperature of the polytetrafluoroethylene tube.

29. The method of claim 27, wherein heating the coating and plurality of selective portions of the body of the polytetrafluoroethylene tube to which the coating is applied includes using an energy source selected from the group consisting of: a radiant heat, induction energy, hot air, open flame, at least one electric filament, at least one magnet, and at least one laser.

30. The method of claim 29, wherein the designated temperature is at least a decomposition temperature of the polytetrafluoroethylene tube.

31. The method of claim 1, wherein curing the applied coating includes using an energy source selected from the group consisting of: a radiant heat, induction energy, hot air, open flame, at least one electric filament, at least one magnet, and at least one laser.

32. The method of claim 1, wherein the plurality of spaced apart markings are selected from the group consisting of: at least one line perpendicular to a longitudinal direction of the body of the polytetrafluoroethylene tube, at least one line transverse to the longitudinal direction of the body of the polytetrafluoroethylene tube, and at least one line substantially transverse to the longitudinal direction of the body of the polytetrafluoroethylene tube.

33. The method of claim 1, wherein the support member functions as an anti-shrinking device when in the lumen of the body of the polytetrafluoroethylene tubing.

34. The method of claim 1, which includes allowing the body of the polytetrafluoroethylene tube to shrink in a longitudinal direction of the body of the polytetrafluoroethylene tube such that the plurality of spaced-apart markings are at desired positions along the body of the polytetrafluoroethylene tube after such shrinkage.

35. The method of claim 1, wherein coupling the support member and the body of the polytetrafluoroethylene tube to the shielding device includes attaching the support member to the shielding device without the outer surface of the body of the polytetrafluoroethylene tube contacting the shielding device.

36. The method of claim 1, which includes applying a top coat to the cured coating and the body of the polytetrafluoroethylene tube.

* * * * *